US012091688B2

(12) United States Patent
Izhar et al.

(10) Patent No.: US 12,091,688 B2
(45) Date of Patent: Sep. 17, 2024

(54) OMNI-103 CRISPR NUCLEASE

(71) Applicants: EmendoBio Inc., Wilmington, DE (US); Lior Izhar, Tel Aviv (IL); Nadav Marbach Bar, Rehovot (IL); Liat Rockah, Rishon LeZion (IL); Nir Hecht, Tel Aviv (IL)

(72) Inventors: Lior Izhar, Tel Aviv (IL); Nadav Marbach Bar, Rehovot (IL); Liat Rockah, Rishon LeZion (IL); Nurit Meron, Ramat Gan (IL); Ophir Adiv Tal, Rehovot (IL); Ariel Gispan, Kfar Adumim (IL); Idit Buch, Hod-Hasharon (IL); Nir Hecht, Tel Aviv (IL)

(73) Assignee: EmendoBio Inc., Wilmington, DE (US)

( * ) Notice: Subject to any disclaimer, the term of this patent is extended or adjusted under 35 U.S.C. 154(b) by 0 days.

(21) Appl. No.: 18/006,372

(22) PCT Filed: Feb. 7, 2022

(86) PCT No.: PCT/US2022/015504

§ 371 (c)(1),
(2) Date: Jan. 20, 2023

(87) PCT Pub. No.: WO2022/170199

PCT Pub. Date: Aug. 11, 2022

(65) Prior Publication Data

US 2023/0303989 A1 Sep. 28, 2023

Related U.S. Application Data

(60) Provisional application No. 63/286,885, filed on Dec. 7, 2021, provisional application No. 63/214,506, filed on Jun. 24, 2021, provisional application No. 63/147,166, filed on Feb. 8, 2021.

(51) Int. Cl.
*C12N 9/22* (2006.01)
*C12N 15/11* (2006.01)

(52) U.S. Cl.
CPC ................ *C12N 9/22* (2013.01); *C12N 15/11* (2013.01); *C12N 2310/20* (2017.05); *C12N 2310/531* (2013.01); *C12N 2800/80* (2013.01)

(58) Field of Classification Search
CPC ........................................................ C12N 9/22
See application file for complete search history.

(56) References Cited

U.S. PATENT DOCUMENTS 11,666,641 B2 6/2023 Baram
2019/0264232 A1 8/2019 Hou et al.
2022/0154157 A1 5/2022 Baram
2022/0202913 A1 6/2022 Baram
2022/0213456 A1 7/2022 Baram
2023/0122086 A1 4/2023 Izhar

FOREIGN PATENT DOCUMENTS

WO WO 2017/184768 A1 10/2017
WO WO 2018/172556 A1 9/2018
WO WO 2020/069029 A1 4/2020
WO WO 2020/223514 A2 11/2020
WO WO 2022/087135 A1 4/2022
WO WO 2022/098693 A1 5/2022
WO WO 2022/170199 A2 8/2022
WO WO 2022/170216 A2 8/2022
WO WO2022/226215 A1 10/2022
WO WO 2023/019263 A1 2/2023
WO WO 2023/019269 A2 2/2023
WO WO 2023/091987 A2 5/2023
WO WO 2023/102407 A2 6/2023
WO WO 2023/107946 A2 6/2023

OTHER PUBLICATIONS

International Search Report issued Jul. 15, 2022 in connection with PCT International Application No. PCT/US2022/015504.
Notification of Transmittal of the International Search Report and the Written Opinion of the International Searching Authority, or the Declaration issued Jul. 15, 2022 in connection with PCT International Application No. PCT/US2022/015504.
Written Opinion of the International Searching Authority issued Jul. 15, 2022 in connection with PCT International Application No. PCT/US2022/015504.

*Primary Examiner* — Suzanne M Noakes
(74) *Attorney, Agent, or Firm* — Jamaica P. Szeliga; Potomac Law Group PLLC

(57) ABSTRACT

The present invention provides a non-naturally occurring composition comprising a CRISPR nuclease comprising a sequence having at least 95% identity to the amino acid sequence of SEQ ID NO: 1 or a nucleic acid molecule comprising a sequence encoding the CRISPR nuclease.

24 Claims, 17 Drawing Sheets

Specification includes a Sequence Listing.

sgRNA 12 V2

TRAC S35

```
1        10        20      28
GACCCTGCCGTGTACCAGCTGANNNACT   Reads
........................G...   4855 (100.0%)
```

PDCD1 S40

```
1        10        20      28
AACACATCGGAGAGCTTCGTGCNNNACT   Reads
........................A...   1333 (92.44%)
........................A...   109 (7.56%)
```

OMNI-103, sgRNA_12

| | | |
|---|---|---|
| 103.v2 | GTTTGAGAGTAGTGTAAGAAATTACACTACAAGTTCAAATAAAAATTTATTCAAATCCATTTGCTACATTGTGTAGAATTTAAAGATCTGGCAACAGATCTTTTTTT | 107 |
| OMNI-103.1 | GTTTGAGAGTAGTG---GAAA---CACTACAAGTTCAAATAAAAATTTATTCAAATCCATTTGCTACATTGTGTAGAATTTAAAGATCTGGCAACAGATCTTTTTTT | 101 |
| OMNI-103.2 | GTTTGAGAGTAGTGTAAGAAATTACACTACAAGTTCAAATAAAAATTTATTCAAATCCATTTGCTACATTGTGTAGAA----------------------TTTTTTT | 85 |
| OMNI-103.3 | GTTTGAGAGTAGTG---GAAA---CACTACAAGTTCAAATAAAAATTTATTCAAATCCATTTGCTACATTGTGTAGAA----------------------TTTTTTT | 79 |
| OMNI-103.4 | GTTTGAGAGTAGTG---GAAA---CACTACAAGTTCAAATAAAAATTTATTCAAATCCATTTGCTACATTGTGTAGAATTTAAAGAT---GCAA---ATCTTTTTTT | 95 |

Fig. 5A

| Sample Name | % TCR Negative (% editing) | GeoMean |
|---|---|---|
| V2.3 | 90.8 | 2511 |
| V2.2 | 87.6 | 2621 |
| V2 | 77.4 | 3324 |
| Non Treated (Positive control) | 6.28 | 12617 |
| IgG control (Negative control) | 100 | 924 |

| Sample Name | % TCR Negative (% editing) | GeoMean |
|---|---|---|
| V2.3 | 91.6 | 7710 |
| V2.2 | 88 | 5581 |
| V2 | 79.9 | 8029 |
| Non Treated (Positive control) | 1.56 | 7.59E5 |
| IgG control (Negative control) | 99.8 | 257 |

| Sample Name | CD3+ :: Freq. of Parent | Geometric Mean : FL5-A |
| --- | --- | --- |
| 01-4200-86.fcs | 96.9 | 16409 |
| 01-REA-A6.fcs | 1.98 | 1543 |

| Sample Name | CD25+ :: Freq. of Parent | Geometric Mean : FL7-A |
| --- | --- | --- |
| 01-4200-86.fcs | 85.3 | 27069 |
| 01-REA-A6.fcs | 3.96 | 176 |

OMNI-103 CRISPR NUCLEASE

CROSS-REFERENCE TO RELATED APPLICATIONS

This application is a § 3.71 national stage of PCT International Application No. PCT/US2022/015504, filed Feb. 7, 2022, claiming the benefit of U.S. Provisional Application No. 63/286,855, filed Dec. 7, 2021, U.S. Provisional Application No. 63/214,506, filed Jun. 24, 2021, and U.S. Provisional Application No. 63/147,166, filed Feb. 8, 2021, the contents of each of which are hereby incorporated by reference into the subject application.

Throughout this application, various publications are referenced, including referenced in parenthesis. The disclosures of all publications mentioned in this application in their entireties are hereby incorporated by reference into this application in order to provide additional description of the art to which this invention pertains and of the features in the art which can be employed with this invention.

REFERENCE TO SEQUENCE LISTING

This application incorporates-by-reference nucleotide sequences which are present in the file named "230120_91677_A_PCT_US_Sequence_Listing_AD.txt", which is 86 kilobytes in size, and which was created on Jan. 20, 2023 in the IBM-PC machine format, having an operating system compatibility with MS-Windows, which is contained in the text file filed Jan. 20, 2023 as part of this application.

FIELD OF THE INVENTION

The present invention is directed to, inter alia, composition and methods for genome editing.

BACKGROUND OF THE INVENTION

The Clustered Regularly Interspaced Short Palindromic Repeat (CRISPR) systems of bacterial and archaeal adaptive immunity show extreme diversity of protein composition and genomic loci architecture. The CRISPR systems have become important tools for research and genome engineering. Nevertheless, many details of CRISPR systems have not been determined and the applicability of CRISPR nucleases may be limited by sequence specificity requirements, expression, or delivery challenges. Different CRISPR nucleases have diverse characteristics such as: size, PAM site, on target activity, specificity, cleavage pattern (e.g. blunt, staggered ends), and prominent pattern of indel formation following cleavage. Different sets of characteristics may be useful for different applications. For example, some CRISPR nucleases may be able to target particular genomic loci that other CRISPR nucleases cannot due to limitations of the PAM site. In addition, some CRISPR nucleases currently in use exhibit pre-immunity, which may limit in vivo applicability. See Charlesworth et al., Nature Medicine (2019) and Wagner et al., Nature Medicine (2019). Accordingly, discovery, engineering, and improvement of novel CRISPR nucleases is of importance.

SUMMARY OF THE INVENTION

Disclosed herein are compositions and methods that may be utilized for genomic engineering, epigenomic engineering, genome targeting, genome editing of cells, and/or in vitro diagnostics.

The disclosed compositions may be utilized for modifying genomic DNA sequences. As used herein, genomic DNA refers to linear and/or chromosomal DNA and/or plasmid or other extrachromosomal DNA sequences present in the cell or cells of interest. In some embodiments, the cell of interest is a eukaryotic cell. In some embodiments, the cell of interest is a prokaryotic cell. In some embodiments, the methods produce double-stranded breaks (DSBs) at predetermined target sites in a genomic DNA sequence, resulting in mutation, insertion, and/or deletion of a DNA sequence at the target site(s) in a genome.

Accordingly, in some embodiments, the compositions comprise a Clustered Regularly Interspaced Short Palindromic Repeat (CRISPR) nucleases. In some embodiments, the CRISPR nuclease is a CRISPR-associated protein.

OMNI-103 CRISPR Nuclease

Embodiments of the present invention provide for CRISPR nucleases designated as an "OMNI-103" nuclease as provided in Table 1.

This invention provides a method of modifying a nucleotide sequence at a target site in the genome of a mammalian cell comprising introducing into the cell (i) a composition comprising a CRISPR nuclease having at least 95% identity to the amino acid sequence of SEQ ID NO: 1 or a nucleic acid molecule comprising a sequence encoding a CRISPR nuclease which sequence has at least 95% identity to the nucleic acid sequence of SEQ ID NOs: 2-3 and (ii) a DNA-targeting RNA molecule, or a DNA polynucleotide encoding a DNA-targeting RNA molecule, comprising a nucleotide sequence that is complementary to a sequence in the target DNA.

This invention also provides a non-naturally occurring composition comprising a CRISPR associated system comprising:

a) one or more RNA molecules comprising a guide sequence portion linked to a direct repeat sequence, wherein the guide sequence is capable of hybridizing with a target sequence, or one or more nucleotide sequences encoding the one or more RNA molecules; and b) an CRISPR nuclease comprising an amino acid sequence having at least 95% identity to the amino acid sequence of SEQ ID NO: 1 or a nucleic acid molecule comprising a sequence encoding the CRISPR nuclease; and wherein the one or more RNA molecules hybridize to the target sequence, wherein the target sequence is adjacent to a complimentary sequence of a Protospacer Adjacent Motif (PAM), and the one or more RNA molecules form a complex with the RNA-guided nuclease.

This invention also provides a non-naturally occurring composition comprising:

a) a CRISPR nuclease comprising a sequence having at least 95% identity to the amino acid sequence of SEQ ID NO: 1 or a nucleic acid molecule comprising a sequence encoding the CRISPR nuclease; and b) one or more RNA molecules, or one or more DNA polynucleotide encoding the one or more RNA molecules, comprising at least one of:

i) a nuclease-binding RNA nucleotide sequence capable of interacting with/binding to the CRISPR nuclease; and ii) a DNA-targeting RNA nucleotide sequence comprising a sequence complementary to a sequence in a target DNA sequence, wherein the CRISPR nuclease is capable of complexing with the one or more RNA molecules to form a complex capable of hybridizing with the target DNA sequence.

OMNI-103 CRISPR Nuclease-RNA Complexes

The invention also provides a composition comprising a non-naturally occurring RNA molecule, the RNA molecule comprising a crRNA repeat sequence portion and guide sequence portion, wherein the RNA molecule forms a complex with and targets an OMNI-103 nuclease to a DNA target site in the presence of a tracrRNA sequence, wherein the tracrRNA sequence is encoded by a tracrRNA portion of the RNA molecule or a tracrRNA portion of a second RNA molecule.

The invention also provides a composition comprising a non-naturally occurring RNA molecule, the RNA molecule comprising an RNA scaffold portion, the RNA scaffold portion having the structure:

crRNA repeat sequence portion-tracrRNA portion;

wherein the RNA scaffold portion forms a complex with and targets an OMNI-103 CRISPR nuclease to a DNA target site having complementarity to a guide sequence portion of the RNA molecule.

Disclosed herein are compositions and methods that may be utilized for genomic engineering, epigenomic engineering, genome targeting, genome editing of cells, and/or in vitro diagnostics using an OMNI-103 CRISPR nuclease and a non-naturally occurring RNA molecule comprising a scaffold portion capable of specifically binding and activating the OMNI-103 CRISPR nuclease to target a DNA target site based on a guide sequence portion, also referred to as a RNA spacer portion, of the RNA molecule.

The disclosed compositions may be utilized for modifying genomic DNA sequences. As used herein, genomic DNA refers to linear and/or chromosomal DNA and/or plasmid or other extrachromosomal DNA sequences present in the cell or cells of interest. In some embodiments, the cell of interest is a eukaryotic cell. In some embodiments, the cell of interest is a prokaryotic cell. In some embodiments, the methods produce double-strand breaks (DSBs) at pre-determined target sites in a genomic DNA sequence, resulting in mutation, insertion, and/or deletion of a DNA sequence at the target site(s) in a genome.

BRIEF DESCRIPTION OF THE DRAWINGS

FIG. 1A: A representation of a crRNA-tracrRNA duplex for OMNI-103 V1 (FIG. 1A) and V2 (FIG. 1B) with the crRNA and tracrRNA portions of the sgRNA noted (See Table 2).

(FIG. 2A) For in vitro assays, reducing amounts of RNPs (4, 2, 1 and 0.5 μmol) with spacer lengths 20-25 bps (listed in Table 6) were incubated with 40 ng PDCD1 DNA target template. Activity was verified by the ability to cleave the linear template. (FIGS. 2B-C) In vivo assays (FIG. 2B) RNPs with spacer lengths (20-25 nucleotides) of PDCD1 S40 were electroporated into U2OS cell line and editing levels (indels) measured by NGS. (FIG. 2C) Activity assay for OMNI-103 as RNP in U2OS cells: RNPs with PDCD1S40, TRACS35, TRACS33 and B2M S12 (22 bp spacer length, Table 6) were electroporated into U2OS cell line and editing levels (indels) measured by next generation sequencing (NGS).

(FIG. 3A) Editing levels (indels) and dsODN integration were measured by NGS. (FIG. 3B) Guide seq analysis did not show any off-target at the PDCD1 S40 site (SEQ ID NO: 133) or TRAC S35 site (SEQ ID NO: 134).

FIGS. 4A-4B: In vitro TXTL PAM depletion results for OMNI nucleases. The PAM logo is a schematic representation of the ratio of the depleted site (top panel). Depletion ratio (bottom panel, right) of specific PAM sequences (bottom panel, left) from the PAM plasmid library were calculated following NGS of the TXTL reaction. The calculation for each OMNI is based on a 4N window along the 8 bp sequence of the PAM library. The required PAM of the tested OMNI and the level of nuclease activity under the reaction conditions is inferred from the depletion ratio. In vitro PAM depletion results for: FIG. 4A: OMNI-103 with sgRNA 12. FIG. 4B: OMNI-103 with sgRNA 32.

FIGS. 5A-5C: OMNI-103 sgRNA versions show editing in HeLa cells. To shorten the sgRNA for OMNI-103 four different versions of the scaffold were tested. These versions included deletions at the upper stem and/or at the terminal hairpin. FIG. 5A: A multiple sequence alignment of the different sgRNA designed for OMNI-103. Specifically, alignment of OMNI-103 sgRNA v2 scaffold (107 nucleotides, RNA listed as SEQ ID NO: 16) with shorter sgRNA scaffold versions OMNI-103.1 (101 nucleotides, RNA listed as SEQ ID NO: 33), OMNI-103.2 (85 nucleotides, RNA listed as SEQ ID NO: 34), OMNI-103.3 (79 nucleotides, RNA listed as SEQ ID NO: 35), and OMNI-103.4 (95 nucleotides, RNA listed as SEQ ID NO: 36). FIG. 5B: The predicted structure of sgRNA 103.v2, which was used as template creating the shorter versions (deletions used to create the shorter versions are indicated). FIG. 5C: The editing activity of OMNI-103 CRISPR nuclease with the different scaffolds as determined by next-generation sequencing (NGS). Two sites were tested TRAC S91 and PDCD S40. The transfection efficiency was determined by FACS as the plasmid expressed a reporter fluorescent protein (mCherry).

FIG. 6A: Scaffold V2. FIG. 6B: Scaffold V2.1. FIG. 6C: Scaffold V2.2. FIG. 6D: Scaffold V2.3. FIG. 6E: Scaffold V2.4. FIG. 6F: Scaffold V2.5.

DETAILED DESCRIPTION

Figures 1A, 1B:
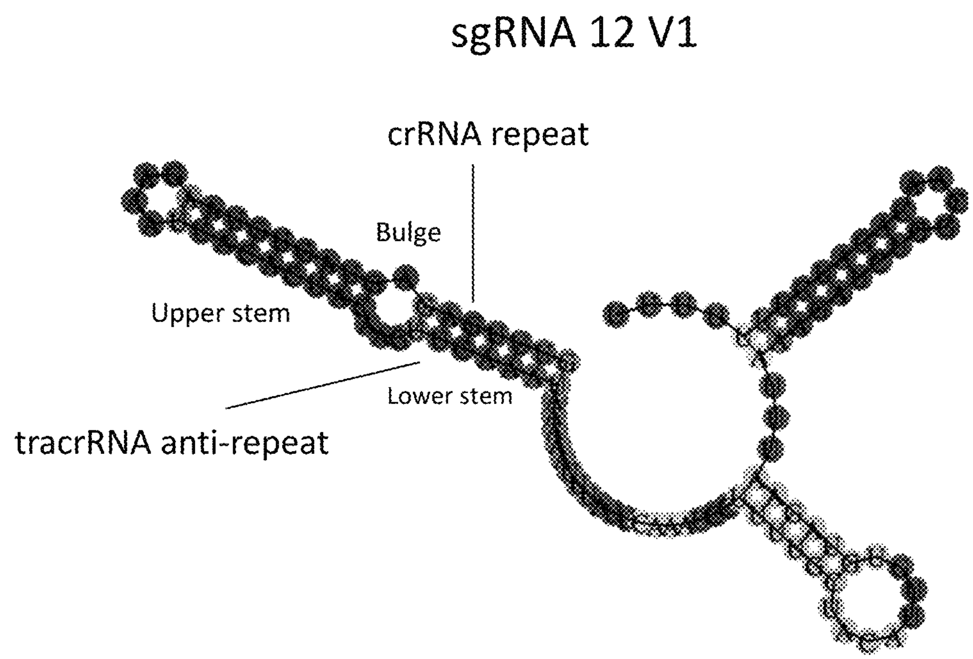
FIGS. 1A-1B: The predicted secondary structure of sgRNA12, a single guide RNA (sgRNA) (crRNA-tracrRNA) compatible with OMNI-103.

According to some aspects of the invention, the disclosed compositions comprise a Clustered Regularly Interspaced Short Palindromic Repeats (CRISPR) nuclease and/or a nucleic acid molecule comprising a sequence encoding the same.

Table 1 lists novel CRISPR nucleases, as well as substitutions at one or more positions within each nuclease which convert the nuclease to a nickase or catalytically dead nuclease.

Table 2 provides crRNA, tracrRNA, and single-guide RNA (sgRNA) sequences, and portions of crRNA, tracrRNA, and sgRNA sequences, that are compatible with each listed CRISPR nuclease. Accordingly, a crRNA molecule capable of binding and targeting an OMNI nuclease listed in Table 2 as part of a crRNA:tracrRNA complex may comprise any crRNA sequence listed in Table 2. Similarly, a tracrRNA molecule capable of binding and targeting an OMNI nuclease listed in Table 2 as part of a crRNA: tracrRNA complex may comprise any tracrRNA sequence listed in Table 2. Also, a single-guide RNA molecule capable of binding and targeting an OMNI nuclease listed in Table 2 may comprise any sequence listed in Table 2.

For example, a crRNA molecule of OMNI-103 nuclease (SEQ ID NO: 1) may comprise a sequence of any one of SEQ ID NOs: 4-7 and 18-21; a tracrRNA molecule of OMNI-103 nuclease may comprise a sequence of any one of SEQ ID NOs: 8-14, 17, 22-28, and 32; and a sgRNA molecule of OMNI-103 nuclease may comprise a sequence of any one of SEQ ID NOs: 4-36. Other crRNA molecules, tracrRNA molecules, or sgRNA molecules for each OMNI nuclease may be derived from the sequences listed in Table 2 in the same manner.

The invention provides a non-naturally occurring composition comprising a CRISPR nuclease comprising a sequence having at least 90% identity to the amino acid sequence of SEQ ID NO: 1, or a nucleic acid molecule comprising a sequence encoding the CRISPR nuclease. The nucleic acid molecule may be, for example, a DNA molecule or an RNA molecule.

In some embodiments, the CRISPR nuclease has full catalytic activity, is a nickase, or is catalytically inactive, and is fused to a DNA-interacting or a modifying protein. For example, the CRISPR nuclease may be fused to deaminase protein for use in base editing methods. In another example, the CRISPR nuclease may be fused to a reverse transcriptase for use in prime editing methods.

In some embodiments, the composition further comprises one or more RNA molecules, or a DNA polynucleotide encoding any one of the one or more RNA molecules, wherein the one or more RNA molecules and the CRISPR nuclease do not naturally occur together and the one or more RNA molecules are configured to form a complex with the CRISPR nuclease and/or target the complex to a target site.

In some embodiments, the CRISPR nuclease comprises a sequence having at least 90% identity to the amino acid sequence set forth in SEQ ID NO: 1 and at least one RNA molecule comprises a sequence selected from the group consisting of SEQ ID NOs: 4-36.

In some embodiments, the CRISPR nuclease comprises a sequence having at least 90% identity to the amino acid sequence set forth in SEQ ID NO: 1 and at least one RNA molecule is a CRISPR RNA (crRNA) molecule comprising a guide sequence portion and a sequence selected from the group consisting of SEQ ID NOs: 4-7 and 18-21.

In some embodiments, the composition further comprises a transactivating CRISPR RNA (tracrRNA) molecule comprising a sequence set forth in the group consisting of SEQ ID NOs: 8-14, 17, 22-28, and 32.

In some embodiments, the CRISPR nuclease comprises a sequence having at least 90% identity to the amino acid sequence set forth in SEQ ID NO: 1 and at least one RNA molecule is a single-guide RNA (sgRNA) molecule comprising a guide sequence portion and a sequence selected from the group consisting of SEQ ID NOs: 4-36.

In some embodiments, the CRISPR nuclease comprises a sequence having at least 90% identity to the amino acid sequence set forth in SEQ ID NO: 1 and at least one RNA molecule is a single-guide RNA (sgRNA) molecule comprising a guide sequence portion and a scaffold portion that is at least 79 nucleotides in length.

In some embodiments, the CRISPR nuclease is a nickase having an inactivated RuvC domain created by an amino acid substitution at a position provided for the CRISPR nuclease in column 5 of Table 1.

In some embodiments, the CRISPR nuclease is a nickase having an inactivated HNH domain created by an amino acid substitution at a position provided for the CRISPR nuclease in column 6 of Table 1.

In some embodiments, the CRISPR nuclease is a catalytically dead nuclease having an inactivated RuvC domain and an inactivated HNH domain created by substitutions at the positions provided for the CRISPR nuclease in column 7 of Table 1.

For example, a nickase may be generated for the OMNI-103 nuclease by inactivating its RuvC domain by substituting an aspartic acid residue (D) in position 12 of the amino acid sequence of OMNI-103 (SEQ ID NO: 1) for another amino acid e.g. alanine (A). Substitution to any other amino acid is permissible for each of the amino acid positions indicated in columns 5-7 of Table 1, except if the amino acid position is followed by an asterisk, which indicates that any substitution other than aspartic acid (D) to glutamic acid (E) or glutamic acid (E) or aspartic acid (D) results in inactivation. For example, a nickase may be generated for the OMNI-103 nuclease by inactivating its HNH domain by substituting an aspartic acid (D) in position 856 of the amino acid sequence of OMNI-103 (SEQ ID NO: 1) for an amino acid other than glutamic acid residue (E), e.g. for alanine (A). Other nickases or catalytically dead nucleases can be generated using the same notation in Table 1.

In some embodiments, the CRISPR nuclease is a nickase created by an amino acid substitution at position D12, E776, H988 or D991.

In some embodiments, the CRISPR nuclease is a nickase created by an amino acid substitution at position D856, H857 or N880, wherein an amino acid substitution at position D856 is a substitution other than aspartic acid (D) to glutamic acid (E).

In some embodiments, the CRISPR nuclease is a catalytically dead nuclease created by an amino acid substitution at any one of positions D12, E776, H988 or D991 and an amino acid substitution at any one of positions D856, H857 or N880, wherein an amino acid substitution at position D856 is a substitution other than aspartic acid (D) to glutamic acid (E).

In some embodiments, the CRISPR nuclease utilizes a protospacer adjacent motif (PAM) sequence provided for the CRISPR nuclease in column 2 or column 3 of Table 3.

The invention also provides a method for modifying a nucleotide sequence at a DNA target site in a cell-free system or the genome of a cell comprising introducing into the cell any one of the compositions described above. In some embodiments, the composition comprises a CRISPR nuclease and a crRNA:tracrRNA complex or a sgRNA molecule.

In some embodiments, the CRISPR nuclease effects a DNA break in a DNA strand adjacent to a protospacer adjacent motif (PAM) sequence provided for the CRISPR nuclease in column 2 or column 3 of Table 3, and effects a DNA break in a DNA strand adjacent to a sequence that is complementary to the PAM sequence. For example, the OMNI-103 nuclease with the appropriate targeting sgRNA or crRNA:tracrRNA complex is capable of forming a DNA break in strand adjacent to a NNRRHY, NNRACT, or NNRVCT sequence and in a DNA strand adjacent to a sequence that is complementary to a NNRRHY, NNRACT, or NNRVCT sequence. In some embodiments, the DNA strand is within a nucleus of a cell.

In some embodiments, the CRISPR nuclease is a nickase having an inactivated RuvC domain created by an amino acid substitution at a position provided for the CRISPR nuclease in column 5 of Table 1, and effects a DNA break in a DNA strand adjacent to a sequence that is complementary to the PAM sequence.

In some embodiments, the CRISPR nuclease is a nickase having an inactivated HNH domain created by an amino acid substitution at a position provided for the CRISPR nuclease in column 6 of Table 1, and effects a DNA break in a DNA strand adjacent to the PAM sequence.

In some embodiments, the CRISPR nuclease is a catalytically dead nuclease having an inactivated RuvC domain and an inactivated HNH domain created by substitutions at the positions provided for the CRISPR nuclease in column 7 of Table 1, and effects a DNA break in a DNA strand adjacent to the PAM sequence.

The invention also provides a method of modifying a nucleotide sequence at a DNA target site in a cell-free system or the genome of a cell comprising introducing into the cell any one of the compositions provided herein.

In some embodiments, the CRISPR nuclease comprises a sequence having at least 90% identity to the amino acid sequence set forth in SEQ ID NO: 1, wherein the CRISPR nuclease effects a DNA strand break adjacent to a NNRRHY, NNRACT, or NNRVCT protospacer adjacent motif (PAM) sequence, and/or effects a DNA strand break adjacent to a sequence that is complementary to the PAM sequence.

In some embodiments, the CRISPR nuclease is a nickase created by an amino acid substitution at position D12, E776, H988 or D991, and effects a DNA strand break adjacent to the PAM sequence.

In some embodiments, the CRISPR nuclease is a nickase created by an amino acid substitution at position D856, H857 or N880, and effects a DNA strand break adjacent to a sequence that is complementary to the PAM sequence, wherein an amino acid substitution at position D856 is a substitution other than aspartic acid (D) to glutamic acid (E).

In some embodiments, the cell is a eukaryotic cell or a prokaryotic cell.

In some embodiments, the cell is a mammalian cell.

In some embodiments, the cell is a human cell.

In some embodiments, the CRISPR nuclease comprises an amino acid sequence having at least 100%, 99%, 98%, 97%, 96%, 95%, 94%, 93%, 92%, 91%, 90%, 89%, 88%, 87%, 86%, 85%, 84%, 83%, or 82% amino acid sequence identity to a CRISPR nuclease as SEQ ID NO: 1. In an embodiment the sequence encoding the CRISPR nuclease has at least 100%, 99%, 98%, 97%, 96%, 95%, 94%, 93%, 92%, 91%, 90%, 89%, 88%, 87%, 86%, 85%, 84%, 83%, or 82% identity to a nucleic acid sequence selected from the group consisting of SEQ ID NOs: 2-3.

The invention also provides a non-naturally occurring composition comprising a CRISPR nuclease, wherein the CRISPR nuclease comprises an amino acid sequence corresponding to the amino acid sequence of at least one of Domain A, Domain B, Domain C, Domain D, Domain E, Domain F, Domain G, Domain H, Domain I, or Domain J of SEQ ID NO: 1, a) wherein Domain A comprises a sequence having at least 90%, 91%, 92%, 93%, 94%, 95%, 96%, 97%, 98%, 99%, or 100% identity to amino acids 1-45 of SEQ ID NO: 1;
b) wherein Domain B comprises a sequence having at least 90%, 91%, 92%, 93%, 94%, 95%, 96%, 97%, 98%, 99%, or 100% identity to amino acids 46-83 of SEQ ID NO: 1;
c) wherein Domain C comprises a sequence having at least 90%, 91%, 92%, 93%, 94%, 95%, 96%, 97%, 98%, 99%, or 100% identity to amino acids 84-158 of SEQ ID NO: 1;
d) wherein Domain D comprises a sequence having at least 90%, 91%, 92%, 93%, 94%, 95%, 96%, 97%, 98%, 99%, or 100% identity to amino acids 159-302 of SEQ ID NO: 1;
e) wherein Domain E comprises a sequence having at least 90%, 91%, 92%, 93%, 94%, 95%, 96%, 97%, 98%, 99%, or 100% identity to amino acids 303-515 of SEQ ID NO: 1;
f) wherein Domain F comprises a sequence having at least 90%, 91%, 92%, 93%, 94%, 95%, 96%, 97%, 98%, 99%, or 100% identity to amino acids 516-727 of SEQ ID NO: 1;
g) wherein Domain G comprises a sequence having at least 90%, 91%, 92%, 93%, 94%, 95%, 96%, 97%, 98%, 99%, or 100% identity to amino acids 728-778 of SEQ ID NO: 1;
h) wherein Domain H comprises a sequence having at least 90%, 91%, 92%, 93%, 94%, 95%, 96%, 97%, 98%, 99%, or 100% identity to amino acids 779-923 of SEQ ID NO: 1;
i) wherein Domain I comprises a sequence having at least 90%, 91%, 92%, 93%, 94%, 95%, 96%, 97%, 98%, 99%, or 100% identity to amino acids 924-1068 of SEQ ID NO: 1; and
j) wherein Domain J comprises a sequence having at least 90%, 91%, 92%, 93%, 94%, 95%, 96%, 97%, 98%, 99%, or 100% identity to amino acids 1069-1348 of SEQ ID NO: 1.

According to some aspects of the invention, the disclosed compositions comprise DNA constructs or a vector system comprising nucleotide sequences that encode the CRISPR nuclease or variant CRISPR nuclease. In some embodiments, the nucleotide sequence that encode the CRISPR nuclease or variant CRISPR nuclease is operably linked to a promoter that is operable in the cells of interest. In some embodiments, the cell of interest is a eukaryotic cell. In some embodiments the cell of interest is a mammalian cell. In some embodiments, the nucleic acid sequence encoding the engineered CRISPR nuclease is codon optimized for use in cells from a particular organism. In some embodiments, the nucleic acid sequence encoding the nuclease is codon optimized for *E. coli*. In some embodiments, the nucleic acid sequence encoding the nuclease is codon optimized for eukaryotic cells. In some embodiments, the nucleic acid sequence encoding the nuclease is codon optimized for mammalian cells.

In some embodiments, the composition comprises a recombinant nucleic acid, comprising a heterologous promoter operably linked to a polynucleotide encoding a CRISPR enzyme having at least 100%, 99%, 98%, 97%, 96%, 95%, 94%, 93%, 92%, 91%, 90% identity to SEQ ID NO: 1. Each possibility represents a separate embodiment.

In an embodiment of the composition, the CRISPR nuclease has at least 75%, 80%, 85, 90%, 95%, or 97% identity to the amino acid sequence as set forth in SEQ ID NO: 1 or the sequence encoding the CRISPR nuclease has at least a 75%, 80%, 85, 90%, 95%, or 97% sequence identity to a nucleotide sequence selected from the group consisting of SEQ ID NOs: 2 and 3.

According to some embodiments, there is provided an engineered or non-naturally occurring composition comprising a CRISPR nuclease comprising a sequence having at least 100%, 99%, 98%, 97%, 96%, 95%, 94%, 93%, 92%, 91%, 90%, 85%, 80% identity to the amino acid sequence of SEQ ID NO: 1 or a nucleic acid molecule comprising a sequence encoding the CRISPR nuclease. Each possibility represents a separate embodiment.

In an embodiment, the CRISPR nuclease is engineered or non-naturally occurring. The CRISPR nuclease may also be recombinant. Such CRISPR nucleases are produced using laboratory methods (e.g. molecular cloning) to bring together genetic material from multiple sources, creating sequences that would not otherwise be found in biological organisms.

In an embodiment, the CRISPR nuclease further comprises an RNA-binding portion capable of interacting with a DNA-targeting RNA molecule (gRNA) and an activity portion that exhibits site-directed enzymatic activity.

In an embodiment, the composition further comprises a DNA-targeting RNA molecule or a DNA polynucleotide encoding a DNA-targeting RNA molecule, wherein the DNA-targeting RNA molecule comprises a guide sequence portion, i.e. a nucleotide sequence that is complementary to a sequence in a target region, wherein the DNA-targeting RNA molecule and the CRISPR nuclease do not naturally occur together.

In an embodiment, the DNA-targeting RNA molecule further comprises a nucleotide sequence that can form a complex with a CRISPR nuclease.

This invention also provides a non-naturally occurring composition comprising a CRISPR associated system comprising:

a) one or more RNA molecules comprising a guide sequence portion linked to a direct repeat sequence, wherein the guide sequence is capable of hybridizing with a target sequence, or one or more nucleotide sequences encoding the one or more RNA molecules; and b) a CRISPR nuclease comprising an amino acid sequence having at least 95% identity to the amino acid sequence of SEQ ID NO: 1 or a nucleic acid molecule comprising a sequence encoding the CRISPR nuclease;

wherein the one or more RNA molecules hybridize to the target sequence, wherein the target sequence is adjacent to a Protospacer Adjacent Motif (PAM), and the one or more RNA molecules form a complex with the RNA-guided nuclease.

In an embodiment, the composition further comprises an RNA molecule comprising a nucleotide sequence that can form a complex with a CRISPR nuclease (e.g. a tracrRNA molecule) or a DNA polynucleotide comprising a sequence encoding an RNA molecule that can form a complex with the CRISPR nuclease.

In an embodiment, the composition further comprises a donor template for homology directed repair (HDR).

In an embodiment, the composition is capable of editing the target region in the genome of a cell.

According to some embodiments, there is provided a non-naturally occurring composition comprising:

(a) a CRISPR nuclease, or a polynucleotide encoding the CRISPR nuclease, comprising:

an RNA-binding portion; and an activity portion that exhibits site-directed enzymatic activity, wherein the CRISPR nuclease has at least 100%, 99%, 98%, 97%, 96%, 95%, 94%, 93%, 92%, 91%, 90%, 85%, 80% identity to SEQ ID NO: 1; and (b) one or more RNA molecules or a DNA polynucleotide encoding the one or more RNA molecules comprising:

i) a DNA-targeting RNA sequence, comprising a nucleotide sequence that is complementary to a sequence in a target DNA sequence; and ii) a protein-binding RNA sequence, capable of interacting with the RNA-binding portion of the CRISPR nuclease, wherein the DNA targeting RNA sequence and the CRISPR nuclease do not naturally occur together. Each possibility represents a separate embodiment.

In some embodiments, there is provided a single RNA molecule comprising the DNA-targeting RNA sequence and the protein-binding RNA sequence, wherein the RNA molecule can form a complex with the CRISPR nuclease and serve as the DNA targeting module. In some embodiments, the RNA molecule has a length of up to 1000 bases, 900 bases, 800 bases, 700 bases, 600 bases, 500 bases, 400 bases, 300 bases, 200 bases, 100 bases, 50 bases. Each possibility represents a separate embodiment. In some embodiments, a first RNA molecule comprising the DNA-targeting RNA sequence and a second RNA molecule comprising the protein-binding RNA sequence interact by base pairing or alternatively fused together to form one or more RNA molecules that complex with the CRISPR nuclease and serve as the DNA targeting module.

This invention also provides a non-naturally occurring composition comprising:

a) a CRISPR nuclease comprising a sequence having at least 95% identity to the amino acid sequence of SEQ ID NOs: 1 or a nucleic acid molecule comprising a sequence encoding the CRISPR nuclease; and b) one or more RNA molecules, or one or more DNA polynucleotide encoding the one or more RNA molecules, comprising at least one of:

i) a nuclease-binding RNA nucleotide sequence capable of interacting with/binding to the CRISPR nuclease; and ii) a DNA-targeting RNA nucleotide sequence comprising a sequence complementary to a sequence in a target DNA sequence, wherein the CRISPR nuclease is capable of complexing with the one or more RNA molecules to form a complex capable of hybridizing with the target DNA sequence.

In an embodiment, the CRISPR nuclease and the one or more RNA molecules form a CRISPR complex that is capable of binding to the target DNA sequence to effect cleavage of the target DNA sequence.

In an embodiment, the CRISPR nuclease and at least one of the one or more RNA molecules do not naturally occur together.

In an embodiment:

a) the CRISPR nuclease comprises an RNA-binding portion and an activity portion that exhibits site-directed enzymatic activity;

b) the DNA-targeting RNA nucleotide sequence comprises a nucleotide sequence that is complementary to a sequence in a target DNA sequence; and c) the nuclease-binding RNA nucleotide sequence comprises a sequence that interacts with the RNA-binding portion of the CRISPR nuclease.

In an embodiment, the nuclease-binding RNA nucleotide sequence and the DNA-targeting RNA nucleotide sequence are on a single guide RNA molecule (sgRNA), wherein the sgRNA molecule can form a complex with the CRISPR nuclease and serve as the DNA targeting module.

In an embodiment, the nuclease-binding RNA nucleotide sequence is on a first RNA molecule and the DNA-targeting RNA nucleotide sequence is on a second RNA molecule, and wherein the first and second RNA molecules interact by base-pairing or are fused together to form a RNA complex or sgRNA that forms a complex with the CRISPR nuclease and serves as a DNA targeting module.

In an embodiment, the sgRNA has a length of up to 1000 bases, 900 bases, 800 bases, 700 bases, 600 bases, 500 bases, 400 bases, 300 bases, 200 bases, 100 bases, 50 bases.

In an embodiment, the composition further comprises a donor template for homology directed repair (HDR).

In an embodiment, the CRISPR nuclease is non-naturally occurring.

In an embodiment, the CRISPR nuclease is engineered and comprises unnatural or synthetic amino acids.

In an embodiment, the CRISPR nuclease is engineered and comprises one or more of a nuclear localization sequences (NLS), cell penetrating peptide sequences, and/or affinity tags.

In an embodiment, the CRISPR nuclease comprises one or more nuclear localization sequences of sufficient strength to drive accumulation of a CRISPR complex comprising the CRISPR nuclease in a detectable amount in the nucleus of a eukaryotic cell.

This invention also provides a method of modifying a nucleotide sequence at a target site in a cell-free system or the genome of a cell comprising introducing into the cell any of the compositions of the invention.

In an embodiment, the cell is a eukaryotic cell.

In another embodiment, the cell is a prokaryotic cell.

In some embodiments, the one or more RNA molecules further comprises an RNA sequence comprising a nucleotide molecule that can form a complex with the RNA nuclease (tracrRNA) or a DNA polynucleotide encoding an RNA molecule comprising a nucleotide sequence that can form a complex with the CRISPR nuclease.

In an embodiment, the CRISPR nuclease comprises 1, 2, 3, 4, 5, 6, 7, 8, 9, 10, or more NLSs at or near the amino-terminus, 1, 2, 3, 4, 5, 6, 7, 8, 9, 10, or more NLSs at or near carboxy-terminus, or a combination of 1, 2, 3, 4, 5, 6, 7, 8, 9, 10, or more NLSs at or near the amino-terminus and 1, 2, 3, 4, 5, 6, 7, 8, 9, 10, or more NLSs at or near carboxy-terminus. In an embodiment 1-4 NLSs are fused with the CRISPR nuclease. In an embodiment, an NLS is located within the open-reading frame (ORF) of the CRISPR nuclease.

Methods of fusing an NLS at or near the amino-terminus, at or near carboxy-terminus, or within the ORF of an expressed protein are well known in the art. As an example, to fuse an NLS to the amino-terminus of a CRISPR nuclease, the nucleic acid sequence of the NLS is placed immediately after the start codon of the CRISPR nuclease on the nucleic acid encoding the NLS-fused CRISPR nuclease. Conversely, to fuse an NLS to the carboxy-terminus of a CRISPR nuclease the nucleic acid sequence of the NLS is placed after the codon encoding the last amino acid of the CRISPR nuclease and before the stop codon.

Any combination of NLSs, cell penetrating peptide sequences, and/or affinity tags at any position along the ORF of the CRISPR nuclease is contemplated in this invention.

The amino acid sequences and nucleic acid sequences of the CRISPR nucleases provided herein may include NLS and/or TAGs inserted so as to interrupt the contiguous amino acid or nucleic acid sequences of the CRISPR nucleases.

In an embodiment, the one or more NLSs are in tandem repeats.

In an embodiment, the one or more NLSs are considered in proximity to the N- or C-terminus when the nearest amino acid of the NLS is within about 1, 2, 3, 4, 5, 10, 15, 20, 25, 30, 40, 50, or more amino acids along the polypeptide chain from the N- or C-terminus.

As discussed, the CRISPR nuclease may be engineered to comprise one or more of a nuclear localization sequences (NLS), cell penetrating peptide sequences, and/or affinity tags.

In an embodiment, the composition further comprises a recombinant nucleic acid molecule comprising a heterologous promoter operably linked to the nucleotide acid molecule comprising the sequence encoding the CRISPR nuclease.

In an embodiment, the CRISPR nuclease or nucleic acid molecule comprising a sequence encoding the CRISPR nuclease is non-naturally occurring or engineered.

This invention also provides a non-naturally occurring or engineered composition comprising a vector system comprising the nucleic acid molecule comprising a sequence encoding any of the CRISPR nucleases of the invention.

This invention also provides use of any of the compositions of the invention for the treatment of a subject afflicted with a disease associated with a genomic mutation comprising modifying a nucleotide sequence at a target site in the genome of the subject.

This invention provides a method of modifying a nucleotide sequence at a target site in the genome of a mammalian cell comprising introducing into the cell (i) a composition comprising a CRISPR nuclease having at least 95% identity to an amino acid sequence of SEQ ID NO: 1 or a nucleic acid molecule comprising a sequence encoding a CRISPR nuclease which sequence has at least 95% identity to a nucleic acid sequence of SEQ ID NOs: 2-3 and (ii) a DNA-targeting RNA molecule, or a DNA polynucleotide encoding a DNA-targeting RNA molecule, comprising a nucleotide sequence that is complementary to a sequence in the target DNA.

In some embodiments, the method is performed ex vivo. In some embodiments, the method is performed in vivo. In some embodiments, some steps of the method are performed ex vivo and some steps are performed in vivo. In some embodiments the mammalian cell is a human cell.

In an embodiment, the method further comprises introducing into the cell: (iii) an RNA molecule comprising a tracrRNA sequence or a DNA polynucleotide encoding an RNA molecule comprising a tracrRNA sequence.

In an embodiment, the DNA-targeting RNA molecule comprises a crRNA repeat sequence.

In an embodiment, the RNA molecule comprising a tracrRNA sequence is able to bind the DNA-targeting RNA molecule.

In an embodiment, the DNA-targeting RNA molecule and the RNA molecule comprising a tracrRNA sequence interact to form an RNA complex, and the RNA complex is capable of forming an active complex with the CRISPR nuclease.

In an embodiment, the DNA-targeting RNA molecule and the RNA molecule comprising a nuclease-binding RNA sequence are fused in the form of a single guide RNA molecule that is suitable to form an active complex with the CRISPR nuclease.

In an embodiment, the guide sequence portion comprises a sequence complementary to a protospacer sequence.

In an embodiment, the CRISPR nuclease forms a complex with the DNA-targeting RNA molecule and effects a double strand break in a region that is 3' or 5' of a Protospacer Adjacent Motif (PAM).

In an embodiment of any of the methods described herein, the method is for treating a subject afflicted with a disease associated with a genomic mutation comprising modifying a nucleotide sequence at a target site in the genome of the subject.

In an embodiment, the method comprises first selecting a subject afflicted with a disease associated with a genomic mutation and obtaining the cell from the subject.

This invention also provides a modified cell or cells obtained by any of the methods described herein. In an embodiment these modified cell or cells are capable of giving rise to progeny cells. In an embodiment these modified cell or cells are capable of giving rise to progeny cells after engraftment.

This invention also provides a composition comprising these modified cells and a pharmaceutically acceptable carrier. Also provided is an in vitro or ex vivo method of preparing this, comprising mixing the cells with the pharmaceutically acceptable carrier.

The invention also provides a composition comprising a non-naturally occurring RNA molecule, the RNA molecule comprising a crRNA repeat sequence portion and a guide sequence portion, wherein the RNA molecule forms a complex with and targets an OMNI-103 nuclease to a DNA target site in the presence of a tracrRNA sequence, wherein the tracrRNA sequence is encoded by a tracrRNA portion of the RNA molecule or a tracrRNA portion of a second RNA molecule.

In some embodiments, the crRNA repeat sequence portion is up to 17 nucleotides in length, preferably 14-17 nucleotides in length.

In some embodiments, the crRNA repeat sequence portion has at least 60-70%, 71-80%, 81-90%, 91-95%, or 96-99% sequence identity to SEQ ID NOs: 114 or 115.

In some embodiments, the crRNA repeat sequence portion has at least 95% sequence identity to any one of SEQ ID NOs: 114 or 115.

In some embodiments, the crRNA repeat sequence is other than SEQ ID NO: 115.

In some embodiments, the RNA molecule comprising the crRNA repeat sequence portion and the guide sequence portion further comprises the tracrRNA portion.

In some embodiments, the crRNA repeat sequence portion is covalently linked to the tracrRNA portion by a polynucleotide linker portion.

In some embodiments, the composition comprises a second RNA molecule comprising the tracrRNA portion.

In some embodiments, the OMNI-103 nuclease has at least 95% sequence identity to the amino acid sequence of SEQ ID NO: 1.

In some embodiments, the guide sequence portion is 17-30 nucleotides in length, preferably 22 nucleotides in length.

The invention also provides a composition comprising a non-naturally occurring RNA molecule, the RNA molecule comprising a tracrRNA portion, wherein the RNA molecule forms a complex with and targets an OMNI-103 nuclease to a DNA target site in the presence of a crRNA repeat sequence portion and a guide sequence portion, wherein the crRNA repeat sequence portion and the guide sequence portion are encoded by the RNA molecule or a second RNA molecule.

In some embodiments, the tracrRNA portion is less than 85 nucleotides in length, preferably 84-80, 79-75, 74-70, 69-65, or 64-60 nucleotides in length.

In some embodiments, the tracrRNA portion has at least 30-40%, 41-50%, 51-60%, 61-70%, 71-80%, 81-90%, 91-95%, or 96-99% sequence identity to the tracrRNA portion of any one of SEQ ID NOs: 109-113.

In some embodiments, the tracrRNA portion has at least 95% sequence identity to the tracrRNA portions of any one of SEQ ID NOs: 109-113.

In some embodiments, the tracrRNA portion is other than the tracr portion of SEQ ID NO: 15 or 16.

In some embodiments, the tracrRNA portion comprises a tracrRNA anti-repeat sequence portion that is up to 19 nucleotides in length, preferably 16-19 nucleotides in length.

In some embodiments, the tracrRNA portion comprises a tracrRNA anti-repeat sequence portion that has at least 60-70%, 71-80%, 81-90%, 91-95%, or 96-99% sequence identity to any one of SEQ ID NOs: 116 or 117.

In some embodiments, the tracrRNA portion comprises a tracrRNA anti-repeat sequence portion that has at least 95% sequence identity to any one of SEQ ID NOs: 116 or 117.

In some embodiments, the tracrRNA portion comprises a tracrRNA anti-repeat sequence portion having a sequence other than SEQ ID NO: 117.

In some embodiments, the RNA molecule comprises a tracrRNA portion and further comprises a crRNA repeat sequence portion and a guide sequence portion.

In some embodiments, the tracrRNA portion is covalently linked to the crRNA repeat sequence by a polynucleotide linker portion.

In some embodiments, the polynucleotide linker portion is 4-10 nucleotides in length.

In some embodiments, the polynucleotide linker has a sequence of GAAA.

In some embodiments, the composition further comprises a second RNA molecule comprising a crRNA repeat sequence portion and a guide sequence portion.

In some embodiments, the OMNI-103 nuclease is at least 95% sequence identity to the amino acid sequence of SEQ ID NO: 1.

In some embodiments, the guide sequence portion is 17-30 nucleotides in length, preferably 22 nucleotides in length.

The invention also provides a composition comprising a non-naturally occurring RNA molecule, the RNA molecule comprising an RNA scaffold portion, the RNA scaffold portion having the structure:

crRNA repeat sequence portion-tracrRNA portion;

wherein the RNA scaffold portion forms a complex with and targets an OMNI-103 CRISPR nuclease to a DNA target site having complementarity to a guide sequence portion of the RNA molecule.

In some embodiments, the OMNI-103 nuclease has at least 95% sequence identity to the amino acid sequence of SEQ ID NO: 1.

In some embodiments, the RNA scaffold portion is 110-105, 104-100, 99-95, 94-90, 89-85, 84-80, 79-75, or 74-70 nucleotides in length.

In some embodiments, the RNA scaffold portion is 107, 101, 95, 85, or 79 nucleotides in length.

In some embodiments, the RNA scaffold portion has at least 30%, at least 40%, at least 50%, at least 60%, at least 70%, at least 80%, at least 85%, at least 90%, or at least 95% sequence identity to any one of SEQ ID NOs: 109-113.

In some embodiments, the crRNA repeat sequence portion is up to 17 nucleotides in length, preferably 14-17 nucleotides in length.

In some embodiments, the crRNA repeat sequence portion has at least 60-70%, 71-80%, 81-90%, 91-95%, or 96-99% sequence identity to SEQ ID NOs: 114 or 115.

In some embodiments, the crRNA repeat sequence portion has at least 95% sequence identity to any one of SEQ ID NOs: 114 or 115.

In some embodiments, the crRNA repeat sequence is other than SEQ ID NO: 23.

In some embodiments, the tracrRNA portion is less than 85 nucleotides in length, preferably 84-80, 79-75, 74-70, 69-65, or 64-60 nucleotides in length.

In some embodiments, the tracrRNA portion has at least 30-40%, 41-50%, 51-60%, 61-70%, 71-80%, 81-90%, 91-95%, or 96-99% sequence identity to the tracrRNA portion of any one of SEQ ID NOs: 109-113.

In some embodiments, the tracrRNA portion has at least 95% sequence identity to the tracrRNA portions of any one of SEQ ID NOs: 109-113.

In some embodiments, the tracrRNA portion is other than the tracrRNA portion of SEQ ID NO: 15 or 16.

In some embodiments, the RNA scaffold portion further comprises a linker portion between the crRNA repeat sequence portion and the tracrRNA portion such that the RNA scaffold has the structure:

crRNA repeat sequence portion-linker portion-tracrRNA portion.

In some embodiments, the tracrRNA portion comprises a tracrRNA anti-repeat sequence portion, wherein the crRNA repeat sequence and the tracrRNA anti-repeat sequence portion are covalently linked by the linker portion.

In some embodiments, the linker portion is a polynucleotide linker that is 4-10 nucleotides in length.

In some embodiments, the polynucleotide linker has a sequence of GAAA.

In some embodiments, the tracrRNA portion comprises a tracrRNA anti-repeat sequence portion that is up to 19 nucleotides in length, preferably 16-19 nucleotides in length.

In some embodiments, the tracrRNA portion comprises a tracrRNA anti-repeat sequence portion that has at least 60-70%, 71-80%, 81-90%, 91-95%, or 96-99% sequence identity to any one of SEQ ID NOs: 116 or 117.

In some embodiments, the tracrRNA portion comprises a tracrRNA anti-repeat sequence portion that has at least 95% sequence identity to any one of SEQ ID NOs: 116 or 117.

In some embodiments, the tracrRNA anti-repeat sequence is other than SEQ ID NO: 117.

In some embodiments, the tracrRNA portion comprises a first section of nucleotides linked to the tracrRNA anti-repeat portion, and the first section of nucleotides has at least 95% sequence identity to any one of SEQ ID NOs: 118-120.

In some embodiments, the tracrRNA portion comprises a second section of nucleotides linked to a first section of nucleotides, and the second section of nucleotides has at least 95% sequence identity to any one of SEQ ID NOs: 121-124.

In some embodiments, the RNA scaffold portion has at least 95% identity to the nucleotide sequence of any one of SEQ ID NOs: 109-113.

In some embodiments, the RNA scaffold portion has a predicted structure of any one of the V2, V2.1, V2.2, V2.3, V2.4, or V2.5 RNA scaffolds.

In some embodiments, the RNA scaffold portion has a sequence other than SEQ ID NO: 15 or 16.

In some embodiments, a guide sequence portion is covalently linked to the crRNA repeat sequence portion of the RNA molecule, forming a single-guide RNA molecule having a structure:

guide sequence portion-crRNA repeat sequence portion-tracrRNA portion.

In some embodiments, the guide sequence portion is 17-30 nucleotides, more preferably 20-23 nucleotides, more preferably 22 nucleotides in length.

In some embodiments, the composition further comprises an OMNI-103 CRISPR nuclease, wherein the OMNI-103 CRISPR nuclease has at least 95% identity to the amino acid sequence of SEQ ID NO: 1.

In some embodiments, the RNA molecule is formed by in vitro transcription (IVT) or solid-phase artificial oligonucleotide synthesis.

In some embodiments, the RNA molecule comprises modified nucleotides.

The invention also provides a polynucleotide molecule encoding the RNA molecule of any one of the above embodiments.

The invention also provides a method of modifying a nucleotide sequence at a DNA target site in a cell-free system or a genome of a cell comprising introducing into the system or cell any one of the RNA molecules presented herein and a CRISPR nuclease having at least 95% sequence identity to the amino acid sequence of SEQ ID NO: 1.

In some embodiments, the cell is a eukaryotic cell or a prokaryotic cell.

In some embodiments, the eukaryotic cell is a human cell or a plant cell.

The invention also provides a kit for modifying a nucleotide sequence at a DNA target site in a cell-free system or a genome of a cell comprising introducing into the system or cell the composition of any one of the above embodiments, a CRISPR nuclease having at least 95% sequence identity to the amino acid sequence of SEQ ID NO: 1, and instructions for delivering the RNA molecule and the CRISPR nuclease to the cell.

In embodiments of the present invention, the non-naturally occurring RNA molecule comprises a "spacer" or "guide sequence" portion. The "spacer portion" or "guide sequence portion" of an RNA molecule refers to a nucleotide sequence that is capable of hybridizing to a specific target DNA sequence, e.g., the guide sequence portion has a nucleotide sequence which is fully complementary to the DNA sequence being targeted along the length of the guide sequence portion. In some embodiments, the guide sequence portion is 17, 18, 19, 20, 21, 22, 23, 24, 25, 26, 27, 28, 29, or 30 nucleotides in length, or approximately 17-30, 17-29, 17-28, 17-27, 17-26, 17-25, 17-24, 18-22, 19-22, 18-20, 17-20, or 21-22 nucleotides in length. Preferably, the entire length of the guide sequence portion is fully complementary to the DNA sequence being targeted along the length of the guide sequence portion. The guide sequence portion may be part of an RNA molecule having a "scaffold portion" that can form a complex with and activate a CRISPR nuclease, with the guide sequence portion of the RNA molecule serving as the DNA targeting portion of the CRISPR complex. When the RNA molecule having a scaffold portion and a guide sequence portion is present contemporaneously with the CRISPR molecule, the RNA molecule is capable of targeting the CRISPR nuclease to the specific target DNA sequence. Each possibility represents a separate embodiment. The RNA molecule spacer portion can be custom designed to target any desired sequence.

In an embodiment, the nuclease-binding RNA nucleotide sequence and the DNA-targeting RNA nucleotide sequence (e.g. spacer or guide sequence portion) are on a single-guide RNA molecule (sgRNA), wherein the sgRNA molecule can form a complex with the OMNI-103 CRISPR nuclease and serve as the DNA targeting module.

In an embodiment, the nuclease-binding RNA nucleotide sequence is on a first RNA molecule and the DNA-targeting RNA nucleotide sequence is on a second RNA molecule, and the first and second RNA molecules interact by base-pairing and complex with the CRISPR nuclease to serve as the targeting module.

According to some aspects of the invention, the disclosed methods comprise a method of modifying a nucleotide sequence at a target site in a cell-free system or the genome of a cell comprising introducing into the cell the composition of any one of the embodiments described herein.

This invention also provides use of any of the compositions or methods of the invention for modifying a nucleotide sequence at a DNA target site in a cell.

This invention provides a method of modifying a nucleotide sequence at a target site in the genome of a eukaryotic cell.

This invention provides a method of modifying a nucleotide sequence at a target site in the genome of a mammalian cell. In some embodiments, the mammalian cell is a human cell.

This invention provides a method of modifying a nucleotide sequence at a target site in the genome of a plant cell.

In some embodiments, the method is performed ex vivo. In some embodiments, the method is performed in vivo. In some embodiments, some steps of the method are performed ex vivo and some steps are performed in vivo. In some embodiments the mammalian cell is a human cell.

This invention also provides a modified cell or cells obtained by any of the methods described herein. In an embodiment these modified cell or cells are capable of giving rise to progeny cells. In an embodiment these modified cell or cells are capable of giving rise to progeny cells after engraftment.

This invention also provides a composition comprising these modified cells and a pharmaceutically acceptable carrier. Also provided is an in vitro or ex vivo method of preparing this, comprising mixing the cells with the pharmaceutically acceptable carrier.

This invention also provides a kit for modifying a nucleotide sequence at a DNA target site in a cell-free system or a genome of a cell comprising introducing into the system or cell a CRISPR nuclease having at least 95% sequence identity to the amino acid sequence of SEQ ID NO: 1, one or more RNA molecules configured to form a complex with the CRISPR nuclease and/or target the complex to a target site, and instructions for delivering the RNA molecule and the CRISPR nuclease to the cell. For example, the kit may be used as a diagnostic kit to detect the presence of a target site (e.g. a DNA sequence) in a nucleotide molecule in a cell or in a test tube.

DNA-Targeting RNA Molecules

The "guide sequence portion" of an RNA molecule refers to a nucleotide sequence that is capable of hybridizing to a specific target DNA sequence, e.g., the guide sequence portion has a nucleotide sequence which is partially or fully complementary to the DNA sequence being targeted along the length of the guide sequence portion. In some embodiments, the guide sequence portion is 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 nucleotides in length, or approximately 17-50, 17-49, 17-48, 17-47, 17-46, 17-45, 17-44, 17-43, 17-42, 17-41, 17-40, 17-39, 17-38, 17-37, 17-36, 17-35, 17-34, 17-33, 17-31, 17-30, 17-29, 17-28, 17-27, 17-26, 17-25, 17-24, 17-22, 17-21, 18-25, 18-24, 18-23, 18-22, 18-21, 19-25, 19-24, 19-23, 19-22, 19-21, 19-20, 20-22, 18-20, 20-21, 21-22, or 17-20 nucleotides in length. The entire length of the guide sequence portion is fully complementary to the DNA sequence being targeted along the length of the guide sequence portion. The guide sequence portion may be part of an RNA molecule that can form a complex with a CRISPR nuclease with the guide sequence portion serving as the DNA targeting portion of the CRISPR complex. When the DNA molecule having the guide sequence portion is present contemporaneously with the CRISPR molecule the RNA molecule is capable of targeting the CRISPR nuclease to the specific target DNA sequence. Each possibility represents a separate embodiment. An RNA molecule can be custom designed to target any desired sequence. Accordingly, a molecule comprising a "guide sequence portion" is a type of targeting molecule. Throughout this application, the terms "guide molecule," "RNA guide molecule," "guide RNA molecule," and "gRNA molecule" are synonymous with a molecule comprising a guide sequence portion, and the term "spacer" is synonymous with a "guide sequence portion.

In embodiments of the present invention, the CRISPR nuclease has its greatest cleavage activity when used with an RNA molecule comprising a guide sequence portion having 17, 18, 19 20, 21, 22, 23, 24, 25, 26, 27, 28, 29, or 30 nucleotides.

A single-guide RNA (sgRNA) molecule may be used to direct a CRISPR nuclease to a desired target site. The single-guide RNA comprises a guide sequence portion as well as a scaffold portion. The scaffold portion interacts with a CRISPR nuclease and, together with a guide sequence portion, activates and targets the CRISPR nuclease to a desired target site. A scaffold portion may be further engineered, for example, to have a reduced size. For example, OMNI-103 CRIPSR nuclease demonstrates on-target nuclease activity with a sgRNA molecule having an engineered scaffold portion that is only 79 nucleotides in length.

According to some aspects of the invention, the disclosed methods comprise a method of modifying a nucleotide sequence at a target site in a cell-free system or the genome of a cell comprising introducing into the cell the composition of any one of the embodiments described herein.

In some embodiments, the cell is a eukaryotic cell, preferably a mammalian cell or a plant cell.

According to some aspects of the invention, the disclosed methods comprise a use of any one of the compositions described herein for the treatment of a subject afflicted with a disease associated with a genomic mutation comprising modifying a nucleotide sequence at a target site in the genome of the subject.

According to some aspects of the invention, the disclosed methods comprise a method of treating subject having a mutation disorder comprising targeting any one of the compositions described herein to an allele associated with the mutation disorder.

In some embodiments, the mutation disorder is related to a disease or disorder selected from any of a neoplasia, age-related macular degeneration, schizophrenia, neurological, neurodegenerative, or movement disorder, Fragile X Syndrome, secretase-related disorders, prion-related disorders, ALS, addiction, autism, Alzheimer's Disease, neutropenia, inflammation-related disorders, Parkinson's Disease, blood and coagulation diseases and disorders, beta thalassemia, sickle cell anemia, cell dysregulation and oncology diseases and disorders, inflammation and immune-related diseases and disorders, metabolic, liver, kidney and protein diseases and disorders, muscular and skeletal diseases and disorders, dermatological diseases and disorders, neurological and neuronal diseases and disorders, and ocular diseases and disorders.

OMNI CRISPR Nuclease Domains

The characteristic targeted nuclease activity of a CRISPR nuclease is imparted by the various functions of its specific domains. In this application the OMNI-103 CRISPR nuclease domains are defined as Domain A, Domain B, Domain C, Domain D, Domain E, Domain F, Domain G, Domain H, Domain I, and Domain J.

The activity of each OMNI-103 CRISPR nuclease domain is described herein, with each domain activity providing aspects of the advantageous features of the nuclease.

Specifically, Domain A, Domain G, and Domain I form a structural unit of the OMNI CRISPR nuclease, which contains a nuclease active site that participates in DNA strand cleavage. The structural unit formed by Domain A, Domain G, and Domain I cleaves a DNA strand that is displaced by a guide RNA molecule binding at a double-stranded DNA target site.

Domain B is involved in initiating DNA cleavage activity upon the binding of the OMNI CRISPR nuclease to a target a DNA site.

Domain C, Domain D, Domain E, and Domain F bind a guide RNA molecule and participate in providing specificity for target site recognition.

Domain H contains a nuclease active site that participates in DNA strand cleavage. Domain H cleaves a DNA strand which a guide RNA molecule binds at a DNA target site.

Domain J is involved in providing PAM site specificity to the OMNI CRISPR nuclease, including aspects of PAM site interrogation and recognition. Domain J also performs topoisomerase activity.

Further description of other CRISPR nuclease domains and their general functions can be found in, inter alia, Mir et al., ACS Chem. Biol. (2019), Palermo et al., Quarterly Reviews of Biophysics (2018), Jiang and Doudna, Annual Review of Biophysics (2017), Nishimasu et al., Cell (2014) and Nishimasu et al., Cell (2015), incorporated herein by reference.

In one aspect of the invention, an amino acid sequence having similarity to an OMNI CRISPR nuclease domain may be utilized in the design and manufacture of a non-naturally occurring peptide, e.g. a CRISPR nuclease, such that the peptide displays the advantageous features of the OMNI CRISPR nuclease domain activity.

In an embodiment, such a peptide, e.g. a CRISPR nuclease, comprises an amino acid sequence that has at least 100%, 99.5%, 99%, 98%, 97%, 96%, 95%, 94%, 93%, 92%, 91%, 90%, 89%, 88%, 87%, 86%, 85%, 84%, 83%, 82%, 81%, 80%, 79%, 78%, 77%, 76%, 75%, 74%, 73%, 72%, 71%, or 70% identity to the amino acid sequence of at least one of Domain A, Domain B, Domain C, Domain D, Domain E, Domain F, Domain G, Domain H, Domain I, or Domain J of the OMNI-103 CRISPR nuclease. In some embodiments, the peptide comprises at least one, at least two, at least three, at least four, at least five, at least six, at least seven, at least eight, at least nine, at least ten, or at least eleven amino acid sequences selected from the amino acid sequences having at least 100%, 99.5%, 99%, 98%, 97%, 96%, 95%, 94%, 93%, 92%, 91%, 90%, 89%, 88%, 87%, 86%, 85%, 84%, 83%, 82%, 81%, 80%, 79%, 78%, 77%, 76%, 75%, 74%, 73%, 72%, 71%, or 70% identity to the amino acid sequences of Domain A, Domain B, Domain C, Domain D, Domain E, Domain F, Domain G, Domain H, Domain I, and Domain J of the OMNI-103 CRISPR nuclease. Each possibility represents a separate embodiment. In an embodiment, the peptide exhibits extensive amino acid variability relative to the full length OMNI-103 CRISPR nuclease amino acid sequence outside of an amino acid sequence having at least 100%, 99.5%, 99%, 98%, 97%, 96%, 95%, 94%, 93%, 92%, 91%, 90%, 89%, 88%, 87%, 86%, 85%, 84%, 83%, 82%, 81%, 80%, 79%, 78%, 77%, 76%, 75%, 74%, 73%, 72%, 71%, or 70% identity to the amino acid sequence of at least one of Domain A, Domain B, Domain C, Domain D, Domain E, Domain F, Domain G, Domain H, Domain I, or Domain J of the OMNI-103 CRISPR nuclease. In an embodiment, the peptide comprises an intervening amino acid sequence between two domain sequences. In an embodiment, the intervening amino acid sequence is 1-10, 10-20, 20-40, 40-50, 50-60, 80-100, 100-150, 150-200, 200-250, up to 100, up to 200 or up to 300 amino acids in length. Each possibility represents a separate embodiment. In an embodiment, the intervening sequence is a linker sequence. In an embodiment, a CRISPR nuclease comprises multiple domains from an OMNI CRISPR nuclease, and the domains are preferably organized in alphabetical order from the N-terminus to the C-terminus of the CRISPR nuclease. For example, a CRISPR nuclease comprising Domain A, Domain E, and Domain I of OMNI-103, the order of those domains in the CRISPR nuclease sequence would be Domain A, Domain E, and finally Domain I, with the possibility of intervening sequences on either end or both ends of each domain.

In one aspect of the invention, an amino acid sequence encoding any one of the domains of an OMNI CRISPR nuclease described herein may comprise one or more amino acid substitutions relative to the original OMNI CRISPR nuclease domain sequence. The amino acid substitution may be a conservative substitution, i.e. substitution for an amino acid having similar chemical properties as the original amino acid. For example, a positively charged amino acid may be substituted for an alternate positively charged amino acid, e.g. an arginine residue may be substituted for a lysine residue, or a polar amino acid may be substituted for a different polar amino acid. Conservative substitutions are more tolerable, and the amino acid sequence encoding any one of the domains of the OMNI CRISPR nuclease may contain as many as 10% of such substitutions. The amino acid substitution may be a radical substitution, i.e. substitution for an amino acid having different chemical properties as the original amino acid. For example, a positively charged amino acid may be substituted for a negatively charged amino acid, e.g. an arginine residue may be substituted for a glutamic acid residue, or a polar amino acid may be substituted for a non-polar amino acid. The amino acid substitution may be a semi-conservative substitution, or the amino acid substitution may be to any other amino acid. The substitution may alter the activity relative to the original OMNI CRISPR nuclease domain function e.g. reduce catalytic nuclease activity.

According to some aspects of the invention, the disclosed compositions comprise a non-naturally occurring composition comprising a CRISPR nuclease, wherein the CRISPR nuclease comprises an amino acid sequence corresponding to the amino acid sequence of at least one of Domain A, Domain B, Domain C, Domain D, Domain E, Domain F, Domain G, Domain H, Domain I, or Domain J of the OMNI-103 CRISPR nuclease. The amino acid range of each domain within its respective OMNI CRISPR nuclease amino acid sequence is provided in Supplemental Table 1. In some embodiments of the invention, the CRISPR nuclease comprises at least one, at least two, at least three, at least four, or at least five amino acid sequences, wherein each amino acid sequence corresponds to any one of the amino acid sequences Domain A, Domain B, Domain C, Domain D, Domain E, Domain F, Domain G, Domain H, Domain I, or Domain J of the OMNI-103 CRISPR nuclease. Accordingly, the CRISPR nuclease may include any combination of amino acid sequences that corresponds to any of Domain A, Domain B, Domain C, Domain D, Domain E, Domain F, Domain G, Domain H, Domain I, or Domain J of the OMNI CRISPR nuclease. In some embodiments, the amino acid sequence is at least 100-250, 250-500, 500-1000, 1000-1500, 1000-1700, or 1000-2000 amino acids in length.

Diseases and Therapies

Certain embodiments of the invention target a nuclease to a specific genetic locus associated with a disease or disorder as a form of gene editing, method of treatment, or therapy. For example, to induce editing or knockout of a gene, a novel nuclease disclosed herein may be specifically targeted to a pathogenic mutant allele of the gene using a custom designed guide RNA molecule. The guide RNA molecule is preferably designed by first considering the PAM requirement of the nuclease, which as shown herein is also dependent on the system in which the gene editing is being performed. For example, a guide RNA molecule designed to target an OMNI-103 nuclease to a target site is designed to contain a spacer region complementary to a DNA strand of a DNA double-stranded region that neighbors a OMNI-103 PAM sequence, e.g. "NNRRHY" or "NNRACT" or "NNRVCT." The guide RNA molecule is further preferably designed to contain a spacer region (i.e. the region of the guide RNA molecule having complementarity to the target allele) of sufficient and preferably optimal length in order to increase specific activity of the nuclease and reduce off-target effects.

As a non-limiting example, the guide RNA molecule may be designed to target the nuclease to a specific region of a mutant allele, e.g. near the start codon, such that upon DNA damage caused by the nuclease a non-homologous end joining (NHEJ) pathway is induced and leads to silencing of the mutant allele by introduction of frameshift mutations. This approach to guide RNA molecule design is particularly useful for altering the effects of dominant negative mutations and thereby treating a subject. As a separate non-limiting example, the guide RNA molecule may be designed to target a specific pathogenic mutation of a mutated allele, such that upon DNA damage caused by the nuclease a homology directed repair (HDR) pathway is induced and leads to template mediated correction of the mutant allele. This approach to guide RNA molecule design is particularly useful for altering haploinsufficiency effects of a mutated allele and thereby treating a subject.

Non-limiting examples of specific genes which may be targeted for alteration to treat a disease or disorder are presented herein below. Specific disease-associated genes and mutations that induce a mutation disorder are described in the literature. Such mutations can be used to design a DNA-targeting RNA molecule to target a CRISPR composition to an allele of the disease associated gene, where the CRISPR composition causes DNA damage and induces a DNA repair pathway to alter the allele and thereby treat the mutation disorder.

Mutations in the ELANE gene are associated with neutropenia. Accordingly, without limitation, embodiments of the invention that target ELANE may be used in methods of treating subjects afflicted with neutropenia.

CXCR4 is a co-receptor for the human immunodeficiency virus type 1 (HIV-1) infection. Accordingly, without limitation, embodiments of the invention that target CXCR4 may be used in methods of treating subjects afflicted with HIV-1 or conferring resistance to HIV-1 infection in a subject.

Programmed cell death protein 1 (PD-1) disruption enhances CAR-T cell mediated killing of tumor cells and PD-1 may be a target in other cancer therapies. Accordingly, without limitation, embodiments of the invention that target PD-1 may be used in methods of treating subjects afflicted with cancer. In an embodiment, the treatment is CAR-T cell therapy with T cells that have been modified according to the invention to be PD-1 deficient.

In addition, BCL11A is a gene that plays a role in the suppression of hemoglobin production. Globin production may be increased to treat diseases such as thalassemia or sickle cell anemia by inhibiting BCL11A. See for example, PCT International Publication No. WO 2017/077394A2; U.S. Publication No. US2011/0182867A1; Humbert et al. Sci. Transl. Med. (2019); and Canver et al. Nature (2015). Accordingly, without limitation, embodiments of the invention that target an enhancer of BCL11A may be used in methods of treating subjects afflicted with beta thalassemia or sickle cell anemia.

Embodiments of the invention may also be used for targeting any disease-associated gene, for studying, altering, or treating any of the diseases or disorders listed in Table A or Table B below. Indeed, any disease-associated with a genetic locus may be studied, altered, or treated by using the nucleases disclosed herein to target the appropriate disease-associated gene, for example, those listed in U.S. Publication No. 2018/0282762A1 and European Patent No. EP3079726B1.

TABLE A

| Diseases, Disorders and their associated genes | |
|---|---|
| DISEASE/DISORDERS | GENE(S) |
| Neoplasia | PTEN; ATM; ATR; EGFR; ERBB2; ERBB3; ERBB4; Notch1; Notch2; Notch3; Notch4; AKT; AKT2; AKT3; HIF; HIF1a; HIF3a; Met; HRG; Bcl2; PPAR alpha; PPAR gamma; WT1 (Wilms Tumor); FGF Receptor Family members (5 members: 1, 2, 3, 4, 5); CDKN2a; APC; RB (retinoblastoma); MEN1; VHL; BRCA1; BRCA2; AR (Androgen Receptor); TSG101; IGF; IGF Receptor; Igf1 (4 variants); gf2 (3 variants); Igf 1 Receptor; Igf 2 Receptor; Bax; Bcl2; caspases family (9 members: 1, 2, 3, 4, 6, 7, 8, 9, 12); Kras; Apc |
| Age-related Macular Degeneration | Abcr; Ccl2; Cc2; cp (ceruloplasmin); Timp3; cathepsinD; Vldlr; Ccr2 |
| Schizophrenia | Neuregulin1 (Nrg1); Erb4 (receptor for Neuregulin); Complexin1 (Cplx1); Tph1 Tryptophan hydroxylase; Tph2 Tryptophan hydroxylase 2; Neurexin 1; GSK3; GSK3a; GSK3b |
| Neurological, Neuro degenerative, and Movement Disorders | 5-HTT (Slc6a4); COMT; DRD (Drd1a); SLC6A3; DAOA; DTNBP1; Dao (Dao1) |
| Trinucleotide Repeat Disorders | HTT (Huntington's Dx); SBMA/SMAX1/AR (Kennedy's Dx); FXN/X25 (Friedrich's Ataxia); ATX3 (Machado-Joseph's Dx); ATXN1 and ATXN2 (spinocerebellar ataxias); DMPK (myotonic dystrophy); Atrophin-1 and Atn1 (DRPLA Dx); CBP (Creb-BP-global instability); VLDLR (Alzheimer's); Atxn7; Atxn10 |
| Fragile X Syndrome | FMR2; FXR1; FXR2; mGLUR5 |
| Secretase Related Disorders | APH-1 (alpha and beta); Presenilin (Psen1); nicastrin (Ncstn); PEN-2 |
| Others | Nos1; Parp1; Nat1; Nat2 |
| Prion related disorders | Prp |
| ALS | SOD1; ALS2; STEX; FUS; TARDBP; VEGF (VEGF-a; VEGF-b; VEGF-c) |
| Addiction | Prkce (alcohol); Drd2; Drd4; ABAT (alcohol); GRIA2; Grm5; Grin1; Htr1b; Grin2a; Drd3; Pdyn; Gria1 (alcohol) |
| Autism | Mecp2; BZRAP1; MDGA2; Sema5A; Neurexin 1; Fragile X (FMR2 (AFF2); FXR1; FXR2; Mglur5) |
| Alzheimer's Disease | E1; CHIP; UCH; UBB; Tau; LRP; PICALM; Clusterin; PS1; SORL1; CR1; Vldlr; Uba1; Uba3; CHIP28 (Aqp1, Aquaporin1); Uchl1; Uch13; APP |
| Inflammation | IL-10; IL-1 (IL-1a; IL-1b); IL-13; IL-17 (IL-17a (CTLA8); IL-17b; IL-17c; IL-17d; IL-17f); II-23; Cx3cr1; ptpn22; TNFa; NOD2/CARD15 for IBD; IL-6; IL-12 (IL-12a; IL-12b); CTLA4; Cx3cl1 |
| Parkinson's Disease | x-Synuclein; DJ-1; LRRK2; Parkin; PINK1 |

TABLE B

| Diseases, Disorders and their associated genes | |
|---|---|
| DISEASE CATEGORY | DISEASE AND ASSOCIATED GENES |
| Blood and coagulation diseases and disorders | Anemia (CDAN1, CDA1, RPS19, DBA, PKLR, PK1, NT5C3, UMPH1, PSN1, RHAG, RH50A, NRAMP2, SPTB, ALAS2, ANH1, ASB, ABCB7, ABC7, ASAT); Bare lymphocyte syndrome (TAPBP, TPSN, TAP2, ABCB3, PSF2, RING11, MHC2TA, C2TA, RFX5, RFXAP, RFX5), Bleeding disorders (TBXA2R, P2RX1, P2X1); Factor H and factor H-like 1 (HF1, CFH, HUS); Factor V and factor VIII (MCFD2); Factor VII deficiency (F7); Factor X deficiency (F10); Factor XI deficiency (F11); Factor XII deficiency (F12, HAF); Factor XIIIA deficiency (F13A1, F13A); Factor XIIIB deficiency (F13B); Fanconi anemia (FANCA, FACA, FA1, FA, FAA, FAAP95, FAAP90, FLJ34064, FANCB, FANCC, FACC, BRCA2, FANCD1, FANCD2, FANCD, FACD, FAD, FANCE, FACE, FANCF, XRCC9, FANCG, BRIP1, BACH1, FANCJ, PHF9, FANCL, FANCM, KIAA1596); Hemophagocytic lymphohistiocytosis disorders (PRF1, HPLH2, UNC13D, MUNC13-4, HPLH3, HLH3, FHL3); Hemophilia A (F8, F8C, HEMA); Hemophilia B (F9, HEMB), Hemorrhagic disorders (PI, ATT, F5); Leukocyde deficiencies and disorders (ITGB2, CD18, LCAMB, LAD, EIF2B1, EIF2BA, EIF2B2, EIF2B3, EIF2B5, LVWM, CACH, CLE, EIF2B4); Sickle cell anemia (HBB); Thalassemia (HBA2, HBB, HBD, LCRB, HBA1) |

TABLE B-continued

| Diseases, Disorders and their associated genes | |
|---|---|
| DISEASE CATEGORY | DISEASE AND ASSOCIATED GENES |
| Cell dysregulation and oncology diseases and disorders | B-cell non-Hodgkin lymphoma (BCL7A, BCL7); Leukemia (TAL1, TCL5, SCL, TAL2, FLT3, NBS1, NBS, ZNFN1A1, IK1, LYF1, HOXD4, HOX4B, BCR, CML, PHL, ALL, ARNT, KRAS2, RASK2, GMPS, AF10, ARHGEF12, LARG, KIAA0382, CALM, CLTH, CEBPA, CEBP, CHIC2, BTL, FLT3, KIT, PBT, LPP, NPM1, NUP214, D9S46E, CAN, CAIN, RUNX1, CBFA2, AML1, WHSC1L1, NSD3, FLT3, AF1Q, NPM1, NUMA1, ZNF145, PLZF, PML, MYL, STAT5B, AF10, CALM, CLTH, ARL11, ARLTS1, P2RX7, P2X7, BCR, CML, PHL, ALL, GRAF, NF1, VRNF, WSS, NFNS, PTPN11, PTP2C, SHP2, NS1, BCL2, CCND1, PRAD1, BCL1, TCRA, GATA1, GF1, ERYF1, NFE1, ABL1, NQO1, DIA4, NMOR1, NUP214, D9S46E, CAN, CAIN) |
| Inflammation and immune related diseases and disorders | AIDS (KIR3DL1, NKAT3, NKB1, AMB11, KIR3DS1, IFNG, CXCL12, SDF1); Autoimmune lymphoproliferative syndrome (TNFRSF6, APT1, FAS, CD95, ALPS1A); Combined immunodeficiency, (IL2RG, SCIDX1, SCIDX, IMD4); HIV-1 (CCL5, SCYA5, D17S136E, TCP228), HIV susceptibility or infection (IL10, CSIF, CMKBR2, CCR2, CMKBR5, CCCKR5 (CCR5)); Immunodeficiencies (CD3E, CD3G, AICDA, AID, HIGM2, TNFRSF5, CD40, UNG, DGU, HIGM4, TNFSF5, CD40LG, HIGM1, IGM, FOXP3, IPEX, AIID, XPID, PIDX, TNFRSF14B, TACI); Inflammation (IL-10, IL-1 (IL-1a, IL-1b), IL-13, IL-17 (IL-17a (CTLA8), IL-17b, IL-17c, IL-17d, IL-17f), II-23, Cx3cr1, ptpn22, TNFa, NOD2/CARD15 for IBD, IL-6, IL-12 (IL-12a, IL-12b), CTLA4, Cx3cl1); Severe combined immunodeficiencies (SCIDs)(JAK3, JAKL, DCLRE1C, ARTEMIS, SCIDA, RAG1, RAG2, ADA, PTPRC, CD45, LCA, IL7R, CD3D, T3D, IL2RG, SCIDX1, SCIDX, IMD4) |
| Metabolic, liver, kidney and protein diseases and disorders | Amyloid neuropathy (TTR, PALB); Amyloidosis (APOA1, APP, AAA, CVAP, AD1, GSN, FGA, LYZ, TTR, PALB); Cirrhosis (KRT18, KRT8, CIRH1A, NAIC, TEX292, KIAA1988); Cystic fibrosis (CFTR, ABCC7, CF, MRP7); Glycogen storage diseases (SLC2A2, GLUT2, G6PC, G6PT, G6PT1, GAA, LAMP2, LAMPB, AGL, GDE, GBE1, GYS2, PYGL, PFKM); Hepatic adenoma, 142330 (TCF1, HNF1A, MODY3), Hepatic failure, early onset, and neurologic disorder (SCOD1, SCO1), Hepatic lipase deficiency (LIPC), Hepatoblastoma, cancer and carcinomas (CTNNB1, PDGFRL, PDGRL, PRLTS, AXIN1, AXIN, CTNNB1, TP53, P53, LFS1, IGF2R, MPRI, MET, CASP8, MCH5; Medullary cystic kidney disease (UMOD, HNFJ, FJHN, MCKD2, ADMCKD2); Phenylketonuria (PAH, PKU1, QDPR, DHPR, PTS); Polycystic kidney and hepatic disease (FCYT, PKHD1, ARPKD, PKD1, PKD2, PKD4, PKDTS, PRKCSH, G19P1, PCLD, SEC63) |
| Muscular/Skeletal diseases and disorders | Becker muscular dystrophy (DMD, BMD, MYF6), Duchenne Muscular Dystrophy (DMD, BMD); Emery-Dreifuss muscular dystrophy (LMNA, LMN1, EMD2, FPLD, CMD1A, HGPS, LGMD1B, LMNA, LMN1, EMD2, FPLD, CMD1A); Facioscapulohumeral muscular dystrophy (FSHMD1A, FSHD1A); Muscular dystrophy (FKRP, MDC1C, LGMD2I, LAMA2, LAMM, LARGE, KIAA0609, MDC1D, FCMD, TTID, MYOT, CAPN3, CANP3, DYSF, LGMD2B, SGCG, LGMD2C, DMDA1, SCG3, SGCA, ADL, DAG2, LGMD2D, DMDA2, SGCB, LGMD2E, SGCD, SGD, LGMD2F, CMD1L, TCAP, LGMD2G, CMD1N, TRIM32, HT2A, LGMD2H, FKRP, MDC1C, LGMD2I, TTN, CMD1G, TMD, LGMD2J, POMT1, CAV3, LGMD1C, SEPN1, SELN, RSMD1, PLEC1, PLTN, EBS1); Osteopetrosis (LRP5, BMND1, LRP7, LR3, OPPG, VBCH2, CLCN7, CLC7, OPTA2, OSTM1, GL, TCIRG1, TIRC7, OC116, OPTB1); Muscular atrophy (VAPB, VAPC, ALS8, SMN1, SMA1, SMA2, SMA3, SMA4, BSCL2, SPG17, GARS, SMAD1, CMT2D, HEXB, IGHMBP2, SMUBP2, CATF1, SMARD1) |
| Dermatological diseases and disorders | Albinisim (TYR, OCA2, TYRP1, SLC45A2, LYST), Ectodermal dysplasias (EDAR, EDARADD, WNT10A), Ehlers-Danlos syndrome (COL5A1, COL5A2, COL1A1, COL1A2, COL3A1, TNXB, ADAMTS2, PLOD1, FKBP14), Ichthyosis-associated disorders (FLG, STS, TGM1, ALOXE3/ALOX12B, KRT1, KRT10, ABCA12, KRT2, GJB2, TGM1, ABCA12, CYP4F22, ALOXE3, CERS3, NSHDL, EBP, MBTPS2, GJB2, SPINK5, AGHD5, PHYH, PEX7, ALDH3A2, ERCC2, ERCC3, GFT2H5, GBA), Incontinentia pigmenti (IKBKG, NEMO), Tuberous sclerosis (TSC1, TSC2), Premature aging syndromes (POLR3A, PYCR1, LMNA, POLD1, WRN, DMPK) |

TABLE B-continued

| Diseases, Disorders and their associated genes | |
|---|---|
| DISEASE CATEGORY | DISEASE AND ASSOCIATED GENES |
| Neurological and Neuronal diseases and disorders | ALS (SOD1, ALS2, STEX, FUS, TARDBP, VEGF (VEGF-a, VEGF-b, VEGF-c); Alzheimer disease (APP, AAA, CVAP, AD1, APOE, AD2, PSEN2, AD4, STM2, APBB2, FE65L1, NOS3, PLAU, URK, ACE, DCP1, ACE1, MPO, PACIP1, PAXIP1L, PTIP, A2M, BLMH, BMH, PSEN1, AD3); Autism (Mecp2, BZRAP1, MDGA2, Sema5A, Neurexin 1, GLO1, MECP2, RTT, PPMX, MRX16, MRX79, NLGN3, NLGN4, KIAA1260, AUTSX2); Fragile X Syndrome (FMR2, FXR1, FXR2, mGLUR5); Huntington's disease and disease like disorders (HD, IT15, PRNP, PRIP, JPH3, JP3, HDL2, TBP, SCA17); Parkinson disease (NR4A2, NURR1, NOT, TINUR, SNCAIP, TBP, SCA17, SNCA, NACP, PARK1, PARK4, DJ1, PARK7, LRRK2, PARK8, PINK1, PARK6, UCHL1, PARK5, SNCA, NACP, PARK1, PARK4, PRKN, PARK2, PDJ, DBH, NDUFV2); Rett syndrome (MECP2, RTT, PPMX, MRX16, MRX79, CDKL5, STK9, MECP2, RTT, PPMX, MRX16, MRX79, x-Synuclein, DJ-1); Schizophrenia (Neuregulin1 (Nrg1), Erb4 (receptor for Neuregulin), Complexin1 (Cplx1), Tph1 Tryptophan hydroxylase, Tph2, Tryptophan hydroxylase 2, Neurexin 1, GSK3, GSK3a, GSK3b, 5-HTT (Slc6a4), COMT, DRD (Drd1a), SLC6A3, DAOA, DTNBP1, Dao (Dao1)); Secretase Related Disorders (APH-1 (alpha and beta), Presenilin (Psen1), nicastrin, (Ncstn), PEN-2, Nos1, Parp1, Natl, Nat2); Trinucleotide Repeat Disorders (HTT (Huntington's Dx), SBMA/SMAX1/AR (Kennedy's Dx), FXN/X25 (Friedrich's Ataxia), ATX3 (Machado-Joseph's Dx), ATXN1 and ATXN2 (spinocerebellar ataxias), DMPK (myotonic dystrophy), Atrophin-1 and Atn1 (DRPLA Dx), CBP (Creb-BP-global instability), VLDLR (Alzheimer's), Atxn7, Atxn10) |
| Ocular diseases and disorders | Age-related macular degeneration (Abcr, Ccl2, Cc2, cp (ceruloplasmin), Timp3, cathepsinD, Vldlr, Ccr2); Cataract (CRYAA, CRYA1, CRYBB2, CRYB2, PITX3, BFSP2, CP49, CP47, CRYAA, CRYA1, PAX6, AN2, MGDA, CRYBA1, CRYB1, CRYGC, CRYG3, CCL, LIM2, MP19, CRYGD, CRYG4, BFSP2, CP49, CP47, HSF4, CTM, HSF4, CTM, MIP, AQP0, CRYAB, CRYA2, CTPP2, CRYBB1, CRYGD, CRYG4, CRYBB2, CRYB2, CRYGC, CRYG3, CCL, CRYAA, CRYA1, GJA8, CX50, CAE1, GJA3, CX46, CZP3, CAE3, CCM1, CAM, KRIT1); Corneal clouding and dystrophy (APOA1, TGFBI, CSD2, CDGG1, CSD, BIGH3, CDG2, TACSTD2, TROP2, M1S1, VSX1, RINX, PPCD, PPD, KTCN, COL8A2, FECD, PPCD2, PIP5K3, CFD); Cornea plana congenital (KERA, CNA2); Glaucoma (MYOC, TIGR, GLC1A, JOAG, GPOA, OPTN, GLC1E, FIP2, HYPL, NRP, CYP1B1, GLC3A, OPA1, NTG, NPG, CYP1B1, GLC3A); Leber congenital amaurosis (CRB1, RP12, CRX, CORD2, CRD, RPGRIP1, LCA6, CORD9, RPE65, RP20, AIPL1, LCA4, GUCY2D, GUC2D, LCA1, CORD6, RDH12, LCA3); Macular dystrophy (ELOVL4, ADMD, STGD2, STGD3, RDS, RP7, PRPH2, PRPH, AVMD, AOFMD, VMD2) |

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

In the discussion unless otherwise stated, adjectives such as "substantially" and "about" modifying a condition or relationship characteristic of a feature or features of an embodiment of the invention, are understood to mean that the condition or characteristic is defined to within tolerances that are acceptable for operation of the embodiment for an application for which it is intended. Unless otherwise indicated, the word "or" in the specification and claims is considered to be the inclusive "or" rather than the exclusive or, and indicates at least one of and any combination of items it conjoins.

It should be understood that the terms "a" and "an" as used above and elsewhere herein refer to "one or more" of the enumerated components. It will be clear to one of ordinary skill in the art that the use of the singular includes the plural unless specifically stated otherwise. Therefore, the terms "a," "an" and "at least one" are used interchangeably in this application.

For purposes of better understanding the present teachings and in no way limiting the scope of the teachings, unless otherwise indicated, all numbers expressing quantities, percentages or proportions, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained. At the very least, each numerical parameter should at least be construed in light of the number of reported significant digits and by applying ordinary rounding techniques.

It is understood that where a numerical range is recited herein, the present invention contemplates each integer between, and including, the upper and lower limits, unless otherwise stated.

In the description and claims of the present application, each of the verbs, "comprise," "include" and "have" and conjugates thereof, are used to indicate that the object or objects of the verb are not necessarily a complete listing of components, elements or parts of the subject or subjects of the verb. Other terms as used herein are meant to be defined by their well-known meanings in the art.

The terms "polynucleotide", "nucleotide", "nucleotide sequence", "nucleic acid" and "oligonucleotide" are used interchangeably. They refer to a polymeric form of nucleotides of any length, either deoxyribonucleotides or ribonucleotides, or analogs thereof. Polynucleotides may have any three-dimensional structure, and may perform any function, known or unknown. The following are non-limiting examples of polynucleotides: coding or non-coding regions of a gene or gene fragment, loci (locus) defined from linkage analysis, exons, in Irons, messenger RNA (mRNA), transfer RNA, ribosomal RNA, short interfering RNA (siRNA), short-hairpin RNA (shRNA), micro-RNA (miRNA), ribozymes, cDNA, recombinant polynucleotides, branched polynucleotides, plasmids, vectors, isolated DNA of any sequence, isolated RNA of any sequence, nucleic acid probes, and primers, A polynucleotide may comprise one or more modified nucleotides, such as methylated nucleotides and nucleotide analogs. If present, modifications to the nucleotide structure may be imparted before or after assembly of the polymer. The sequence of nucleotides may be interrupted by non-nucleotide components. A polynucleotide may be further modified after polymerization, such as by conjugation with a labeling component.

The term "nucleotide analog" or "modified nucleotide" refers to a nucleotide that contains one or more chemical modifications (e.g., substitutions), in or on the nitrogenous base of the nucleoside (e.g., cytosine (C), thymine (T) or uracil (U), adenine (A) or guanine (G)), in or on the sugar moiety of the nucleoside (e.g., ribose, deoxyribose, modified ribose, modified deoxyribose, six-membered sugar analog, or open-chain sugar analog), or the phosphate. Each of the RNA sequences described herein may comprise one or more nucleotide analogs.

As used herein, the following nucleotide identifiers are used to represent a referenced nucleotide base(s):

| Nucleotide reference | Base(s) represented | | | |
|---|---|---|---|---|
| A | A | | | |
| C | | C | | |
| G | | | G | |
| T | | | | T |
| W | A | | | T |
| S | | C | G | |
| M | A | C | | |
| K | | | G | T |
| R | A | | G | |
| Y | | C | | T |
| B | | C | G | T |
| D | A | | G | T |
| H | A | C | | T |
| V | A | C | G | |
| N | A | C | G | T |

As used herein, the term "targeting sequence" or "targeting molecule" refers a nucleotide sequence or molecule comprising a nucleotide sequence that is capable of hybridizing to a specific target sequence, e.g., the targeting sequence has a nucleotide sequence which is at least partially complementary to the sequence being targeted along the length of the targeting sequence. The targeting sequence or targeting molecule may be part of a targeting RNA molecule that can form a complex with a CRISPR nuclease with the targeting sequence serving as the targeting portion of the CRISPR complex. When the molecule having the targeting sequence is present contemporaneously with the CRISPR molecule, the RNA molecule is capable of targeting the CRISPR nuclease to the specific target sequence. Each possibility represents a separate embodiment. A targeting RNA molecule can be custom designed to target any desired sequence.

The term "targets" as used herein, refers to preferential hybridization of a targeting sequence or a targeting molecule to a nucleic acid having a targeted nucleotide sequence. It is understood that the term "targets" encompasses variable hybridization efficiencies, such that there is preferential targeting of the nucleic acid having the targeted nucleotide sequence, but unintentional off-target hybridization in addition to on-target hybridization might also occur. It is understood that where an RNA molecule targets a sequence, a complex of the RNA molecule and a CRISPR nuclease molecule targets the sequence for nuclease activity.

In the context of targeting a DNA sequence that is present in a plurality of cells, it is understood that the targeting encompasses hybridization of the guide sequence portion of the RNA molecule with the sequence in one or more of the cells, and also encompasses hybridization of the RNA molecule with the target sequence in fewer than all of the cells in the plurality of cells. Accordingly, it is understood that where an RNA molecule targets a sequence in a plurality of cells, a complex of the RNA molecule and a CRISPR nuclease is understood to hybridize with the target sequence in one or more of the cells, and also may hybridize with the target sequence in fewer than all of the cells. Accordingly, it is understood that the complex of the RNA molecule and the CRISPR nuclease introduces a double strand break in relation to hybridization with the target sequence in one or more cells and may also introduce a double strand break in relation to hybridization with the target sequence in fewer than all of the cells. As used herein, the term "modified cells" refers to cells in which a double strand break is affected by a complex of an RNA molecule and the CRISPR nuclease as a result of hybridization with the target sequence, i.e. on-target hybridization.

As used herein the term "wild type" is a term of the art understood by skilled persons and means the typical form of an organism, strain, gene or characteristic as it occurs in nature as distinguished from mutant or variant forms. Accordingly, as used herein, where a sequence of amino acids or nucleotides refers to a wild type sequence, a variant refers to variant of that sequence, e.g., comprising substitutions, deletions, insertions. In embodiments of the present invention, an engineered CRISPR nuclease is a variant CRISPR nuclease comprising at least one amino acid modification (e.g., substitution, deletion, and/or insertion) compared to the CRISPR nuclease of any of the CRISPR nucleases indicated in Table 1.

The terms "non-naturally occurring" or "engineered" are used interchangeably and indicate human manipulation. The terms, when referring to nucleic acid molecules or polypeptides may mean that the nucleic acid molecule or the polypeptide is at least substantially free from at least one other component with which they are naturally associated in nature and as found in nature.

As used herein the term "amino acid" includes natural and/or unnatural or synthetic amino acids, including glycine and both the D or I, optical isomers, and amino acid analogs and peptidomimetics.

As used herein, "genomic DNA" refers to linear and/or chromosomal DNA and/or to plasmid or other extrachromosomal DNA sequences present in the cell or cells of interest. In some embodiments, the cell of interest is a eukaryotic cell. In some embodiments, the cell of interest is a prokaryotic cell. In some embodiments, the methods produce double-stranded breaks (DSBs) at pre-determined target sites in a genomic DNA sequence, resulting in mutation, insertion, and/or deletion of DNA sequences at the target site(s) in a genome.

"Eukaryotic" cells include, but are not limited to, fungal cells (such as yeast), plant cells, animal cells, mammalian cells and human cells.

The term "nuclease" as used herein refers to an enzyme capable of cleaving the phosphodiester bonds between the nucleotide subunits of nucleic acid. A nuclease may be isolated or derived from a natural source. The natural source may be any living organism. Alternatively, a nuclease may be a modified or a synthetic protein which retains the phosphodiester bond cleaving activity.

The term "PAM" as used herein refers to a nucleotide sequence of a target DNA located in proximity to the targeted DNA sequence and recognized by the CRISPR nuclease. The PAM sequence may differ depending on the nuclease identity.

The term "mutation disorder" or "mutation disease" as used herein refers to any disorder or disease that is related to dysfunction of a gene caused by a mutation. A dysfunctional gene manifesting as a mutation disorder contains a mutation in at least one of its alleles and is referred to as a "disease-associated gene." The mutation may be in any portion of the disease-associated gene, for example, in a regulatory, coding, or non-coding portion. The mutation may be any class of mutation, such as a substitution, insertion, or deletion. The mutation of the disease-associated gene may manifest as a disorder or disease according to the mechanism of any type of mutation, such as a recessive, dominant negative, gain-of-function, loss-of-function, or a mutation leading to haploinsufficiency of a gene product.

A skilled artisan will appreciate that embodiments of the present invention disclose RNA molecules capable of complexing with a nuclease, e.g. a CRISPR nuclease, such as to associate with a target genomic DNA sequence of interest next to a protospacer adjacent motif (PAM). The nuclease then mediates cleavage of target DNA to create a double-stranded break within the protospacer.

In embodiments of the present invention, a CRISPR nuclease and a targeting molecule form a CRISPR complex that binds to a target DNA sequence to effect cleavage of the target DNA sequence. A CRISPR nuclease may form a CRISPR complex comprising the CRISPR nuclease and RNA molecule without a further, separate tracrRNA molecule. Alternatively, CRISPR nucleases may form a CRISPR complex between the CRISPR nuclease, an RNA molecule, and a tracrRNA molecule.

The term "protein binding sequence" or "nuclease binding sequence" refers to a sequence capable of binding with a CRISPR nuclease to form a CRISPR complex. A skilled artisan will understand that a tracrRNA capable of binding with a CRISPR nuclease to form a CRISPR complex comprises a protein or nuclease binding sequence.

An "RNA binding portion" of a CRISPR nuclease refers to a portion of the CRISPR nuclease which may bind to an RNA molecule to form a CRISPR complex, e.g. the nuclease binding sequence of a tracrRNA molecule. An "activity portion" or "active portion" of a CRISPR nuclease refers to a portion of the CRISPR nuclease which effects a double strand break in a DNA molecule, for example when in complex with a DNA-targeting RNA molecule.

An RNA molecule may comprise a sequence sufficiently complementary to a tracrRNA molecule so as to hybridize to the tracrRNA via basepairing and promote the formation of a CRISPR complex. (See U.S. Pat. No. 8,906,616). In embodiments of the present invention, the RNA molecule may further comprise a portion having a tracr mate sequence.

In embodiments of the present invention, the targeting molecule may further comprise the sequence of a tracrRNA molecule. Such embodiments may be designed as a synthetic fusion of the guide portion of the RNA molecule (gRNA or crRNA) and the trans-activating crRNA (tracrRNA), together forming a single guide RNA (sgRNA). (See Jinek et al., Science (2012)). Embodiments of the present invention may also form CRISPR complexes utilizing a separate tracrRNA molecule and a separate RNA molecule comprising a guide sequence portion. In such embodiments the tracrRNA molecule may hybridize with the RNA molecule via base pairing and may be advantageous in certain applications of the invention described herein.

In embodiments of the present invention an RNA molecule may comprise a "nexus" region and/or "hairpin" regions which may further define the structure of the RNA molecule. (See Briner et al., Molecular Cell (2014)).

As used herein, the term "direct repeat sequence" refers to two or more repeats of a specific amino acid sequence of nucleotide sequence.

As used herein, an RNA sequence or molecule capable of "interacting with" or "binding" with a CRISPR nuclease refers to the RNA sequence or molecules ability to form a CRISPR complex with the CRISPR nuclease.

As used herein, the term "operably linked" refers to a relationship (i.e. fusion, hybridization) between two sequences or molecules permitting them to function in their intended manner. In embodiments of the present invention, when an RNA molecule is operably linked to a promoter, both the RNA molecule and the promotor are permitted to function in their intended manner.

As used herein, the term "heterologous promoter" refers to a promoter that does not naturally occur together with the molecule or pathway being promoted.

As used herein, a sequence or molecule has an X % "sequence identity" to another sequence or molecule if X % of bases or amino acids between the sequences of molecules are the same and in the same relative position. For example, a first nucleotide sequence having at least a 95% sequence identity with a second nucleotide sequence will have at least 95% of bases, in the same relative position, identical with the other sequence.

Nuclear Localization Sequences

The terms "nuclear localization sequence" and "NLS" are used interchangeably to indicate an amino acid sequence/peptide that directs the transport of a protein with which it is associated from the cytoplasm of a cell across the nuclear envelope barrier. The term "NLS" is intended to encompass not only the nuclear localization sequence of a particular peptide, but also derivatives thereof that are capable of directing translocation of a cytoplasmic polypeptide across the nuclear envelope barrier. NLSs are capable of directing nuclear translocation of a polypeptide when attached to the N-terminus, the C-terminus, or both the N- and C-termini of the polypeptide. In addition, a polypeptide having an NLS coupled by its N- or C-terminus to amino acid side chains located randomly along the amino acid sequence of the polypeptide will be translocated. Typically, an NLS consists of one or more short sequences of positively charged lysines or arginines exposed on the protein surface, but other types of NLS are known. Non-limiting examples of NLSs include an NLS sequence derived from: the SV40 virus large T-antigen, nucleoplasmin, c-myc, the hRNPA1 M9 NLS, the IBB domain from importin-alpha, myoma T protein, human p53, mouse c-abl IV, influenza vims NS1, Hepatitis virus delta antigen, mouse Mx1 protein, human poly(ADP-ribose) polymerase, and the steroid hormone receptors (human) glucocorticoid.

Delivery

The CRISPR nuclease or CRISPR compositions described herein may be delivered as a protein, DNA molecules, RNA molecules, Ribonucleoproteins (RNP), nucleic acid vectors, or any combination thereof. In some embodiments, the RNA molecule comprises a chemical modification. Non-limiting examples of suitable chemical modifications include 2'-0-methyl (M), 2'-0-methyl, 3'phosphorothioate (MS) or 2'-0-methyl, 3'thioPACE (MSP), pseudouridine, and 1-methyl pseudo-uridine. Each possibility represents a separate embodiment of the present invention.

The CRISPR nucleases and/or polynucleotides encoding same described herein, and optionally additional proteins (e.g., ZFPs, TALENs, transcription factors, restriction enzymes) and/or nucleotide molecules such as guide RNA may be delivered to a target cell by any suitable means. The target cell may be any type of cell e.g., eukaryotic or prokaryotic, in any environment e.g., isolated or not, maintained in culture, in vitro, ex vivo, in vivo or in planta.

In some embodiments, the composition to be delivered includes mRNA of the nuclease and RNA of the guide. In some embodiments, the composition to be delivered includes mRNA of the nuclease, RNA of the guide and a donor template. In some embodiments, the composition to be delivered includes the CRISPR nuclease and guide RNA. In some embodiments, the composition to be delivered includes the CRISPR nuclease, guide RNA and a donor template for gene editing via, for example, homology directed repair. In some embodiments, the composition to be delivered includes mRNA of the nuclease, DNA-targeting RNA and the tracrRNA. In some embodiments, the composition to be delivered includes mRNA of the nuclease, DNA-targeting RNA and the tracrRNA and a donor template. In some embodiments, the composition to be delivered includes the CRISPR nuclease DNA-targeting RNA and the tracrRNA. In some embodiments, the composition to be delivered includes the CRISPR nuclease, DNA-targeting RNA and the tracrRNA and a donor template for gene editing via, for example, homology directed repair.

Any suitable viral vector system may be used to deliver RNA compositions. Conventional viral and non-viral based gene transfer methods can be used to introduce nucleic acids and/or CRISPR nuclease in cells (e.g., mammalian cells, plant cells, etc.) and target tissues. Such methods can also be used to administer nucleic acids encoding and/or CRISPR nuclease protein to cells in vitro. In certain embodiments, nucleic acids and/or CRISPR nuclease are administered for in vivo or ex vivo gene therapy uses. Non-viral vector delivery systems include naked nucleic acid, and nucleic acid complexed with a delivery vehicle such as a liposome or poloxamer. For a review of gene therapy procedures, see Anderson, Science (1992); Nabel and Felgner, TIBTECH (1993); Mitani and Caskey, TIBTECH (1993); Dillon, TIBTECH (1993); Miller, Nature (1992); Van Brunt, Biotechnology (1988); Vigne et al., Restorative Neurology and Neuroscience 8:35-36 (1995); Kremer and Perricaudet, British Medical Bulletin (1995); Haddada et al., Current Topics in Microbiology and Immunology (1995); and Yu et al., Gene Therapy 1:13-26 (1994).

Methods of non-viral delivery of nucleic acids and/or proteins include electroporation, lipofection, microinjection, biolistics, particle gun acceleration, virosomes, liposomes, immunoliposomes, lipid nanoparticles (LNPs), polycation or lipid:nucleic acid conjugates, artificial virions, and agent-enhanced uptake of nucleic acids or can be delivered to plant cells by bacteria or viruses (e.g., *Agrobacterium, Rhizobium* sp. NGR234, Sinorhizoboiummeliloti, *Mesorhizobium loti*, tobacco mosaic virus, potato virus X, cauliflower mosaic virus and cassava vein mosaic virus. See, e.g., Chung et al. Trends Plant Sci. (2006). Sonoporation using, e.g., the Sonitron 2000 system (Rich-Mar) can also be used for delivery of nucleic acids. Cationic-lipid mediated delivery of proteins and/or nucleic acids is also contemplated as an in vivo, ex vivo, or in vitro delivery method. See Zuris et al., Nat. Biotechnol. (2015), Coelho et al., N. Engl. J. Med. (2013); Judge et al., Mol. Ther. (2006); and Basha et al., Mol. Ther. (2011).

Non-viral vectors, such as transposon-based systems e.g. recombinant Sleeping Beauty transposon systems or recombinant PiggyBac transposon systems, may also be delivered to a target cell and utilized for transposition of a polynucleotide sequence of a molecule of the composition or a polynucleotide sequence encoding a molecule of the composition in the target cell.

Additional exemplary nucleic acid delivery systems include those provided by Amaxa® Biosystems (Cologne, Germany), Maxcyte, Inc. (Rockville, Md.), BTX Molecular Delivery Systems (Holliston, Mass.) and Copernicus Therapeutics Inc., (see for example U.S. Pat. No. 6,008,336). Lipofection is described in e.g., U.S. Pat. Nos. 5,049,386, 4,946,787; and 4,897,355) and lipofection reagents are sold commercially (e.g., Transfectam™, Lipofectin™ and Lipofectamine™ RNAiMAX). Cationic and neutral lipids that are suitable for efficient receptor-recognition lipofection of polynucleotides include those disclosed in PCT International Publication Nos. WO/1991/017424 and WO/1991/016024. Delivery can be to cells (ex vivo administration) or target tissues (in vivo administration).

The preparation of lipid:nucleic acid complexes, including targeted liposomes such as immunolipid complexes, is well known to one of skill in the art (see, e.g., Crystal, Science (1995); Blaese et al., Cancer Gene Ther. (1995); Behr et al., Bioconjugate Chem. (1994); Remy et al., Bioconjugate Chem. (1994); Gao and Huang, Gene Therapy (1995); Ahmad and Allen, Cancer Res., (1992); U.S. Pat.

Nos. 4,186,183; 4,217,344; 4,235,871; 4,261,975; 4,485,054; 4,501,728; 4,774,085; 4,837,028; and 4,946,787).

Additional methods of delivery include the use of packaging the nucleic acids to be delivered into EnGeneIC delivery vehicles (EDVs). These EDVs are specifically delivered to target tissues using bispecific antibodies where one arm of the antibody has specificity for the target tissue and the other has specificity for the EDV. The antibody brings the EDVs to the target cell surface and then the EDV is brought into the cell by endocytosis. Once in the cell, the contents are released (see MacDiamid et al., Nature Biotechnology (2009)).

Delivery vehicles include, but are not limited to, bacteria, preferably non-pathogenic, vehicles, nanoparticles, exosomes, microvesicles, gene gun delivery, for example, by attachment of a composition to a gold particle which is fired into a cell using via a "gene-gun", viral vehicles, including but not limited to lentiviruses, AAV, and retroviruses), virus-like particles (VLPs). large VLPs (LVLPs), lentivirus-like particles, transposons, viral vectors, naked vectors, DNA, or RNA, among other delivery vehicles known in the art.

The delivery of a CRISPR nuclease and/or a polynucleotide encoding the CRIPSR nuclease, and optionally additional nucleotide molecules and/or additional proteins or peptides, may be performed by utilizing a single delivery vehicle or method or a combination of different delivery vehicles or methods. For example, a CRISPR nuclease may be delivered to a cell utilizing an LNP, and a crRNA molecule and tracrRNA molecule may be delivered to the cell utilizing AAV. Alternatively, a CRISPR nuclease may be delivered to a cell utilizing an AAV particle, and a crRNA molecule and tracrRNA molecule may be delivered to the cell utilizing a separate AAV particle, which may be advantageous due to size limitations.

The use of RNA or DNA viral based systems for the delivery of nucleic acids take advantage of highly evolved processes for targeting a virus to specific cells in the body and trafficking the viral payload to the nucleus. Viral vectors can be administered directly to patients (in vivo) or they can be used to treat cells in vitro and the modified cells are administered to patients (ex vivo). Conventional viral based systems for the delivery of nucleic acids include, but are not limited to, recombinant retroviral, lentivirus, adenoviral, adeno-associated, vaccinia and herpes simplex virus vectors for gene transfer. However, an RNA virus is preferred for delivery of the RNA compositions described herein. Additionally, high transduction efficiencies have been observed in many different cell types and target tissues. Nucleic acid of the invention may be delivered by non-integrating lentivirus. Optionally, RNA delivery with Lentivirus is utilized. Optionally the lentivirus includes mRNA of the nuclease, RNA of the guide. Optionally the lentivirus includes mRNA of the nuclease, RNA of the guide and a donor template. Optionally, the lentivirus includes the nuclease protein, guide RNA. Optionally, the lentivirus includes the nuclease protein, guide RNA and/or a donor template for gene editing via, for example, homology directed repair. Optionally the lentivirus includes mRNA of the nuclease, DNA-targeting RNA, and the tracrRNA. Optionally the lentivirus includes mRNA of the nuclease, DNA-targeting RNA, and the tracrRNA, and a donor template. Optionally, the lentivirus includes the nuclease protein, DNA-targeting RNA, and the tracrRNA. Optionally, the lentivirus includes the nuclease protein, DNA-targeting RNA, and the tracrRNA, and a donor template for gene editing via, for example, homology directed repair.

As mentioned above, the compositions described herein may be delivered to a target cell using a non-integrating lentiviral particle method, e.g. a LentiFlash® system. Such a method may be used to deliver mRNA or other types of RNAs into the target cell, such that delivery of the RNAs to the target cell results in assembly of the compositions described herein inside of the target cell. See also PCT International Publication Nos. WO2013/014537, WO2014/016690, WO2016185125, WO2017194902, and WO2017194903.

The tropism of a retrovirus can be altered by incorporating foreign envelope proteins, expanding the potential target population of target cells. Lentiviral vectors are retroviral vectors capable of transducing or infecting non-dividing cells and typically produce high viral titers. Selection of a retroviral gene transfer system depends on the target tissue. Retroviral vectors are comprised of cis-acting long terminal repeats with packaging capacity for up to 6-10 kb of foreign sequence. The minimum cis-acting LTRs are sufficient for replication and packaging of the vectors, which are then used to integrate the therapeutic gene into the target cell to provide permanent transgene expression. Widely used retroviral vectors include those based upon murine leukemia virus (MuLV), gibbon ape leukemia virus (GaLV), Simian Immunodeficiency virus (SIV), human immunodeficiency virus (HIV), and combinations thereof (see, e.g., Buchscher Panganiban, J. Virol. (1992); Johann et al., J. Virol. (1992); Sommerfelt et al., Virol. (1990); Wilson et al., J. Virol. (1989); Miller et al., J. Virol. (1991); PCT International Publication No. WO/1994/026877A1).

At least six viral vector approaches are currently available for gene transfer in clinical trials, which utilize approaches that involve complementation of defective vectors by genes inserted into helper cell lines to generate the transducing agent.

pLASN and MFG-S are examples of retroviral vectors that have been used in clinical trials (Dunbar et al., Blood (1995); Kohn et al., Nat. Med. (1995); Malech et al., PNAS (1997)). PA317/pLASN was the first therapeutic vector used in a gene therapy trial. (Blaese et al., Science (1995)). Transduction efficiencies of 50% or greater have been observed for MFG-S packaged vectors. (Ellem et al., Immunol Immunother. (1997); Dranoff et al., Hum. Gene Ther. (1997).

Packaging cells are used to form virus particles that are capable of infecting a host cell. Such cells include 293 cells, which package adenovirus, AAV, and psi.2 cells or PA317 cells, which package retrovirus. Viral vectors used in gene therapy are usually generated by a producer cell line that packages a nucleic acid vector into a viral particle. The vectors typically contain the minimal viral sequences required for packaging and subsequent integration into a host (if applicable), other viral sequences being replaced by an expression cassette encoding the protein to be expressed. The missing viral functions are supplied in trans by the packaging cell line. For example, AAV vectors used in gene therapy typically only possess inverted terminal repeat (ITR) sequences from the AAV genome which are required for packaging and integration into the host genome. Viral DNA is packaged in a cell line, which contains a helper plasmid encoding the other AAV genes, namely rep and cap, but lacking ITR sequences. The cell line is also infected with adenovirus as a helper. The helper virus promotes replication of the AAV vector and expression of AAV genes from the helper plasmid. The helper plasmid is not packaged in significant amounts due to a lack of ITR sequences. Contamination with adenovirus can be reduced by, e.g., heat treatment to which adenovirus is more sensitive than AAV. Additionally, AAV can be produced at clinical scale using baculovirus systems (see U.S. Pat. No. 7,479,554).

In many gene therapy applications, it is desirable that the gene therapy vector be delivered with a high degree of specificity to a particular tissue type. Accordingly, a viral vector can be modified to have specificity for a given cell type by expressing a ligand as a fusion protein with a viral coat protein on the outer surface of the virus. The ligand is chosen to have affinity for a receptor known to be present on the cell type of interest. For example, Han et al., Proc. Natl. Acad. Sci. USA (1995), reported that Moloney murine leukemia virus can be modified to express human heregulin fused to gp70, and the recombinant virus infects certain human breast cancer cells expressing human epidermal growth factor receptor. This principle can be extended to other virus-target cell pairs, in which the target cell expresses a receptor and the virus expresses a fusion protein comprising a ligand for the cell-surface receptor. For example, filamentous phage can be engineered to display antibody fragments (e.g., FAB or Fv) having specific binding affinity for virtually any chosen cellular receptor. Although the above description applies primarily to viral vectors, the same principles can be applied to non-viral vectors. Such vectors can be engineered to contain specific uptake sequences which favor uptake by specific target cells.

Gene therapy vectors can be delivered in vivo by administration to an individual patient, typically by systemic administration (e.g., intravenous, intraperitoneal, intramuscular, subdermal, or intracranial infusion) or topical application, as described below. Alternatively, vectors can be delivered to cells ex vivo, such as cells explanted from an individual patient (e.g., lymphocytes, bone marrow aspirates, tissue biopsy) or universal donor hematopoietic stem cells, followed by reimplantation of the cells into a patient, usually after selection for cells which have incorporated the vector. In some embodiments, delivery of mRNA in vivo and ex vivo, and RNPs delivery may be utilized.

Ex vivo cell transfection for diagnostics, research, or for gene therapy (e.g., via re-infusion of the transfected cells into the host organism) is well known to those of skill in the art. In a preferred embodiment, cells are isolated from the subject organism, transfected with an RNA composition, and re-infused back into the subject organism (e.g., patient). Various cell types suitable for ex vivo transfection are well known to those of skill in the art (see, e.g., Freshney, "Culture of Animal Cells, A Manual of Basic Technique and Specialized Applications (6th edition, 2010)) and the references cited therein for a discussion of how to isolate and culture cells from patients).

Suitable cells include but not limited to eukaryotic and prokaryotic cells and/or cell lines. Non-limiting examples of such cells or cell lines generated from such cells include COS, CHO (e.g., CHO-S, CHO-K1, CHO-DG44, CHO-DUXB11, CHO-DUKX, CHOK1SV), VERO, MDCK, WI38, V79, B14AF28-G3, BHK, HaK, NSO, SP2/0-Ag14, HeLa, HEK293 (e.g., HEK293-F, HEK293-H, HEK293-T), and perC6 cells, any plant cell (differentiated or undifferentiated) as well as insect cells such as Spodopterafugiperda (Sf), or fungal cells such as *Saccharomyces, Pichia* and *Schizosaccharomyces*. In certain embodiments, the cell line is a CHO-K1, MDCK or HEK293 cell line. Additionally, primary cells may be isolated and used ex vivo for reintroduction into the subject to be treated following treatment with the nucleases (e.g. ZFNs or TALENs) or nuclease systems (e.g. CRISPR). Suitable primary cells include peripheral blood mononuclear cells (PBMC), and other blood cell subsets such as, but not limited to, CD4+ T cells or CD8+ T cells. Suitable cells also include stem cells such as, by way of example, embryonic stem cells, induced pluripotent stem cells, hematopoietic stem cells (CD34+), neuronal stem cells and mesenchymal stem cells.

In one embodiment, stem cells are used in ex vivo procedures for cell transfection and gene therapy. The advantage to using stem cells is that they can be differentiated into other cell types in-vitro or can be introduced into a mammal (such as the donor of the cells) where they will engraft in the bone marrow. Methods for differentiating CD34+ cells in vitro into clinically important immune cell types using cytokines such a GM-CSF, IFN-gamma. and TNF-alpha are known (as a non-limiting example see, Inaba et al., J. Exp. Med. (1992)).

Stem cells are isolated for transduction and differentiation using known methods. For example, stem cells are isolated from bone marrow cells by panning the bone marrow cells with antibodies which bind unwanted cells, such as CD4+ and CD8+ (T cells), CD45+ (panB cells), GR-1 (granulocytes), and Tad (differentiated antigen presenting cells) (as a non-limiting example see Inaba et al., J. Exp. Med. (1992)). Stem cells that have been modified may also be used in some embodiments.

Notably, any one of the CRISPR nucleases described herein may be suitable for genome editing in post-mitotic cells or any cell which is not actively dividing, e.g., arrested cells. Examples of post-mitotic cells which may be edited using a CRISPR nuclease of the present invention include, but are not limited to, myocyte, a cardiomyocyte, a hepatocyte, an osteocyte and a neuron.

Vectors (e.g., retroviruses, liposomes, etc.) containing therapeutic RNA compositions can also be administered directly to an organism for transduction of cells in vivo. Alternatively, naked RNA or mRNA can be administered. Administration is by any of the routes normally used for introducing a molecule into ultimate contact with blood or tissue cells including, but not limited to, injection, infusion, topical application and electroporation. Suitable methods of administering such nucleic acids are available and well known to those of skill in the art, and, although more than one route can be used to administer a particular composition, a particular route can often provide a more immediate and more effective reaction than another route.

Vectors suitable for introduction of transgenes into immune cells (e.g., T-cells) include non-integrating lentivirus vectors. See, for example, U.S. Patent Publication No. 2009/0117617.

Pharmaceutically acceptable carriers are determined in part by the particular composition being administered, as well as by the particular method used to administer the composition. Accordingly, there is a wide variety of suitable formulations of pharmaceutical compositions available, as described below (see, e.g., Remington's Pharmaceutical Sciences, 17th ed., 1989).

DNA Repair by Homologous Recombination

The term "homology-directed repair" or "HDR" refers to a mechanism for repairing DNA damage in cells, for example, during repair of double-stranded and single-stranded breaks in DNA. HDR requires nucleotide sequence homology and uses a "nucleic acid template" (nucleic acid template or donor template used interchangeably herein) to repair the sequence where the double-stranded or single break occurred (e.g., DNA target sequence). This results in the transfer of genetic information from, for example, the nucleic acid template to the DNA target sequence. HDR may result in alteration of the DNA target sequence (e.g., insertion, deletion, mutation) if the nucleic acid template sequence differs from the DNA target sequence and part or all of the nucleic acid template polynucleotide or oligonucleotide is incorporated into the DNA target sequence. In some embodiments, an entire nucleic acid template polynucleotide, a portion of the nucleic acid template polynucleotide, or a copy of the nucleic acid template is integrated at the site of the DNA target sequence.

The terms "nucleic acid template" and "donor", refer to a nucleotide sequence that is inserted or copied into a genome. The nucleic acid template comprises a nucleotide sequence, e.g., of one or more nucleotides, that will be added to or will template a change in the target nucleic acid or may be used to modify the target sequence. A nucleic acid template sequence may be of any length, for example between 2 and 10,000 nucleotides in length (or any integer value there between or there above), preferably between about 100 and 1,000 nucleotides in length (or any integer there between), more preferably between about 200 and 500 nucleotides in length. A nucleic acid template may be a single stranded nucleic acid, a double stranded nucleic acid. In some embodiment, the nucleic acid template comprises a nucleotide sequence, e.g., of one or more nucleotides, that corresponds to wild type sequence of the target nucleic acid, e.g., of the target position. In some embodiment, the nucleic acid template comprises a ribonucleotide sequence, e.g., of one or more ribonucleotides, that corresponds to wild type sequence of the target nucleic acid, e.g., of the target position. In some embodiment, the nucleic acid template comprises modified ribonucleotides.

Insertion of an exogenous sequence (also called a "donor sequence," donor template" or "donor"), for example, for correction of a mutant gene or for increased expression of a wild type gene can also be carried out. It will be readily apparent that the donor sequence is typically not identical to the genomic sequence where it is placed. A donor sequence can contain a non-homologous sequence flanked by two regions of homology to allow for efficient HDR at the location of interest. Additionally, donor sequences can comprise a vector molecule containing sequences that are not homologous to the region of interest in cellular chromatin. A donor molecule can contain several, discontinuous regions of homology to cellular chromatin. For example, for targeted insertion of sequences not normally present in a region of interest, said sequences can be present in a donor nucleic acid molecule and flanked by regions of homology to sequence in the region of interest.

The donor polynucleotide can be DNA or RNA, single-stranded and/or double-stranded and can be introduced into a cell in linear or circular form. See, e.g., U.S. Patent Publication Nos. 2010/0047805; 2011/0281361; 2011/0207221; and 2019/0330620. If introduced in linear form, the ends of the donor sequence can be protected (e.g., from exonucleolytic degradation) by methods known to those of skill in the art. For example, one or more dideoxynucleotide residues are added to the 3' terminus of a linear molecule and/or self-complementary oligonucleotides are ligated to one or both ends. See, for example, Chang and Wilson, Proc. Natl. Acad. Sci. USA (1987); Nehls et al., Science (1996). Additional methods for protecting exogenous polynucleotides from degradation include, but are not limited to, addition of terminal amino group(s) and the use of modified internucleotide linkages such as, for example, phosphorothioates, phosphoramidates, and O-methyl ribose or deoxyribose residues.

Accordingly, embodiments of the present invention using a donor template for repair may use a DNA or RNA, single-stranded and/or double-stranded donor template that can be introduced into a cell in linear or circular form. In embodiments of the present invention a gene-editing composition comprises: (1) an RNA molecule comprising a guide sequence to affect a double strand break in a gene prior to repair and (2) a donor RNA template for repair, the RNA molecule comprising the guide sequence is a first RNA molecule and the donor RNA template is a second RNA molecule. In some embodiments, the guide RNA molecule and template RNA molecule are connected as part of a single molecule.

A donor sequence may also be an oligonucleotide and be used for gene correction or targeted alteration of an endogenous sequence. The oligonucleotide may be introduced to the cell on a vector, may be electroporated into the cell, or may be introduced via other methods known in the art. The oligonucleotide can be used to 'correct' a mutated sequence in an endogenous gene (e.g., the sickle mutation in beta globin), or may be used to insert sequences with a desired purpose into an endogenous locus.

A polynucleotide can be introduced into a cell as part of a vector molecule having additional sequences such as, for example, replication origins, promoters and genes encoding antibiotic resistance. Moreover, donor polynucleotides can be introduced as naked nucleic acid, as nucleic acid complexed with an agent such as a liposome or poloxamer, or can be delivered by recombinant viruses (e.g., adenovirus, AAV, herpesvirus, retrovirus, lentivirus and integrase defective lentivirus (IDLV)).

The donor is generally inserted so that its expression is driven by the endogenous promoter at the integration site, namely the promoter that drives expression of the endogenous gene into which the donor is inserted. However, it will be apparent that the donor may comprise a promoter and/or enhancer, for example a constitutive promoter or an inducible or tissue specific promoter.

The donor molecule may be inserted into an endogenous gene such that all, some or none of the endogenous gene is expressed. For example, a transgene as described herein may be inserted into an endogenous locus such that some (N-terminal and/or C-terminal to the transgene) or none of the endogenous sequences are expressed, for example as a fusion with the transgene. In other embodiments, the transgene (e.g., with or without additional coding sequences such as for the endogenous gene) is integrated into any endogenous locus, for example a safe-harbor locus, for example a CCR5 gene, a CXCR4 gene, a PPP1R12c (also known as AAVS1) gene, an albumin gene or a Rosa gene. See, e.g., U.S. Pat. Nos. 7,951,925 and 8,110,379; U.S. Publication Nos. 2008/0159996; 20100/0218264; 2010/0291048; 2012/0017290; 2011/0265198; 2013/0137104; 2013/0122591; 2013/0177983 and 2013/0177960 and U.S. Provisional Application No. 61/823,689).

When endogenous sequences (endogenous or part of the transgene) are expressed with the transgene, the endogenous sequences may be full-length sequences (wild type or mutant) or partial sequences. Preferably the endogenous sequences are functional. Non-limiting examples of the function of these full length or partial sequences include increasing the serum half-life of the polypeptide expressed by the transgene (e.g., therapeutic gene) and/or acting as a carrier.

Furthermore, although not required for expression, exogenous sequences may also include transcriptional or translational regulatory sequences, for example, promoters, enhancers, insulators, internal ribosome entry sites, sequences encoding 2A peptides and/or polyadenylation signals.

In certain embodiments, the donor molecule comprises a sequence selected from the group consisting of a gene encoding a protein (e.g., a coding sequence encoding a protein that is lacking in the cell or in the individual or an alternate version of a gene encoding a protein), a regulatory sequence and/or a sequence that encodes a structural nucleic acid such as a microRNA or siRNA.

For the foregoing embodiments, each embodiment disclosed herein is contemplated as being applicable to each of the other disclosed embodiment. For example, it is understood that any of the RNA molecules or compositions of the present invention may be utilized in any of the methods of the present invention.

As used herein, all headings are simply for organization and are not intended to limit the disclosure in any manner. The content of any individual section may be equally applicable to all sections.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination or as suitable in any other described embodiment of the invention. Certain features described in the context of various embodiments are not to be considered essential features of those embodiments, unless the embodiment is inoperative without those elements.

Generally, the nomenclature used herein, and the laboratory procedures utilized in the present invention include molecular, biochemical, microbiological and recombinant DNA techniques. Such techniques are thoroughly explained in the literature. See, for example, Sambrook et al., “Molecular Cloning: A laboratory Manual” (1989); Ausubel, R. M. (Ed.), “Current Protocols in Molecular Biology” Volumes I-III (1994); Ausubel et al., “Current Protocols in Molecular Biology”, John Wiley and Sons, Baltimore, Maryland (1989); Perbal, “A Practical Guide to Molecular Cloning”, John Wiley & Sons, New York (1988); Watson et al., “Recombinant DNA”, Scientific American Books, New York; Birren et al. (Eds.), “Genome Analysis: A Laboratory Manual Series”, Vols. 1-4, Cold Spring Harbor Laboratory Press, New York (1998); Methodologies as set forth in U.S. Pat. Nos. 4,666,828; 4,683,202; 4,801,531; 5,192,659 and 5,272,057; Cellis, J. E. (Ed.), “Cell Biology: A Laboratory Handbook”, Volumes I-III (1994); Freshney, “Culture of Animal Cells—A Manual of Basic Technique” Third Edition, Wiley-Liss, N. Y. (1994); Coligan J. E. (Ed.), “Current Protocols in Immunology” Volumes I-III (1994); Stites et al. (Eds.), “Basic and Clinical Immunology” (8th Edition), Appleton & Lange, Norwalk, C T (1994); Mishell and Shiigi (Eds.), “Strategies for Protein Purification and Characterization—A Laboratory Course Manual” CSHL Press (1996); Clokie and Kropinski (Eds.), “Bacteriophage Methods and Protocols”, Volume 1: Isolation, Characterization, and Interactions (2009), all of which are incorporated by reference. Other general references are provided throughout this document.

Examples are provided below to facilitate a more complete understanding of the invention. The following examples illustrate the exemplary modes of making and practicing the invention. However, the scope of the invention is not limited to specific embodiments disclosed in these Examples, which are for purposes of illustration only.

EXPERIMENTAL DETAILS

Examples are provided below to facilitate a more complete understanding of the invention. The following examples illustrate the exemplary modes of making and practicing the invention. However, the scope of the invention is not limited to specific embodiments disclosed in these Examples, which are for purposes of illustration only.

Example 1: OMNI-103 CRISPR Nuclease

CRISPR repeat (crRNA), trans-activating RNA (tracrRNA), nuclease polypeptide (OMNI), and protospacer adjacent motif (PAM) sequences were predicted from different metagenomic databases of sequences of environmental samples.

Construction of OMNI Nuclease Polypeptides

For construction of novel nuclease polypeptides (OMNIs), the open reading frame of several identified OMNIs were codon optimized for human cell line expression. The ORF was cloned into the bacterial expression plasmid pET9a and into the mammalian expression plasmid pmOMNI (Table 4).

Prediction and Construction of sgRNA

For each OMNI the single guide RNA (sgRNA) was predicted by detection of the CRISPR repeat array sequence and a tracrRNA in the respective bacterial genome. The native pre-mature crRNA and tracrRNA sequences were connected in silico with a tetra-loop ‘gaaa’ sequence and the secondary structure elements of the duplex were predicted using an RNA secondary structure prediction tool.

The predicted secondary structures of the full duplex RNA elements (crRNA-tracrRNA chimera) was used for identification of possible tracrRNA sequences for the design of a sgRNA. Several possible sgRNA scaffolds versions were constructed by shortening the duplex at the upper stem at different locations (OMNI-103 sgRNA designs are listed in Table 2). Additionally, to overcome potential transcriptional and structural constraints and to assess the plasticity of the sgRNA scaffold in the human cellular environmental context, small changes in the nucleotide sequence of the possible sgRNA were made in some cases (FIG. 1, Table 2). Finally, up to three versions of possible designed scaffolds were synthesized for each OMNI and connected downstream to a 22-nucleotide universal unique spacer sequence (T2, SEQ ID NO: 135) and cloned into a bacterial expressing plasmid under an inducible T7 promoter combined with a U6 promoter for mammalian expression (pShuttleGuide, Table 4).

```
                                   (SEQ ID NO: 135)
T2 - GGAAGAGCAGAGCCTTGGTCTC
```

In-Vitro Depletion Assay by TXTL

Figure 4A:
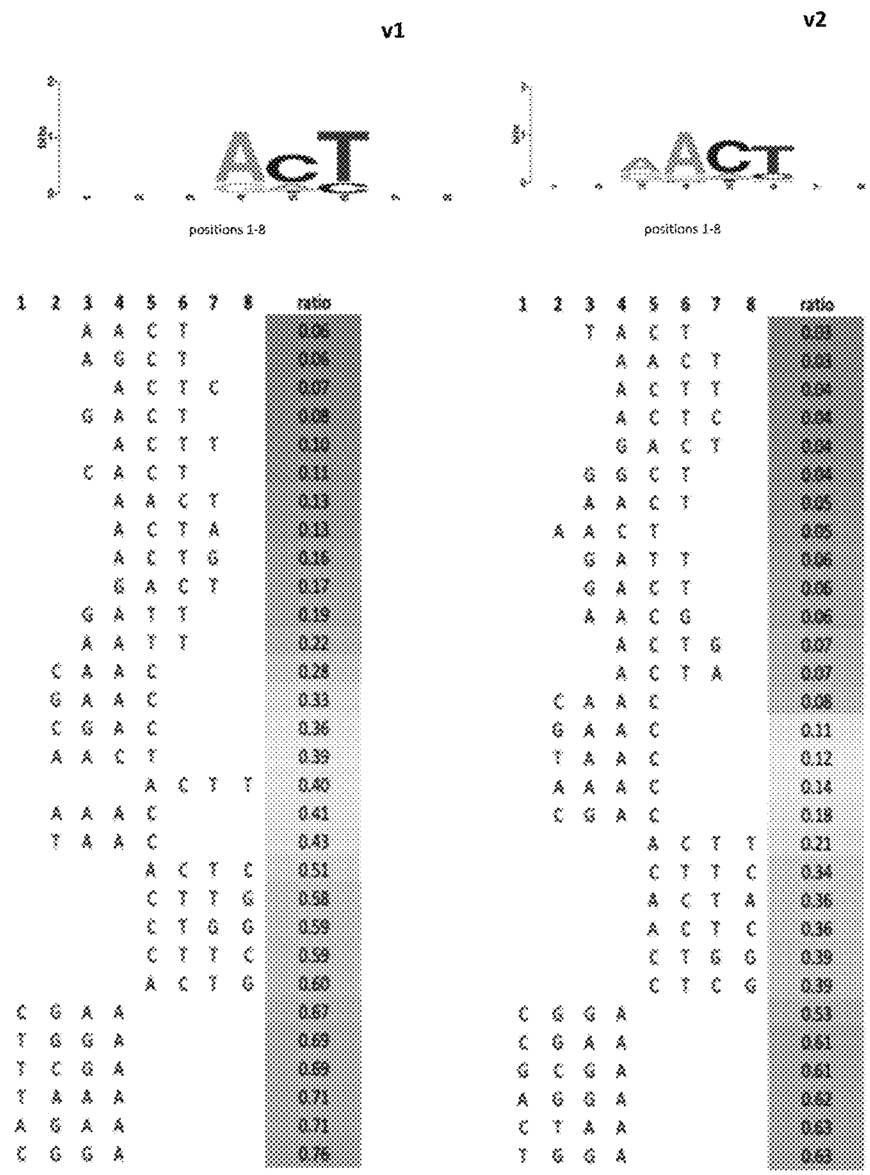
Figure 4B:
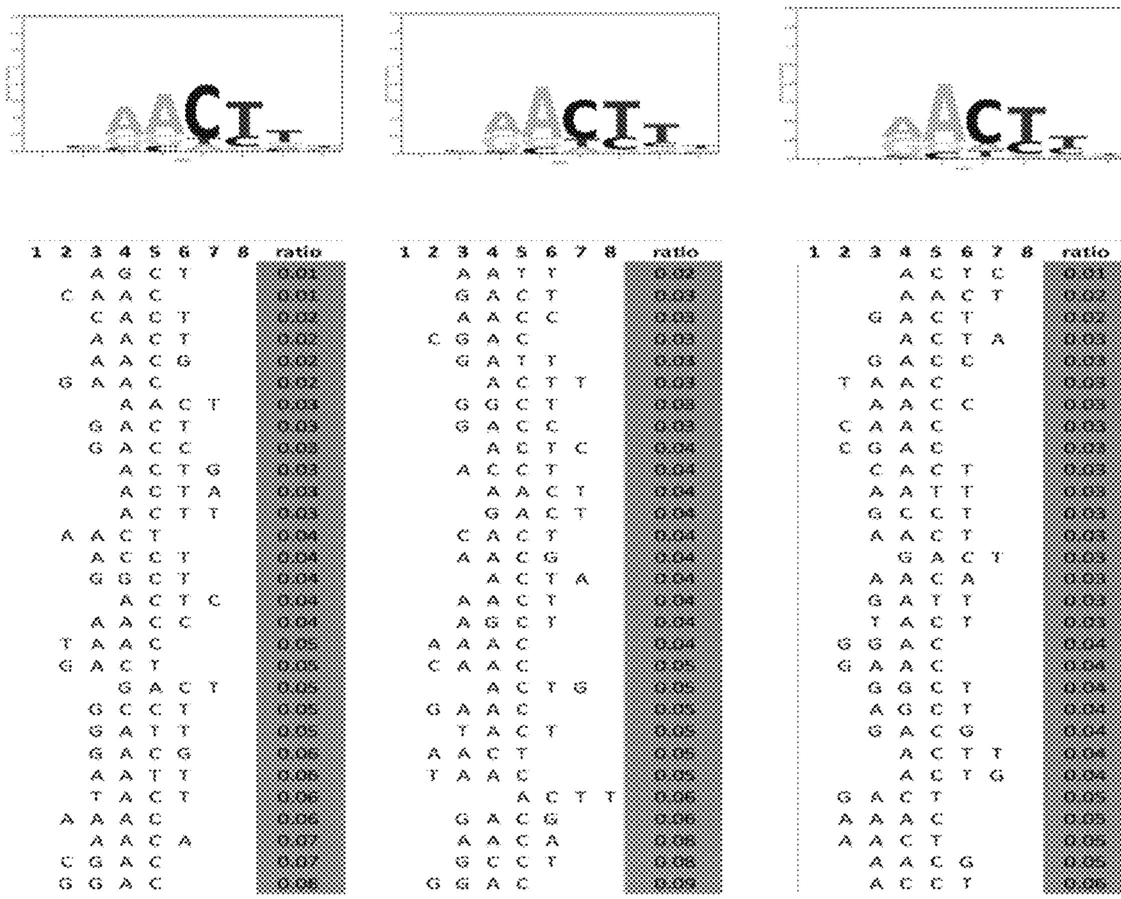
Figure 5B:
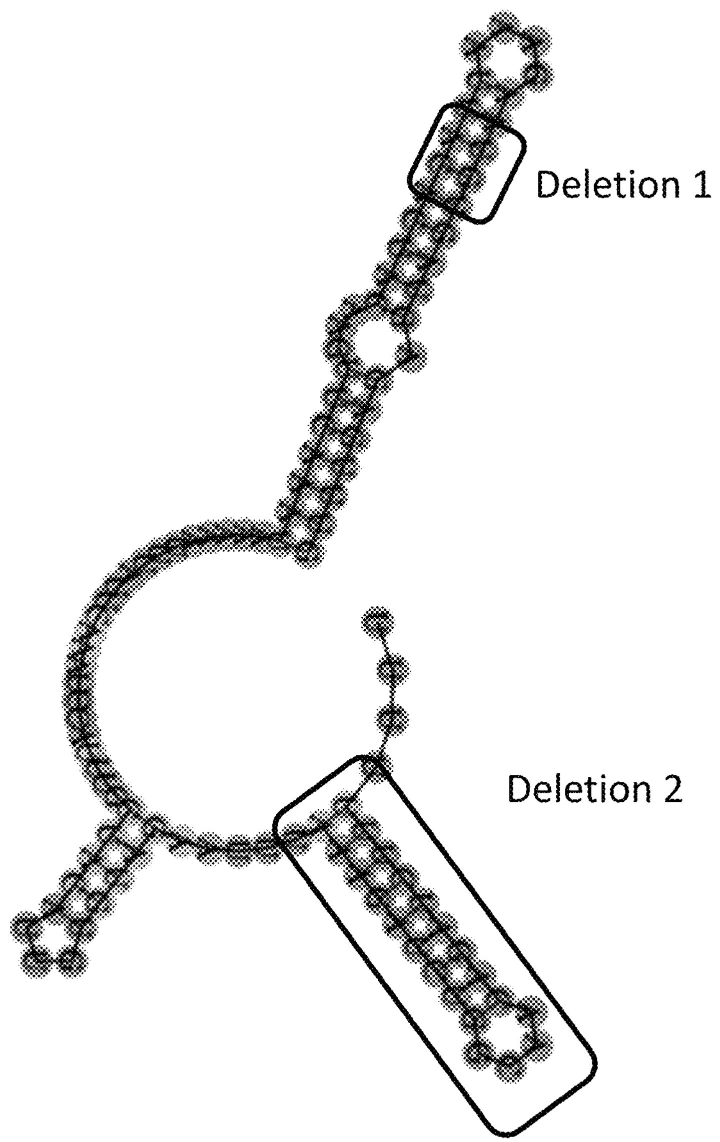
Figure 5C:
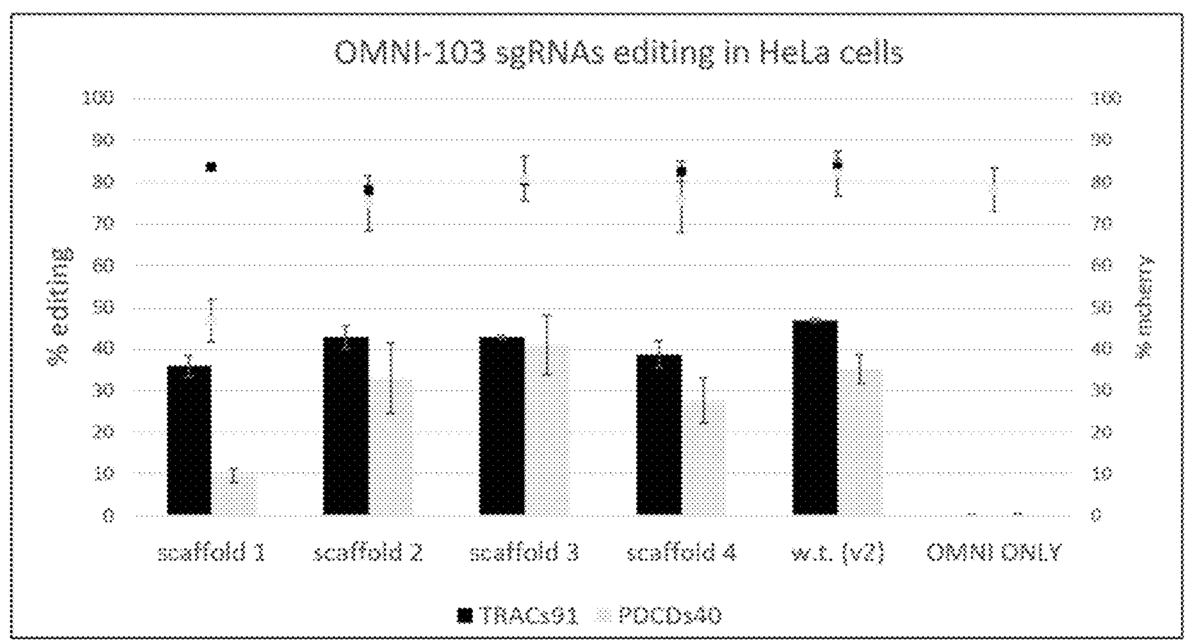
Figure 6A:
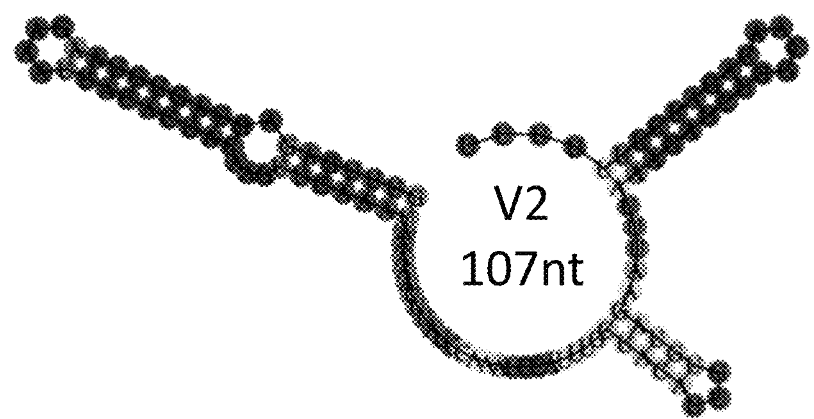
FIGS. 6A-6F. The predicted secondary structures of the sgRNA listed in Table 3.
Figure 6B:
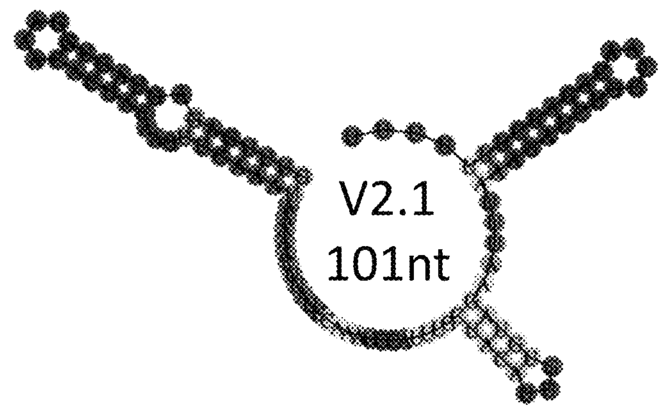
Figure 6C:
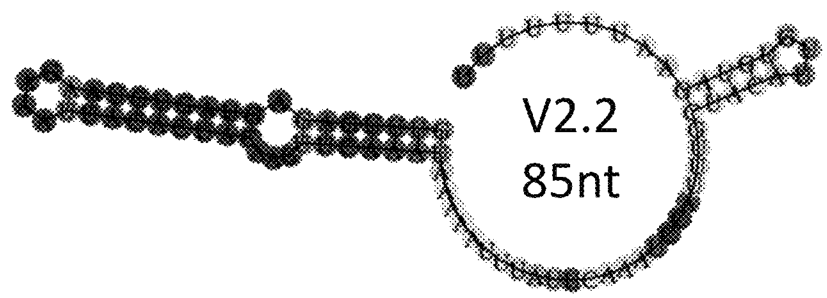
Figure 6D:
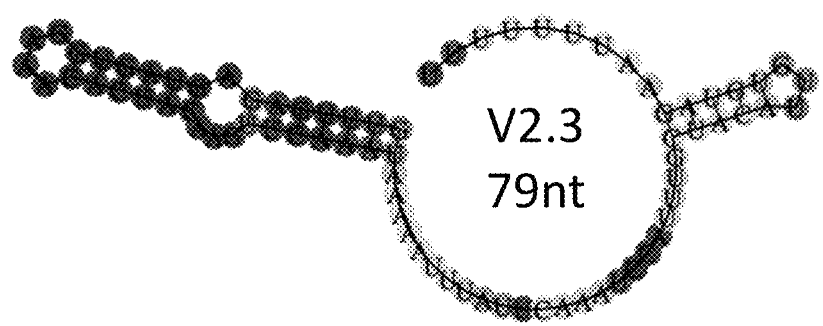
Figure 6E:
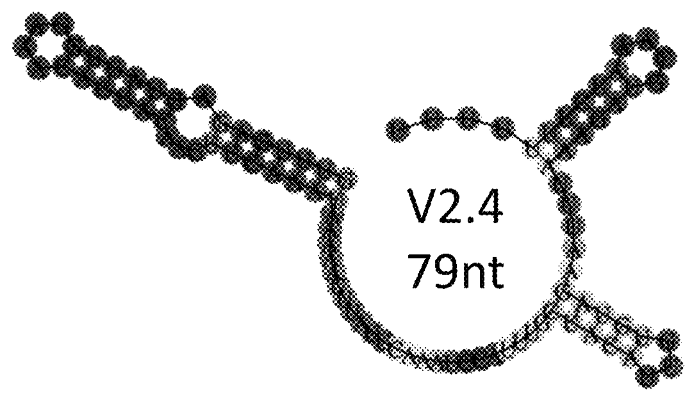
Figure 6F:
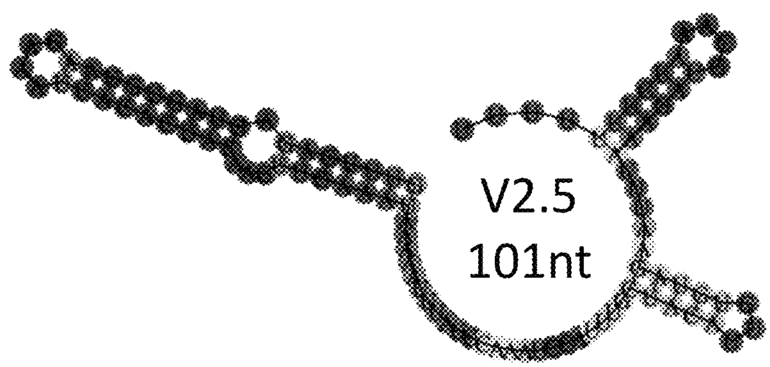

Depletion of PAM sequences in vitro was followed as described by Maxwell et al, Methods. 2018. Briefly, linear DNA expressing the OMNI nucleases and an sgRNA under T7 promoter were added to a cell-free transcription-translation in vitro system (TXTL mix, Arbor Bioscience) together with a linear construct expressing T7 polymerase. RNA expression and protein translation by the TXTL mix result in the formation of a ribonucleoprotein (RNP) complex. Since linear DNA was used, Chili DNA sequences were added to the TXTL reaction mix to inhibit the exonuclease activity of RecBCD, thereby protecting the linear DNA from degradation. The sgRNA spacer is designed to target a library of plasmids containing the target protospacer (pbPOS T2 library, Table 4) flanked by an 8N randomized set of potential PAM sequences. Depletion of PAM sequences from the library was measured by high-throughput sequencing using PCR to add the necessary adapters and indices to both the cleaved library and to a control library expressing a non-targeting gRNA. Following deep sequencing, the in vitro activity was confirmed by the fraction of the depleted sequences having the same PAM sequence relative to their occurrence in the control, indicating functional DNA cleavage by the OMNI nuclease (FIGS. 4A-4B and Table 3).

Activity in Human Cells on Endogenous Genomic Targets

OMNI-103 was assayed for its ability to promote editing on specific genomic locations in human cells. Editing activity on human genomic targets of OMNI-103 was assessed by NGS cleavage analysis on HeLa cells co-transfected with OMNI-103 nuclease and a panel of unique sgRNA molecules each designed to target a different genomic location. To this end, human optimized OMNI-103 nuclease was cloned into an in-frame-P2A-mCherry expression vector (pmOMNI, Table 4) and each of the OMNI-103 sgRNA molecule sequences were cloned into a shuttle-guide vector (pShuttle Guide, Table 4). The sgRNA molecules were designed to contain a 22-nucleotide guide sequence portion that targets a specific location in the human genome (Table 5) according to the corresponding OMNI-103 PAM preference, followed by the sgRNA scaffold sequence as discovered by TXTL (Table 3). At 72 hours post-transfection, cells were harvested. Half of the harvested cells were used for quantification of the OMNI-103 nuclease expression by FACS using mCherry fluorescence as a marker. The rest of the cells were lysed, and their genomic DNA content was extracted and used as a template for PCR amplification of the corresponding genomic targets. Amplicons were subjected to next generation sequencing (NGS) and the resulting reads were then used to calculate the percentage of editing events in their target sites. Short insertions or deletions (indels) around the cut site are the typical outcome of repair of DNA ends following nuclease-induced DNA cleavage. The calculation of % editing was deduced from the fraction of indel reads relative to the total aligned reads within each amplicon. As can be seen in Table 5 (column 5, "% editing"), OMNI-103 nuclease exhibited high and significant editing levels on most genomic sites.

Protein Purification of OMNI-103 Nuclease

The expression method for nuclease protein production and synthetic guide production for use in RNP assembly was described in U.S. Provisional Application No. 63/286,855. Briefly, OMNI-103 nuclease open reading frame was codon optimized for bacteria (Table 1) and cloned into modified pET9a plasmid with the following elements—SV40 NLS-OMNI-103 ORF bacterial optimized (from 2$^{nd}$ amino acid)—HA tag-SV40 NLS-8 His-tag (Table 4). The OMNI-103 construct was expressed in KRX cells (PROMEGA). Cells were grown in TB+0.4% Glycerol with addition of 6.66 mM Rhamnose (26.4 ml from 0.5M stock), and 0.05% glucose (2 ml from 0.5M), and expressed in mid-log phase for 4 hr upon temperature reduction to 20° C. Cells were lysed using chemical lysis and cleared lysate was purified on Ni-NTA resin. The Ni-NTA elution fraction was purified on CEX (S03 fractogel) resin followed by SEC purification on Superdex® 200 Increase 10/300 GL, AKTA Pure (GE Healthcare Life Sciences). Fractions containing OMNI-103 protein were pooled and concentrated to 30 mg/ml stocks and flash-frozen in liquid nitrogen and stored at −80° C.

OMNI-103 Cleavage Activity of RNP In Vitro

Synthetic sgRNAs of OMNI-103 were synthesized with three 2'-O-methyl 3'-phosphorothioate at the 3' and 5' ends (Agilent).

Figure 2A:
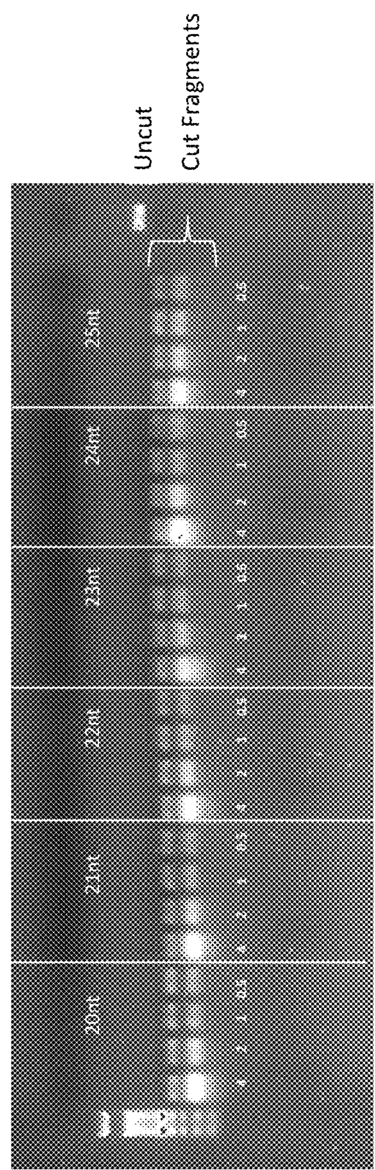
FIG. 2A-2C: OMNI-103 activity and spacer optimization as RNP in U2OS cells. OMNI-103 nuclease was over-expressed and purified. The purified protein was complexed with synthetic sgRNA to form RNPs.

Activity of OMNI-103 RNP was assayed in vitro with guide molecules having different spacer lengths (20-25 nucleotides) that target the same target site as guide PDCD1 S40 (Table 6, FIG. 2A). Briefly, 10 pmol of OMNI-103 nuclease were mixed with 20 pmol of synthetic guide. After a 10-minute incubation at room temperature, the RNP complexes were serial diluted to 4, 2, 1, 0.5 pmol and reacted with a 40 ng of linear DNA template prepared by amplification of the PDCD1 S40 target site from extracted genomic DNA. All spacer length (20-25 nucleotides) showed full cleavage of the PDCD1 template in all RNP concentrations indicating high cleavage activity (FIG. 2A).

Figure 2B:
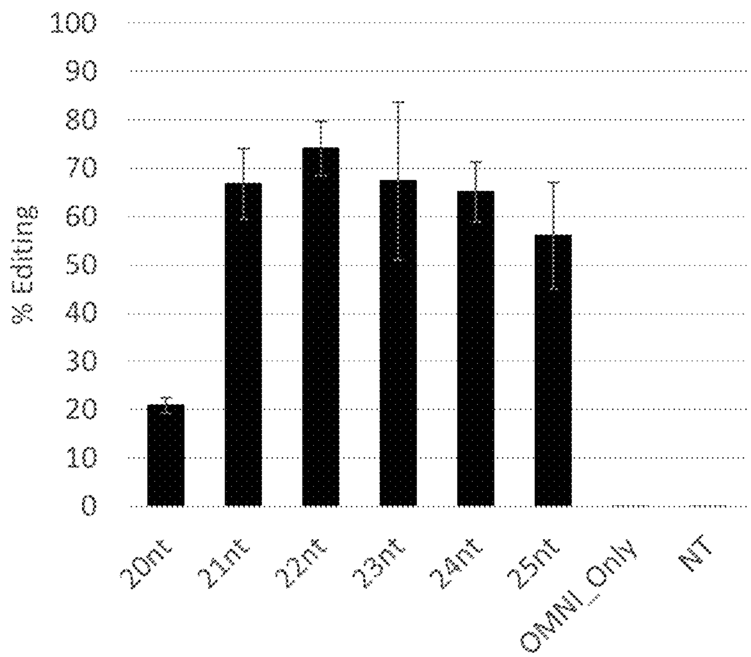

Guide Optimization for OMNI-103 Nuclease by Measuring Editing Activity of RNPs in U2OS Cells Spacer length optimization was also tested in a mammalian cell context. RNPs were assembled by mixing 100 uM OMNI-103 nuclease with 120 uM of synthetic guides of different spacer lengths (20-25 nucleotides, Table 6) and 100 uM Cas9 electroporation enhancer (IDT). After a 10-minute incubation at room temperature, the RNP complexes were mixed with 200,000 pre-washed U2OS cells and electroporated using Lonza SE Cell Line 4D-Nucleofector™ X Kit with DN100 according to the manufacture's protocol. 72 hours post-electroporation, cells were lysed, and their genomic DNA content was extracted. The corresponding genomic target sites were then amplified by PCR. Amplicons were subjected to NGS and the resulting sequences were used to calculate the percentage of editing events. As can be seen in FIG. 2B and Table 7, the spacer length of 22 nucleotides showed the highest editing level.

OMNI-103 RNP Editing Activity in Human Cells

Figure 2C:
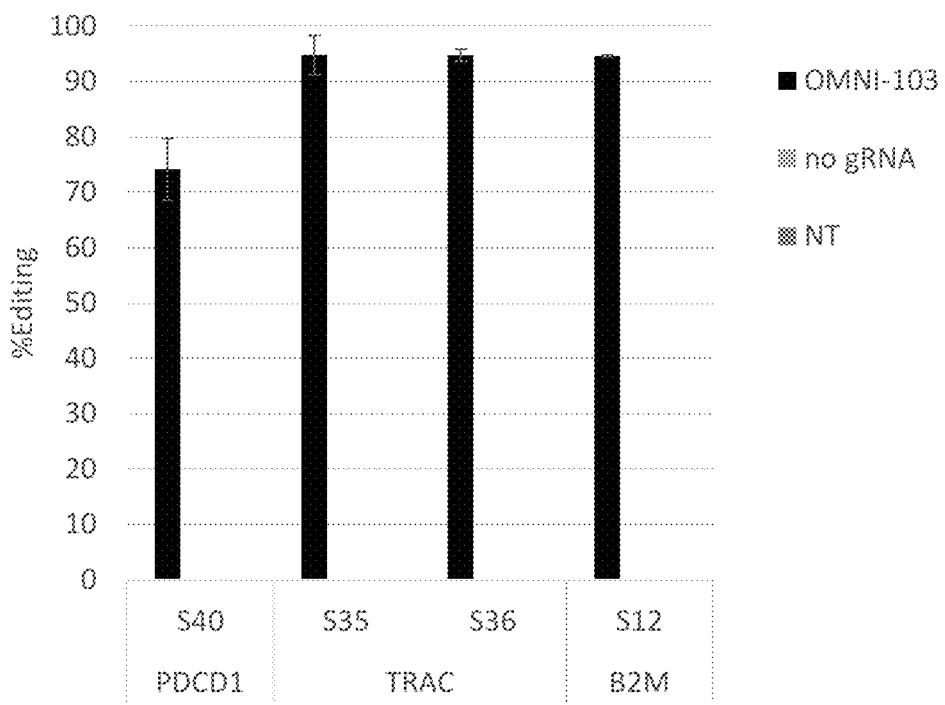

Activity of OMNI-103 protein as RNP in mammalian cells was observed in U2OS (Table 7, FIG. 2C) and comparable activity was also observed in T cells (Table 8). RNPs were assembled by mixing 100 uM nuclease with 120 uM of synthetic guide (Table 6) and 100 uM Cas9 electroporation enhancer (IDT). After a 10-minute incubation at room temperature, the RNP complexes were mixed with 200,000 U2OS cells and electroporated using Lonza SE Cell Line 4D-Nucleofector™ X Kit with DN100, according to the manufacture's protocol. 72 hours post-electroporation, cells were lysed, and their genomic DNA content was extracted. The corresponding genomic target sites were then amplified by PCR. Amplicons were subjected to NGS and the resulting sequences were used to calculate the percentage of editing events. OMNI-103 RNPs were tested with PDCD1 S40, TRAC S35, TRAC S36 and B2M S12 guides. All four (4) guides tested showed 70-90% editing levels (FIG. 2C).

Evaluating Off-Target Effects Using Guide-Seq Unbiased Analysis Method

Guide-seq allows for the unbiased in vitro detection of off-target genome editing events caused by CRISPR nucleases in living cells. Blunt-ended CRISPR RNA-guided nuclease (RGN) induced DSBs in the genomes of living human cells are tagged by integration of a blunt double-stranded oligodeoxynucleotide (dsODN) at these breaks via an end-joining process consistent with NHEJ. dsODN integration sites in genomic DNA are precisely mapped at the nucleotide level using unbiased amplification and deep NGS. After genomic DNA sonication and a series of adapter ligations, the oligonucleotide-containing libraries are subjected to high-throughput DNA sequencing and the output processed with the default Guide-seq software to identify the site of oligonucleotide capture.

To evaluate the specificity of OMNI-103 nuclease, Guide-seq was used to generate an unbiased survey of the off-target cleavage across the genome of human U2OS cells using the PDCD1 S40 and TRAC S35 sites (Table 6).

Figures 3A, 3B:
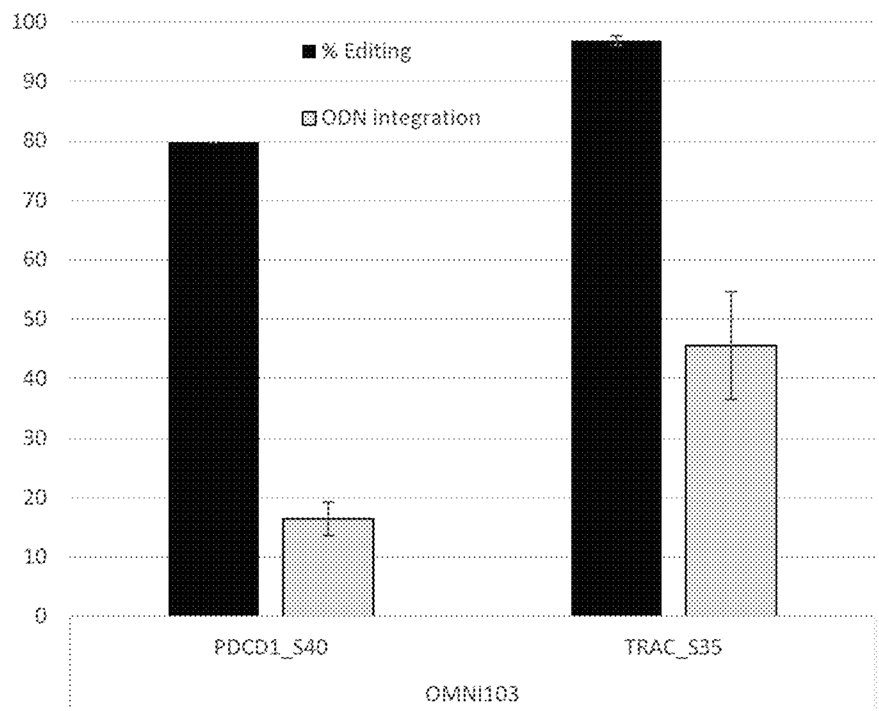
FIGS. 3A-3B. OMNI-103 off targets analysis by an unbiased biochemical assay (guide-seq). RNPs with PDCD1 S40 and TRAC S35 guide molecules (Table 6) were mixed with dsODN and electroporated into U2OS cell line.

RNPs were assembled by mixing 100 uM nuclease with 120 uM of synthetic guide and 100 uM Cas9 electroporation enhancer (IDT). After a 10-minute incubation at room temperature, the RNP complexes were mixed with 100 uM dsODN and 200,000 pre-washed U2OS cells. The cells were electroporated using Lonza SE Cell Line 4D-Nucleofector™ X Kit with DN100 according to the manufacture's protocol. 72 hours post-electroporation, cells were lysed, and their genomic DNA content was extracted. The corresponding genomic target sites were then amplified by PCR. Amplicons were subjected to NGS and the resulting sequences were then used calculate the percentage of editing events and the dsODN integration (FIG. 3A). OMNI-103 did not show any off-target effects at the PDCD1 S40 and TRAC S35 sites (FIG. 3B).

TABLE 1

OMNI CRISPR nuclease sequences

| "OMNI" Name | SEQ ID NO of OMNI Amino Acid Sequence | SEQ ID NO of DNA sequence encoding OMNI | SEQ ID NO of DNA sequence codon optimized for expression in human cells | Nickase having inactivated RuvC domain | Nickase having inactivated HNH domain | Dead nuclease having inactivated RuvC and HNH domains |
|---|---|---|---|---|---|---|
| OMNI-103 | 1 | 2 | 3 | (D12, E776, H988, or D991) | (D856*, H857, or N880) | (D12, E776, H988, or D991) and (D856*, H857, or N880) |

Table 1. OMNI nuclease sequences: Table 1 lists the OMNI name, its corresponding nuclease protein sequence, its DNA sequence, its human optimized DNA sequence, alternative positions to be substituted to generate a nickase having an inactivated RuvC domain, alternative positions to be substituted to generate a nickase having an inactivated HNH domain, and alternative positions to be substituted to generate a catalytically dead nuclease having inactivated RuvC and HNH domains. Substitution to any other amino acid is permissible for each of the amino acid positions indicated in columns 5-7, except if followed by an asterisk, which indicates that any substitution other than aspartic acid (D) to glutamic acid (E) or glutamic acid (E) to aspartic acid (D) results in inactivation.

SUPPLEMENTAL TABLE 1

OMNI-103 Domains

| | OMNI-103 DOMAIN | | | | | | | | | |
|---|---|---|---|---|---|---|---|---|---|---|
| | A | B | C | D | E | F | G | H | I | J |
| Amino Acid Range | 1-45 | 46-83 | 84-158 | 159-302 | 303-515 | 516-727 | 728-778 | 779-923 | 924-1068 | 1069-1348 |

Supplemental Table 1. OMNI Domains: Supplemental Table 1 lists the amino acid range of each identified domain for OMNI CRISPR nuclease. For example, Domain G of OMNI-103 is identified by amino acids 728 to 778 of SEQ ID NO: 1. The listed amino acid ranges are based on a preferred analysis of a local alignment generated using the Smith-Waterman algorithm, however, the beginning or end of each domain range may increase or decrease by up to five amino acids.

TABLE 2

| OMNI Guide RNA and Scaffold RNA Sequences | | |
|---|---|---|
| | | OMNI-103 with sgRNA 12 |
| crRNA:tracrRNA duplex V1 | crRNA (Repeat) | GUUUGAGAGUAGUGUAA (SEQ ID NO: 4) |
| | Partial crRNA 1 | GUUUGAGAGUAGUGU (SEQ ID NO: 5) |
| | Partial crRNA 2 | GUUUGAGAGUAG (SEQ ID NO: 6) |
| | Partial crRNA 3 | GUUUGAGAGU (SEQ ID NO: 7) |
| | tracrRNA (Antirepeat) | UUACACUACAAGUUCAAAU (SEQ ID NO: 8) |
| | Partial tracrRNA 1 | ACACUACAAGUUCAAAU (SEQ ID NO: 9) |
| | Partial tracrRNA 2 | CUACAAGUUCAAAU (SEQ ID NO: 10) |
| | Partial tracrRNA 3 | ACAAGUUCAAAU (SEQ ID NO: 11) |
| tracrRNA sequences | tracrRNA Portion 1 | AAAAAUUUAUUCAAAUCCUUUUGCUACAUUG UGUAGAAUUU (SEQ ID NO: 12) |
| | tracrRNA Portion 2 | AAAGAUCUGGCAACAGAUCUUUUUUU (SEQ ID NO: 13) |
| | tracrRNA Portion 2 -polyT | AAAGAUCUGGCAACAGAUC (SEQ ID NO: 14) |
| sgRNA Versions | sgRNA V1 | GUUUGAGAGUAGUGUAAgaaaUUACACUACAAG UUCAAAUAAAAAUUUAUUCAAAUCCUUUUGC UACAUUGUGUAGAAUUUAAAGAUCUGGCAAC AGAUCUUUUUUU (SEQ ID NO: 15) |
| | sgRNA V2 | GUUUGAGAGUAGUGUAAgaaaUUACACUACAAG UUCAAAUAAAAAUUUAUUCAAAUCCAUUUGC UACAUUGUGUAGAAUUUAAAGAUCUGGCAAC AGAUCUUUUUUU (SEQ ID NO: 16) |
| | sgRNA V2 Modified tracrRNA Portion 2 | AAAAAUUUAUUCAAAUCCAUUUGCUACAUUG UGUAGAAUUU (SEQ ID NO: 17) |
| | | OMNI-103 with sgRNA 32 |
| crRNA:tracrRNA duplex V1 | crRNA (Repeat) | GUUUGAGAGUAGUGUAA (SEQ ID NO: 18) |
| | Partial crRNA 1 | GUUUGAGAGUAGUGU (SEQ ID NO: 19) |
| | Partial crRNA 2 | GUUUGAGAGUAG (SEQ ID NO: 20) |
| | Partial crRNA 3 | GUUUGAGAGU (SEQ ID NO: 21) |
| | tracrRNA (Antirepeat) | UUACACUACAAGUUCAAAU (SEQ ID NO: 22) |
| | Partial tracrRNA 1 | ACACUACAAGUUCAAAU (SEQ ID NO: 23) |
| | Partial tracrRNA 2 | CUACAAGUUCAAAU (SEQ ID NO: 24) |
| | Partial tracrRNA 3 | ACAAGUUCAAAU (SEQ ID NO: 25) |
| tracrRNA sequences | tracrRNA Portion 1 | AAAAAUUUAUUCAAAUCCUUUUGCUACAUUG UGUAGAAUUU (SEQ ID NO: 26) |
| | tracrRNA Portion 2 | AAAGAUCUGGCAACAGAUCUUUUUUAUUUUU U (SEQ ID NO: 27) |
| | tracrRNA Portion 2 -polyT | AAAGAUCUGGCAACAGAUCUUUUUUA (SEQ ID NO: 28) |
| sgRNA Versions | sgRNA V1 | GUUUGAGAGUAGUGUAAgaaaUUACACUACAAG UUCAAAUAAAAAUUUAUUCAAAUCCUUUUGC UACAUUGUGUAGAAUUUAAAGAUCUGGCAAC AGAUCUUUUUUAUUUUUU (SEQ ID NO: 29) |
| | sgRNA V2 | GUUUGAGAGUAGUGUAAgaaaUUACACUACAAG UUCAAAUAAAAAUUUAUUCAAAUCCUUUUGC UACAUUGUGUAGAAUUUAAAGAUCUGGCAAC AGAUCUUUUUU (SEQ ID NO: 30) |
| | sgRNA V3 | GUUUGAGAGUAGUGUAAgaaaUUACACUACAAG UUCAAAUAAAAAUUUAUUCAAAUCCAUUUGC UACAUUGUGUAGAAUUUAAAGAUCUGGCAAC AGAUCUUUUUU (SEQ ID NO: 31) |
| | sgRNA V3 Modified tracrRNA Portion 1 | AAAAAUUUAUUCAAAUCCAUUUGCUACAUUG UGUAGAAUUU (SEQ ID NO: 32) |

TABLE 3

| OMNI PAM Sequences showing activity for each tested sgRNA | | | | |
|---|---|---|---|---|
| | TXTL Depletion | | | |
| Name | PAM General | PAM Specific | Activity (1-Depletion score*), per respective sgRNA listed in right col. | sgRNA |
| OMNI-103 | NNRRHY or NNRVCT | NNRACT | 0.94, 0.97, 0.99, 0.98, 0.99 | sgRNA 12: V1, V2; sgRNA 32: V1, V2, V3 |

*Depletion score-Average of the ratios from two most depleted sites

TABLE 4

Plasmids and Constructs

| Plasmid | Purpose | Elements | Example |
|---|---|---|---|
| pET9a: OMNI-103 | Expressing OMNI polypeptide in the bacterial system | T7 promoter-SV40 NLS-OMNI ORF (Human optimized)-HA Tag-SV40 NLS-8XHisTag-T7 terminator | SEQ ID NO: 37 |
| pShuttle Guide: OMNI-103 V2 | Expressing OMNI sgRNA in the bacterial and human cell system | U6 promoter-T7 promoter-T2 spacer-sgRNA scaffold-T7 terminator | SEQ ID NO: 38 |
| pbPOS T2 library | Bacterial/TXTL depletion assay | T2 protospacer-8N PAM library-chloramphenicol acetyltransferase | SEQ ID NO: 39 |
| pmOMNI: OMNI-103 | Expressing OMNI polypeptide in the human cell system | CMV promoter-T7 promoter-SV40 NLS-OMNI ORF (Human optimized)-HA-SV40 NLS-P2A-mCherry-BGH poly(A) | SEQ ID NO: 40 |

TABLE 4

Appendix-Details of construct elements

| Element | Protein Sequence | DNA sequence |
|---|---|---|
| HA Tag | SEQ ID NO: 41 | SEQ ID NO: 45 |
| NLS | SEQ ID NO: 42 | SEQ ID NO: 46 |
| P2A | SEQ ID NO: 43 | SEQ ID NO: 47 |
| mCherry | SEQ ID NO: 44 | SEQ ID NO: 48 |

TABLE 5

OMNI-103 Nuclease activity in endogenous context in mammalian cells

| Gene Target | Corresponding Spacer Name | Spacer Sequence | PAM Sequence | % Indels |
|---|---|---|---|---|
| B2M | OMNI-103_B2M_s11-ref | SEQ ID NO: 49 | GAGACTCA | 83.0% |
| B2M | OMNI-103_B2M_s12-ref | SEQ ID NO: 50 | GTGACTTT | 90.6% |
| B2M | OMNI-103_B2M_S26-ref | SEQ ID NO: 51 | TCAACTTC | 90.5% |
| B2M | OMNI-103_B2M_S27-ref | SEQ ID NO: 52 | CAGACTTG | 58.2% |
| B2M | OMNI-103_B2M_S40-ref | SEQ ID NO: 53 | TTAACTAT | 85.7% |
| B2M | OMNI-103_B2M_S41-ref | SEQ ID NO: 54 | AAGACTTA | 56.2% |
| B2M | OMNI-103_B2M_S48-ref | SEQ ID NO: 55 | GAAGCTGA | 58.6% |
| B2M | OMNI-103_B2M_S49-ref | SEQ ID NO: 56 | TCAGCTTC | 62.7% |
| CXCR4 | OMNI-103_CXCR4_S35-ref | SEQ ID NO: 57 | CAGACTCA | 13.0% |
| CXCR4 | OMNI-103_CXCR4_s93-ref | SEQ ID NO: 58 | AAAGCTAG | 11.0% |
| ELANE | OMNI-103_ELANE_g114-ref | SEQ ID NO: 59 | TAGACTCC | 13.0% |
| ELANE | OMNI-103_ELANE_g115-alt | SEQ ID NO: 60 | GGGACTCC | 38.0% |

TABLE 5-continued

OMNI-103 Nuclease activity in endogenous context in mammalian cells

| Gene Target | Corresponding Spacer Name | Spacer Sequence | PAM Sequence | % Indels |
|---|---|---|---|---|
| ELANE | OMNI-103_ELANE_g128-ref | SEQ ID NO: 61 | CGGACTGC | 12.0% |
| PDCD1 | OMNI-103_PDCD1_S40-ref | SEQ ID NO: 62 | TAAACTGG | 53.0% |
| PDCD1 | OMNI-103_PDCD1_S92-ref | SEQ ID NO: 63 | AGGACTGC | 21.0% |
| SAMD9 | OMNI-103_SAMD9_g34-ref | SEQ ID NO: 64 | TCAACTCT | 54.4% |
| SAMD9 | OMNI-103_SAMD9_g36-ref | SEQ ID NO: 65 | TTGACTTA | 11.9% |
| SAMD9L | OMNI-103_SAMD9L_g133-alt | SEQ ID NO: 66 | CAAACTGA | 49.0% |
| SAMD9L | OMNI-103_SAMD9L_g79-alt | SEQ ID NO: 67 | TGAACTGA | 56.0% |
| SAMD9L | OMNI-103_SAMD9L_g80-alt | SEQ ID NO: 68 | AGAACTAC | 76.0% |
| SARMI | OMNI-103_SARMI_g42-ref | SEQ ID NO: 69 | CCAACTCC | 33.2% |
| SARMI | OMNI-103_SARM1_g43-ref | SEQ ID NO: 70 | GCAACTGC | 13.0% |
| SARMI | OMNI-103_SARM1_g44-ref | SEQ ID NO: 71 | AAGACTGC | 27.0% |
| SARMI | OMNI-103_SARM1_g45-ref | SEQ ID NO: 72 | GGAACTCA | 43.4% |
| TRAC | OMNI-103_TRAC S124-ref | SEQ ID NO: 73 | GGAACTTT | 69.8% |
| TRAC | OMNI-103_TRAC_S141-ref | SEQ ID NO: 74 | TAAACTTT | 86.9% |
| TRAC | OMNI-103_TRAC S142-ref | SEQ ID NO: 75 | GCCACTTT | 39.8% |
| TRAC | OMNI-103_TRAC_S24-ref | SEQ ID NO: 76 | TGGACTTC | 89.6% |
| TRAC | OMNI-103_TRAC_S35-ref | SEQ ID NO: 77 | GAGACTCT | 79.8% |
| TRAC | OMNI-103_TRAC_S36-ref | SEQ ID NO: 78 | CAGACTTG | 83.7% |
| TRAC | OMNI-103_TRAC_S58-ref | SEQ ID NO: 79 | CCAGCTGA | 50.8% |
| TRAC | OMNI-103_TRAC_s90-ref | SEQ ID NO: 80 | AAAACTGT | 59.1% |
| TRAC | OMNI-103_TRAC S91-ref | SEQ ID NO: 81 | CTGACTTT | 57.0% |

Table 5. Nuclease activity in endogenous context in mammalian cells: OMNI-103 nuclease was expressed in mammalian cell system (HeLa) by DNA transfection together with an sgRNA expressing plasmid. Cell lysates were used for site specific genomic DNA amplification and NGS. The percentage of indels was measured and analyzed to determine the editing level.

TABLE 6

Synthetic sgRNAs (spacer and scaffold) for OMNI-103

| Gene | Site | Spacer Length | Spacer Sequence | PAM | Scaffold | Full sgRNA |
|---|---|---|---|---|---|---|
| B2M | S12 | 22nt | SEQ ID NO: 82 | GTGACTTT | SEQ ID NO: 91 | SEQ ID NO: 100 |
| TRAC | S36 | 22nt | SEQ ID NO: 83 | CAGACTTG | SEQ ID NO: 92 | SEQ ID NO: 101 |
| | S35 | 22nt | SEQ ID NO: 84 | GAGACTCT | SEQ ID NO: 93 | SEQ ID NO: 102 |
| PDCD1 | S40 | 25nt | SEQ ID NO: 85 | TAAACTGG | SEQ ID NO: 94 | SEQ ID NO: 103 |
| | S40 | 24nt | SEQ ID NO: 86 | TAAACTGG | SEQ ID NO: 95 | SEQ ID NO: 104 |
| | S40 | 23nt | SEQ ID NO: 87 | TAAACTGG | SEQ ID NO: 96 | SEQ ID NO: 105 |
| | S40 | 22nt | SEQ ID NO: 88 | TAAACTGG | SEQ ID NO: 97 | SEQ ID NO: 106 |
| | S40 | 21nt | SEQ ID NO: 89 | TAAACTGG | SEQ ID NO: 98 | SEQ ID NO: 107 |
| | S40 | 20nt | SEQ ID NO: 90 | TAAACTGG | SEQ ID NO: 99 | SEQ ID NO: 108 |

TABLE 7

OMNI-103 activity and spacer optimization as RNPs in U2OS cells

| Gene | Site | Spacer Sequence | PAM | Spacer Length | % Indels | STD |
|---|---|---|---|---|---|---|
| PDCD1 | S40 | SEQ ID NO: 90 | TAAACTGG | 20nt | 20.935 | 1.60513239 |
| | S40 | SEQ ID NO: 89 | TAAACTGG | 21nt | 66.77 | 7.29734198 |
| | S40 | SEQ ID NO: 88 | TAAACTGG | 22nt | 74.145 | 5.59321464 |
| | S40 | SEQ ID NO: 87 | TAAACTGG | 23nt | 67.38 | 16.3341666 |
| | S40 | SEQ ID NO: 86 | TAAACTGG | 24nt | 65.105 | 6.20132647 |
| | S40 | SEQ ID NO: 85 | TAAACTGG | 25nt | 56.055 | 11.0379369 |
| TRAC | S35 | SEQ ID NO: 84 | GAGACTCT | 22nt | 94.76 | 3.54967604 |
| | S36 | SEQ ID NO: 83 | CAGACTTG | 22nt | 94.755 | 1.08187338 |
| B2M | S12 | SEQ ID NO: 82 | GTGACTTT | 22nt | 94.635 | 0.16263456 |

Table 7. OMNI-103 RNPs were assembled with synthetic sgRNA (Agilent) and electroporated into U2OS cells. Gene name, spacer sequences, and spacer length are indicated next to the editing level (% indels) measured by NGS.

TABLE 8

FACS Results of OMNI-103 editing as RNP in primary T cells

| Gene | Genomic site | Spacer sequence | PAM | Spacer Length | % Negative | STD |
|---|---|---|---|---|---|---|
| TRAC | S35 | SEQ ID NO: 84 | GAGACTCT | 22nt | 80% | 7.786643 |
| TRAC | S36 | SEQ ID NO: 83 | CAGACTTG | 22nt | 54% | 5.433231 |
| B2M | S12 | SEQ ID NO: 82 | GTGACTTT | 22nt | 80% | 9.563636 |

Table 8. Protein expression levels of TCR and B2M in primary T cells, 3 days after electroporation of OMNI-103 with specific synthetic sgRNA molecules (Agilent) targeting either TRAC or B2M.

Example 2: Alternate OMNI-103 CRISPR Nuclease-RNA Complexes

Methods

OMNI-103 Protein Expression

Briefly, and similar to the protein expression method described above, the nuclease open reading frame was codon optimized for human cells and cloned into modified pET9a plasmid with the following elements—SV40 NLS-OMNI-103 ORF (from $2^{nd}$ amino acid human optimized)—HA tag-SV40 NLS-8 His-tag. This sequence can be found in Table 4. The OMNI-103 construct was expressed in KRX cells (Promega). Cells were grown in TB+0.4% Glycerol with the addition of 6.66 mM rhamnose (26.4 ml from 0.5M stock) and 0.05% glucose (2 ml from 0.5M). Protein was expressed in mid-log phase for 4 hr upon temperature reduction to 20° C. Cells were lysed using chemical lysis and cleared lysate was purified on Ni-NTA resin. Ni-NTA elution fraction was purified on CEX (S03 fractogel) resin followed by SEC purification on Superdex 200 Increase 10/300 GL, AKTA Pure (GE Healthcare Life Sciences). Fractions containing OMNI-103 protein were pooled and concentrated to 30 mg/ml stocks and flash-frozen in liquid nitrogen and stored at −80° C.

Synthetic sgRNA Used

All synthetic sgRNAs of OMNI-103 were synthesized with three 2'-O-methyl 3'-phosphorothioate at the 3' and 5' ends (Agilent or Synthego).

Activity in Mammalian Cell Lines

The ability of OMNI-103 to promote editing with shorter sgRNA versions was tested on specific genomic locations in human cells (Table 10). For HeLa cells, the OMNI-103-P2A-mCherry expression vector (pmOMNI, Table 4) was transfected together with the sgRNA (pShuttle guide—Table 4, spacer sequence—Table 10).

For U2OS cells, RNPs were assembled by mixing 100 uM nuclease with 120 uM of synthetic guide and 100 uM Cas9 electroporation enhancer (IDT). After 10 minutes of incubation at room-temperature, the RNP complexes were mixed with 200,000 pre-washed U2OS cells and electroporated using Lonza SE Cell Line 4D-Nucleofector™ X Kit with the DN100 program, according to the manufacture's protocol. At 72 h cells were lysed, and their genomic DNA content was used in a PCR reaction that amplified the corresponding putative genomic targets. Amplicons were subjected to NGS and the resulting sequences were then used to calculate the percentage of editing events.

For T cells, RNPs were assembled by mixing 113 uM nuclease and 160 uM of synthetic guide and incubating for 10 minutes at room temperature, RNP complexes were mixed with 200,000 primary activated T cells, and electroporated using P3 Primary Cell 4D-Nucleofector™ X Kit, with EH-115 pulse code. After three (3) days and eight (8) days cells were collected, and CD3 and the edited protein expression was measured by flow cytometry.

Results

Activity of Short Guides Across Genomic Sites and Cell Types

Figure 7:
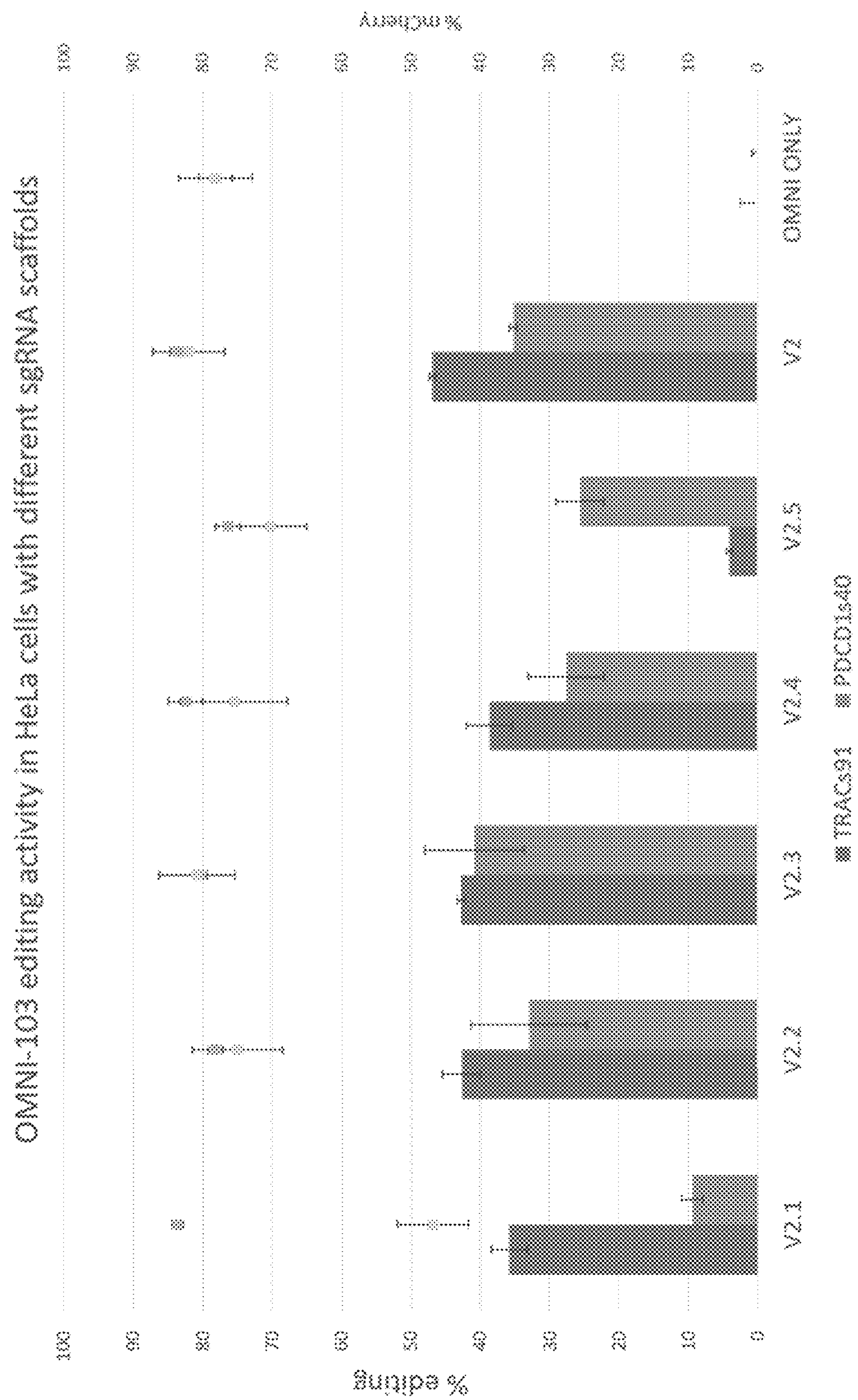
FIG. 7. OMNI-103 editing activity in HeLa cells with different sgRNA scaffolds (Table 3). Hela cells were transfected with OMNI-103 and sgRNA plasmids targeting TRAC-S91 or PDCD-S40. Editing activity was calculated based on next generation sequencing results (bars), and transfection efficiency was based on FACS analysis of the mCherry expression. Presented are the average and standard deviation of three technical replicates.
Figure 8:
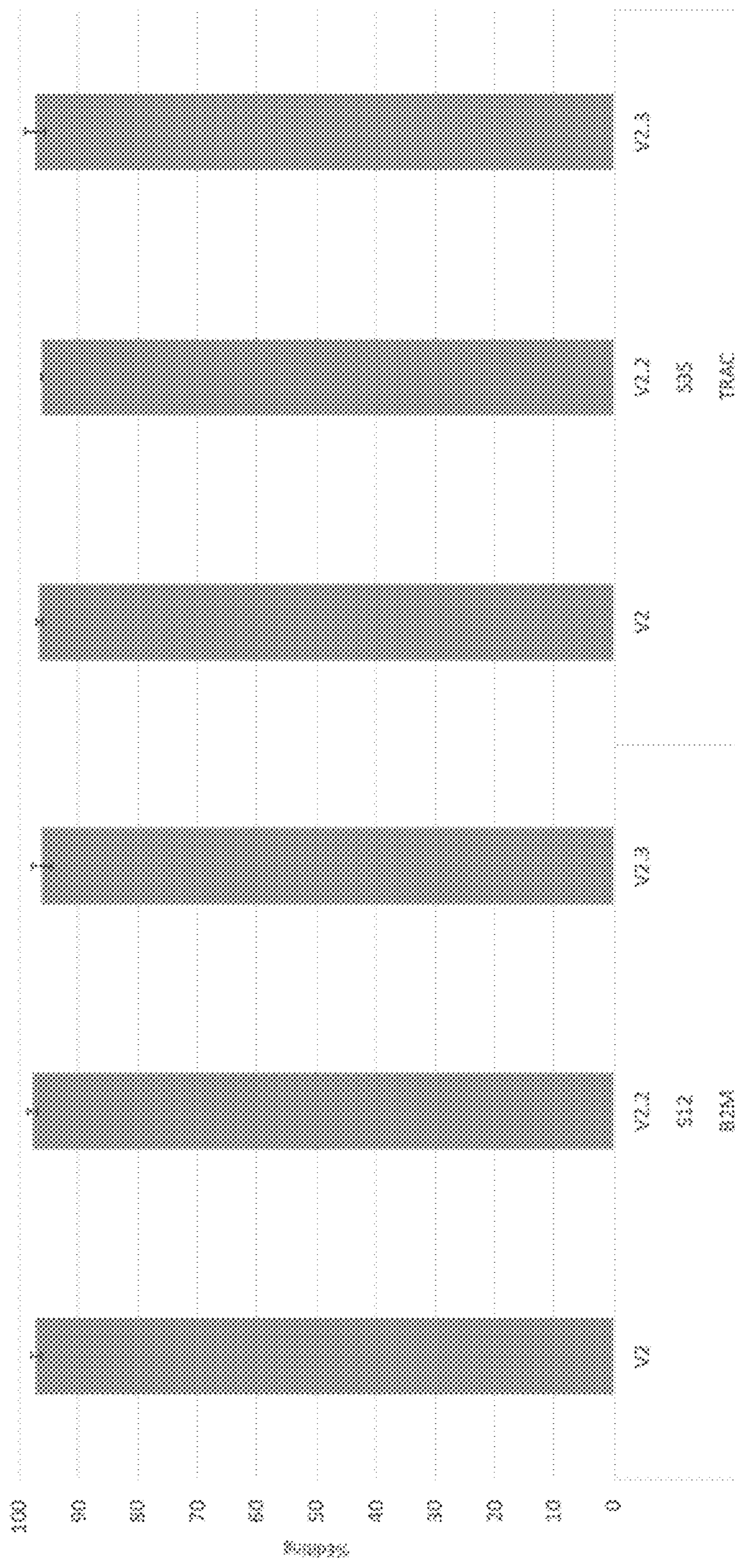
FIG. 8. Activity in U2OS. U2OS cells were electroporated with OMNI-103 and sgRNA (RNP) targeting TRAC S35 and B2M S12. Editing activity was calculated based on next generation sequencing (NGS) results. Presented are the average and standard deviation of three technical replicates.
Figure 9:
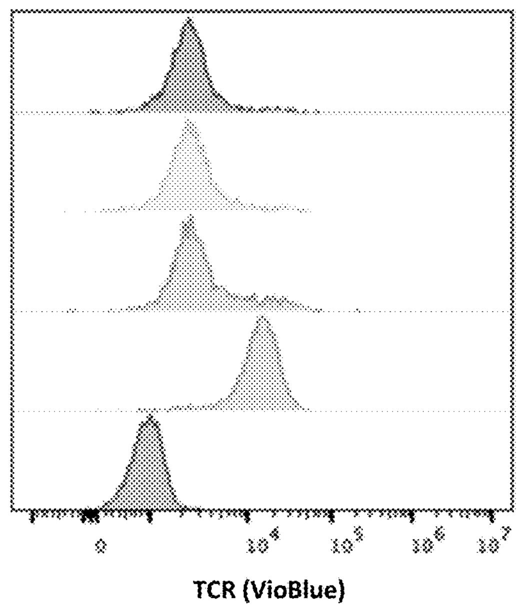
FIG. 9. Activity in primary T cells. Primary T cells were isolated from PBMCs and activated according to manufacturer's protocol (Miltenyi #130-096-535, #130-091-441). Activated T cells were electroporated with OMNI-103 and sgRNAs (RNPs) targeting TRAC-s35 and B2M-s12. After eight (8) days, cells were measured by flow cytometry for TCR and B2M expression level. For the analysis, only live and CD3-positive cells were counted. The results presented are representative and are one of three T cell donors which all showed similar results.
Figure 9:
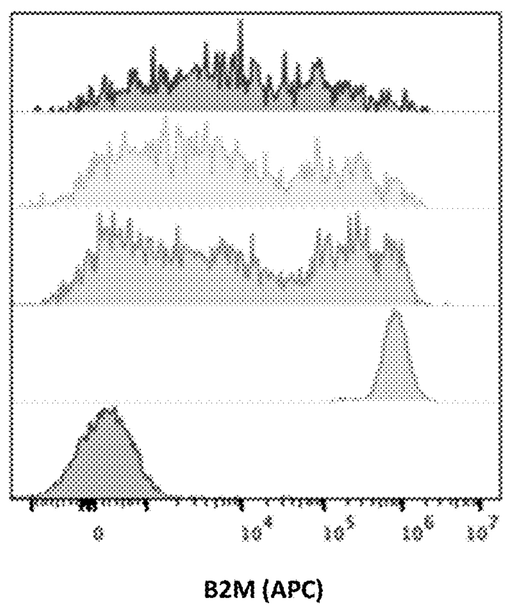
Figure 10:
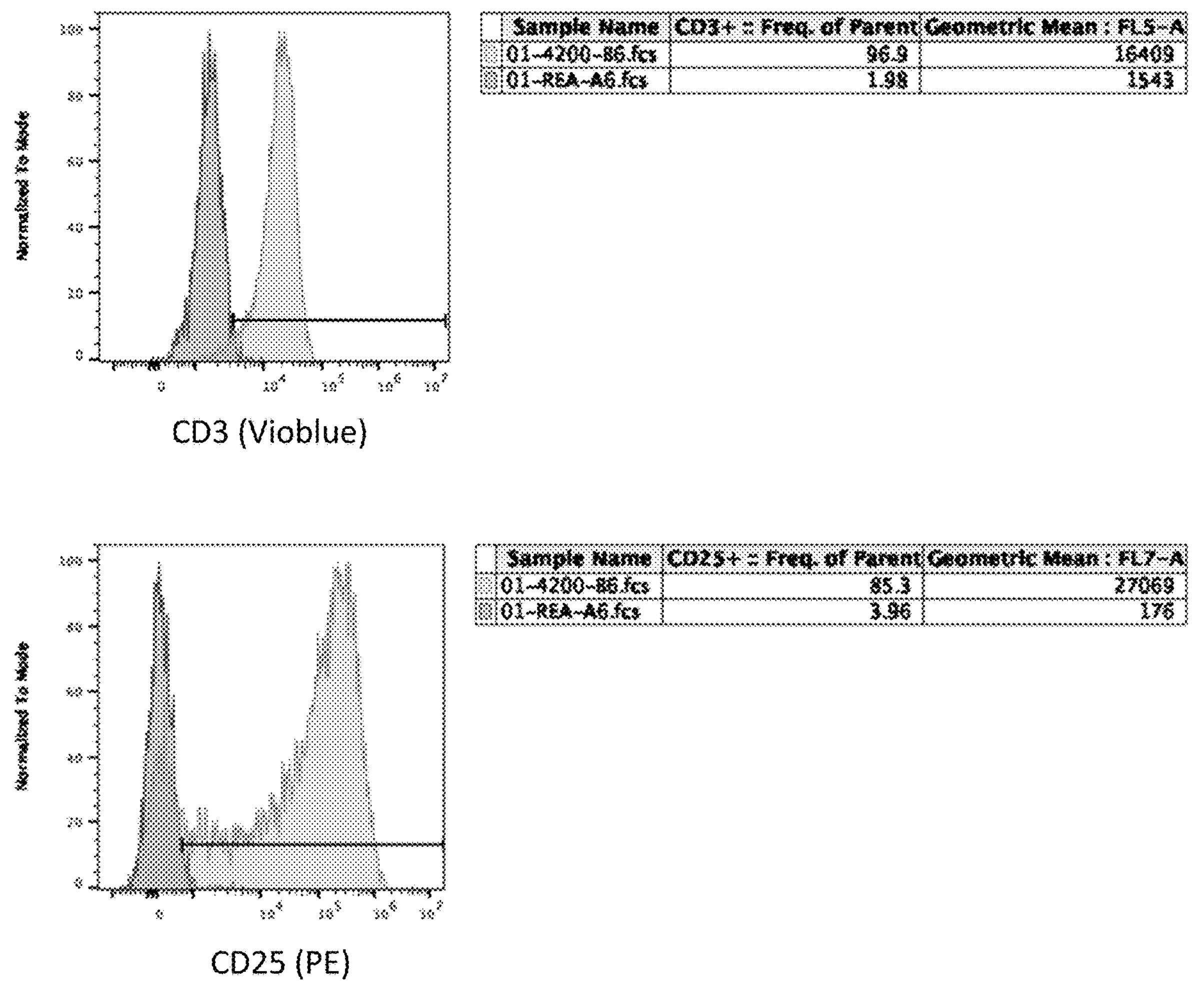
FIG. 10. T cell activation assay. Donor sample cells used in cleavage activity assay were activated with beads for 72 h and displayed an 85% primary T cell activation rate as measured by FACS ($CD3^{+}CD25^{+}$ cells).
Figure 11:
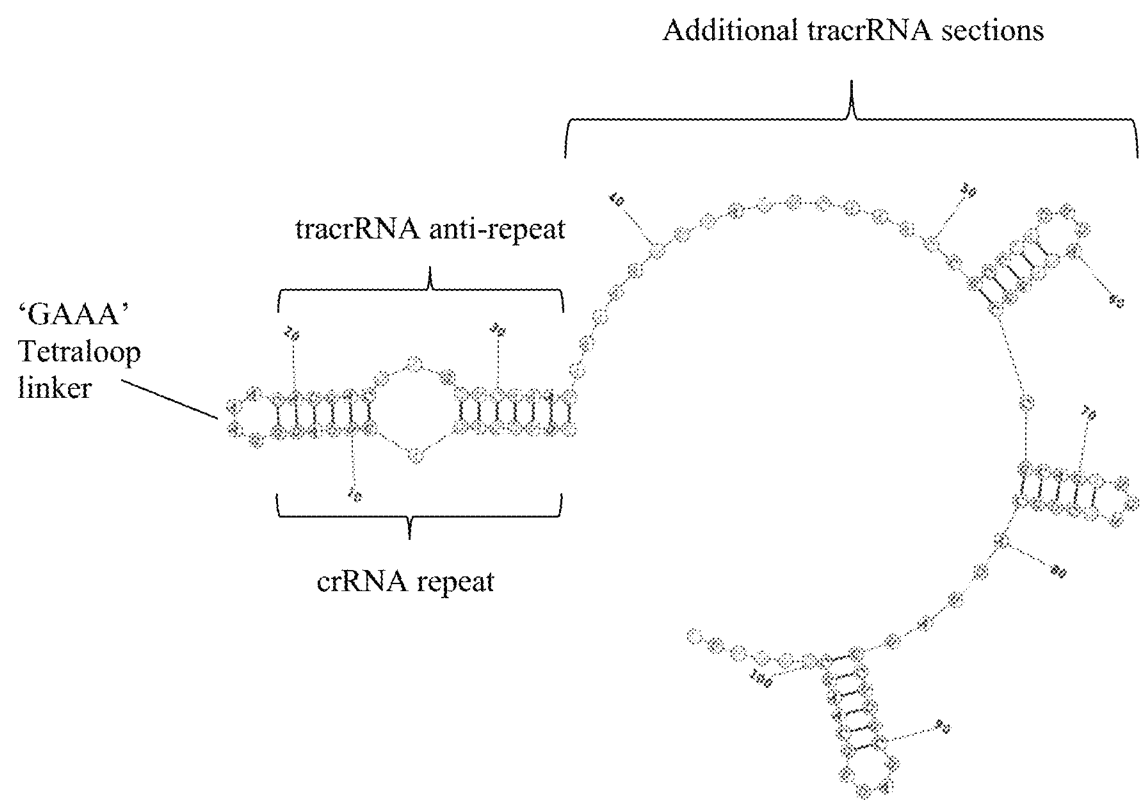
FIG. 11. Representative example of an RNA scaffold. An example RNA scaffold portion comprises a crRNA portion linked by a tetraloop to a tracrRNA portion. The crRNA portion comprises a crRNA repeat sequence. The tracrRNA portion comprises a tracrRNA anti-repeat sequence and additional tracrRNA sections. The RNA molecule may further comprise a guide sequence portion (i.e. an RNA spacer) linked to the crRNA repeat sequence, such that the RNA molecule functions as a single-guide RNA molecule.

OMNI-103 nuclease activity was optimized for use with shorter sgRNA scaffolds. Five (5) short sgRNA scaffolds were designed based on the 'V2' duplex version, which contained up to four deletions around the tetra loop "GAAA" and the terminator region (Table 9, FIGS. 6A-6F). To test the level of activity OMNI-103 displayed with the designed V2 scaffolds, sgRNAs having guide sequence portions of "TRAC-s91" or "PDCD-s40" were transfected into HeLa cells. Editing activity was calculated based on NGS results (FIG. 7). In all cases the designed sgRNA enabled editing activity. The next step was to test OMNI-103 activity as an RNP in U2OS and primary T cells. OMNI-103 was electroporated with sgRNAs having a V2, V2.2 or V2.3 scaffold and having guide sequence portions of "TRAC-s35" or "B2M-s12". Editing activity was calculated based on NGS results, and as demonstrated the level of OMNI-103 activity was not impaired when used with any of the scaffold variants (FIG. 8). In primary T cells, when the short scaffold variants were utilized, improved activity was demonstrated.

TABLE 9

OMNI-103 Designed Scaffold Sequences

| Experimental Name | Full sequence | Length |
|---|---|---|
| V2.1 | GUUUGAGAGUAGUGGAAACACUACAAGUUCAAAUAAAAAUUUAUUCAAAUCCAUUUGCUACAUUGUGUAGAAUUUAAAGAUCUGGCAACAGAUCUUUUUUU (SEQ ID NO: 33) | 101 |
| V2.2 | GUUUGAGAGUAGUGUAAGAAAUUACACUACAAGUUCAAAUAAAAAUUUAUUCAAAUCCAUUUGCUACAUUGUGUAGAAUUUUUUU (SEQ ID NO: 34) | 85 |
| V2.3 | GUUUGAGAGUAGUGGAAACACUACAAGUUCAAAUAAAAAUUUAUUCAAAUCCAUUUGCUACAUUGUGUAGAAUUUUUUU (SEQ ID NO: 35) | 79 |
| V2.4 | GUUUGAGAGUAGUGGAAACACUACAAGUUCAAAUAAAAAUUUAUUCAAAUCCAUUUGCUACAUUGUGUAGAAUUUAAAGAUGCAAAUCUUUUUUU (SEQ ID NO: 36) | 95 |
| V2.5 | GUUUGAGAGUAGUGUAAGAAAUUACACUACAAGUUCAAAUAAAAAUUUAUUCAAAUCCAUUUGCUACAUUGUGUAGAAUUUAAAGAUGCAAAUCUUUUUUU (SEQ ID NO: 113) | 101 |

| Experimental Name | crRNA Repeat | tracrRNA anti-repeat |
|---|---|---|
| V2.1 | GUUUGAGAGUAGUG (SEQ ID NO: 114) | CACUACAAGUUCAAAU (SEQ ID NO: 116) |
| V2.2 | GUUUGAGAGUAGUGUAA (SEQ ID NO: 115) | UUACACUACAAGUUCAAAU (SEQ ID NO: 117) |
| V2.3 | GUUUGAGAGUAGUG (SEQ ID NO: 114) | CACUACAAGUUCAAAU (SEQ ID NO: 116) |
| V2.4 | GUUUGAGAGUAGUG (SEQ ID NO: 114) | CACUACAAGUUCAAAU (SEQ ID NO: 116) |
| V2.5 | GUUUGAGAGUAGUGUAA (SEQ ID NO: 115) | UUACACUACAAGUUCAAAU (SEQ ID NO: 117) |

| Experimental Name | tracrRNA Portion 1 | tracrRNA Portion 1 - partial | tracrRNA Portion 2 | tracrRNA Portion 2 - partial |
|---|---|---|---|---|
| V2.1 | AAAAAUUUAUUCAAAUCCAUUUGCUACAUUGUGUAGAAUUU (SEQ ID NO: 118) | Not listed | AAAGAUCUGGCAACAGAUCUUUUUUU (SEQ ID NO: 121) | AAAGAUCUGGCAACAGA (SEQ ID NO: 123) |
| V2.2 | AAAAAUUUAUUCAAAUCCAUUUGCUACAUUGUGUAGAAUUUUUUU (SEQ ID NO: 119) | AAAAAUUUAUUCAAAUCCAUUUGCUACAUUGUGUAGAA (SEQ ID NO: 120) | Not listed | Not listed |
| V2.3 | AAAAAUUUAUUCAAAUCCAUUUGCUACAUUGUGUAGAAUUUUUUU (SEQ ID NO: 119) | AAAAAUUUAUUCAAAUCCAUUUGCUACAUUGUGUAGAA (SEQ ID NO: 120) | Not listed | Not listed |
| V2.4 | AAAAAUUUAUUCAAAUCCAUUUGCUACAUUGUGUAGAAUUU (SEQ ID NO: 118) | Not listed | AAAGAUGCAAAUCUUUUUUU (SEQ ID NO: 122) | AAAGAUGCAAAUC (SEQ ID NO: 124) |

TABLE 9-continued

| OMNI-103 Designed Scaffold Sequences | | | | |
|---|---|---|---|---|
| V2.5 | AAAAAUUUAUUCAAAUCCAUUUGCUACAUUGUGUAGAAUUU (SEQ ID NO: 118) | Not listed | AAAGAUGCAAAUCUUUUUUU (SEQ ID NO: 122) | AAAGAUGCAAAUC (SEQ ID NO: 124) |

TABLE 10

| Endogenic targets for testing activity short-scaffold guide activity | | |
|---|---|---|
| Gene | Site | Spacer |
| TRAC | s91 | GCUGUGGCCUGGAGCAACAAAU (SEQ ID NO: 125) |
| PDCD1 | s40 | AACACAUCGGAGAGCUUCGUGC (SEQ ID NO: 126) |
| B2M | S12 | GUAUGCCUGCCGUGUGAACCAU (SEQ ID NO: 127) |
| TRAC | S35 | GACCCUGCCGUGUACCAGCUGA (SEQ ID NO: 128) |

TABLE 11

| Summary of the activity panel of short guides across different endogenic targets in three cell types | | | | | | | | |
|---|---|---|---|---|---|---|---|---|
| Cell Type | Gene | Site | V2 | V2.1 | V2.2 | V2.3 | V2.4 | V2.5 |
| HeLa | TRAC | s91 | 46.90 | 35.81 | 42.68 | 42.74 | 38.62 | 4.06 |
| HeLa | PDCD1 | s40 | 35.21 | 9.45 | 32.94 | 40.82 | 27.60 | 25.59 |
| U2OS | TRAC | S35 | 96.58 | N/A | 96.22 | 97.34 | N/A | N/A |
| U2OS | B2M | S12 | 97.19 | N/A | 97.76 | 96.16 | N/A | N/A |
| Primary T cells | TRAC | S35 | 77.40 | N/A | 87.60 | 90.80 | N/A | N/A |
| Primary T cells | B2M | S12 | 79.90 | N/A | 88.00 | 91.60 | N/A | N/A |

TABLE 12

| Summary of the sgRNAs used in the U2OS and primary T cell assays | | | | | |
|---|---|---|---|---|---|
| sgRNA Name | Gene | Site | Spacer | Scaffold | sgRNA |
| OMNI-103 v2.2 TRAC S35 | TRAC | S35 | SEQ ID NO: 128 | SEQ ID NO: 110 | SEQ ID NO: 129 |
| OMNI-103 v2.3 TRAC S35 | TRAC | S35 | SEQ ID NO: 128 | SEQ ID NO: 111 | SEQ ID NO: 130 |
| OMNI-103 v2.2 B2M S12 | B2M | S12 | SEQ ID NO: 127 | SEQ ID NO: 110 | SEQ ID NO: 131 |
| OMNI-103 v2.3 B2M S12 | B2M | S12 | SEQ ID NO: 127 | SEQ ID NO: 111 | SEQ ID NO: 132 |

REFERENCES

1. Ahmad and Allen (1992) "Antibody-mediated Specific Binging and Cytotoxicity of Liposome-entrapped Doxorubicin to Lung Cancer Cells in Vitro", Cancer Research 52:4817-20.
2. Anderson (1992) "Human gene therapy", Science 256: 808-13.
3. Basha et al. (2011) "Influence of Cationic Lipid Composition on Gene Silencing Properties of Lipid Nanoparticle Formulations of siRNA in Antigen-Presenting Cells", Mol. Ther. 19(12):2186-200.
4. Behr (1994) "Gene transfer with synthetic cationic amphiphiles: Prospects for gene therapy", Bioconjugate Chem 5:382-89.
5. Blaese et al. (1995) "Vectors in cancer therapy: how will they deliver", Cancer Gene Ther. 2:291-97.
6. Blaese et al. (1995) "T lymphocyte-directed gene therapy for ADA-SCID: initial trial results after 4 years", Science 270(5235):475-80.
7. Briner et al. (2014) "Guide RNA functional modules direct Cas9 activity and orthogonality", Molecular Cell 56:333-39.
8. Buchschacher and Panganiban (1992) "Human immunodeficiency virus vectors for inducible expression of foreign genes", J. Virol. 66:2731-39.
9. Burstein et al. (2017) "New CRISPR-Cas systems from uncultivated microbes", Nature 542:237-41.
10. Canver et al., (2015) "BCL11A enhancer dissection by Cas9-mediated in situ saturating mutagenesis", Nature Vol. 527, Pgs. 192-214.
11. Chang and Wilson (1987) "Modification of DNA ends can decrease end-joining relative to homologous recombination in mammalian cells", Proc. Natl. Acad. Sci. USA 84:4959-4963.
12. Charlesworth et al. (2019) "Identification of preexisting adaptive immunity to Cas9 proteins in humans", Nature Medicine, 25(2), 249.
13. Chung et al. (2006) "*Agrobacterium* is not alone: gene transfer to plants by viruses and other bacteria", Trends Plant Sci. 11(1):1-4.
14. Coelho et al. (2013) "Safety and efficacy of RNAi therapy for transthyretin amyloidosis" N. Engl. J. Med. 369, 819-829.
15. Crystal (1995) "Transfer of genes to humans: early lessons and obstacles to success", Science 270(5235): 404-10.
16. Dillon (1993) "Regulation gene expression in gene therapy" Trends in Biotechnology 11(5):167-173.
17. Dranoff et al. (1997) "A phase I study of vaccination with autologous, irradiated melanoma cells engineered to secrete human granulocyte macrophage colony stimulating factor", Hum. Gene Ther. 8(1):111-23.

18. Dunbar et al. (1995) "Retrovirally marked CD34-enriched peripheral blood and bone marrow cells contribute to long-term engraftment after autologous transplantation", Blood 85:3048-57.
19. Ellem et al. (1997) "A case report: immune responses and clinical course of the first human use of granulocyte/macrophage-colony-stimulating-factor-transduced autologous melanoma cells for immunotherapy", Cancer Immunol Immunother 44:10-20.
20. Gao and Huang (1995) "Cationic liposome-mediated gene transfer" Gene Ther. 2(10):710-22.
21. Haddada et al. (1995) "Gene Therapy Using Adenovirus Vectors", in: The Molecular Repertoire of Adenoviruses III: Biology and Pathogenesis, ed. Doerfler and Bohm, pp. 297-306.
22. Han et al. (1995) "Ligand-directed retro-viral targeting of human breast cancer cells", Proc. Natl. Acad. Sci. USA 92(21):9747-51.
23. Humbert et al., (2019) "Therapeutically relevant engraftment of a CRISPR-Cas9—edited HSC-enriched population with HbF reactivation in nonhuman primates", Sci. Trans. Med., Vol. 11, Pgs. 1-13.
24. Inaba et al. (1992) "Generation of large numbers of dendritic cells from mouse bone marrow cultures supplemented with granulocyte/macrophage colony-stimulating factor", J Exp Med. 176(6):1693-702.
25. Jiang and Doudna (2017) "CRISPR-Cas9 Structures and Mechanisms", Annual Review of Biophysics 46:505-29.
26. Jinek et al. (2012) "A programmable dual-RNA-guided DNA endonuclease in adaptive bacterial immunity", Science 337(6096):816-21.
27. Johan et al. (1992) "GLVR1, a receptor for gibbon ape leukemia virus, is homologous to a phosphate permease of *Neurospora crassa* and is expressed at high levels in the brain and thymus", J Virol 66(3):1635-40.
28. Judge et al. (2006) "Design of noninflammatory synthetic siRNA mediating potent gene silencing in vivo", Mol Ther. 13(3):494-505.
29. Kohn et al. (1995) "Engraftment of gene-modified umbilical cord blood cells in neonates with adenosine deaminase deficiency", Nature Medicine 1:1017-23.
30. Kremer and Perricaudet (1995) "Adenovirus and adeno-associated virus mediated gene transfer", Br. Med. Bull. 51(1):31-44.
31. Macdiarmid et al. (2009) "Sequential treatment of drug-resistant tumors with targeted minicells containing siRNA or a cytotoxic drug", Nat Biotechnol. 27(7):643-51.
32. Malech et al. (1997) "Prolonged production of NADPH oxidase-corrected granulocytes after gene therapy of chronic granulomatous disease", PNAS 94(22):12133-38.
33. Maxwell et al. (2018) "A detailed cell-free transcription-translation-based assay to decipher CRISPR protospacer adjacent motifs", Methods 14348-57
34. Miller et al. (1991) "Construction and properties of retrovirus packaging cells based on gibbon ape leukemia virus", J Virol. 65(5):2220-24.
35. Miller (1992) "Human gene therapy comes of age", Nature 357:455-60.
36. Mir et al. (2019) "Type II-C CRISPR-Cas9 Biology, Mechanism and Application", ACS Chem. Biol. 13(2):357-365.
37. Mitani and Caskey (1993) "Delivering therapeutic genes—matching approach and application", Trends in Biotechnology 11(5):162-66.
38. Nabel and Felgner (1993) "Direct gene transfer for immunotherapy and immunization", Trends in Biotechnology 11(5):211-15.
39. Nehls et al. (1996) "Two genetically separable steps in the differentiation of thymic epithelium" Science 272: 886-889.
40. Nishimasu et al. "Crystal structure of Cas9 in complex with guide RNA and target DNA" (2014) Cell 156(5): 935-49.
41. Nishimasu et al. (2015) "Crystal Structure of *Staphylococcus aureus* Cas9" Cell 162(5):1113-26.
42. Palermo et al. (2018) "Key role of the REC lobe during CRISPR-Cas9 activation by 'sensing', 'regulating', and 'locking' the catalytic HNH domain" Quarterly Reviews of Biophysics 51, e9, 1-11.
43. Remy et al. (1994) "Gene Transfer with a Series of Lipophilic DNA-Binding Molecules", Bioconjugate Chem. 5(6):647-54.
44. Sentmanat et al. (2018) "A Survey of Validation Strategies for CRISPR-Cas9 Editing", Scientific Reports 8:888, doi:10.1038/s41598-018-19441-8.
45. Sommerfelt et al. (1990) "Localization of the receptor gene for type D simian retroviruses on human chromosome 19", J. Virol. 64(12):6214-20.
46. Van Brunt (1988) "Molecular framing: transgenic animals as bioactors" Biotechnology 6:1149-54.
47. Vigne et al. (1995) "Third-generation adenovectors for gene therapy", Restorative Neurology and Neuroscience 8(1,2): 35-36.
48. Wagner et al. (2019) "High prevalence of *Streptococcus pyogenes* Cas9-reactive T cells within the adult human population" Nature Medicine, 25(2), 242
49. Wilson et al. (1989) "Formation of infectious hybrid virion with gibbon ape leukemia virus and human T-cell leukemia virus retroviral envelope glycoproteins and the gag and pol proteins of Moloney murine leukemia virus", J. Virol. 63:2374-78.
50. Yu et al. (1994) "Progress towards gene therapy for HIV infection", Gene Ther. 1(1):13-26.
51. Zetsche et al. (2015) "Cpf1 is a single RNA-guided endonuclease of a class 2 CRIPSR-Cas system" Cell 163(3):759-71.
52. Zuris et al. (2015) "Cationic lipid-mediated delivery of proteins enables efficient protein based genome editing in vitro and in vivo" Nat Biotechnol. 33(1):73-80.

What is claimed is:

1. A non-naturally occurring composition comprising a CRISPR nuclease comprising a sequence having at least 90% identity to the amino acid sequence of SEQ ID NO: 1, or a nucleic acid molecule comprising a sequence encoding the CRISPR nuclease, wherein the CRISPR nuclease further comprises one or more nuclear localization sequences (NLSs).

2. The composition of claim 1, further comprising one or more RNA molecules, or a DNA polynucleotide encoding any one of the one or more RNA molecules, wherein the one or more RNA molecules and the CRISPR nuclease do not naturally occur together and the one or more RNA molecules are configured to form a complex with the CRISPR nuclease and/or target the complex to a target site, and wherein the one or more RNA molecules are a) a CRISPR RNA (crRNA) molecule and a transactivating CRISPR RNA (tracrRNA) molecule, or b) a single-guide RNA (sgRNA) molecule.

3. The composition of claim 2, wherein the CRISPR nuclease comprises a sequence having at least 90% identity to the amino acid sequence set forth in SEQ ID NO: 1 and at least one RNA molecule comprises a sequence selected from the group consisting of SEQ ID NOs: 4-36.

4. The composition of claim 3, wherein the CRISPR nuclease comprises a sequence having at least 90% identity to the amino acid sequence set forth in SEQ ID NO: 1 and i) at least one RNA molecule is a CRISPR RNA (crRNA) molecule comprising a guide sequence portion and a sequence selected from the group consisting of SEQ ID NOs: 4-7 and 18-21; and further comprising a transactivating CRISPR RNA (tracrRNA) molecule comprising a sequence set forth in the group consisting of SEQ ID NOs: 8-14, 17, 22-28, and 32; or ii) at least one RNA molecule is a single-guide RNA (sgRNA) molecule comprising a guide sequence portion and a sequence selected from the group consisting of SEQ ID NOs: 4-36.

5. The composition of claim 2, wherein the CRISPR nuclease comprises a sequence having at least 90% identity to the amino acid sequence set forth in SEQ ID NO: 1 and at least one RNA molecule is a single-guide RNA (sgRNA) molecule comprising a guide sequence portion and a scaffold portion that is at least 79 nucleotides in length.

6. The composition of claim 1, wherein the CRISPR nuclease is a nickase created by an amino acid substitution at position D12, E776, H988 or D991;

wherein the CRISPR nuclease is a nickase created by an amino acid substitution at position D856, H857 or N880, wherein an amino acid substitution at position D856 is a substitution other than aspartic acid (D) to glutamic acid (E); or wherein the CRISPR nuclease is a catalytically dead nuclease created by an amino acid substitution at any one of positions D12, E776, H988 or D991 and an amino acid substitution at any one of positions D856, H857 or N880, wherein an amino acid substitution at position D856 is a substitution other than aspartic acid (D) to glutamic acid (E).

7. The composition of claim 2, wherein the one or more RNA molecules are formed by in vitro transcription (IVT) or solid-phase artificial oligonucleotide synthesis.

8. The composition of claim 2, further comprising a donor template molecule.

9. The composition of claim 8, wherein the donor template molecule is a DNA molecule.

10. The composition of claim 1, wherein the CRISPR nuclease is linked to a further protein.

11. The composition of claim 2, wherein the crRNA molecule or sgRNA molecule comprises a guide sequence portion that is 17-30 nucleotides in length.

12. The composition of claim 11, wherein the crRNA molecule or sgRNA molecule comprises a guide sequence portion that is 19-23 nucleotides in length.

13. The composition of claim 12, wherein the crRNA molecule or sgRNA molecule comprises a guide sequence portion that is 22 nucleotides in length.

14. The composition of claim 1, wherein the CRISPR nuclease comprises a sequence having at least 95% identity to the amino acid sequence set forth in SEQ ID NO: 1.

15. The composition of claim 1, wherein the CRISPR nuclease is a nickase or a catalytically inactive nuclease.

16. The composition of claim 1, wherein the nucleic acid molecule comprising a sequence encoding the CRISPR nuclease is an mRNA molecule.

17. The composition of claim 2, wherein the crRNA molecule or sgRNA molecule comprises a guide sequence portion that is complementary to a DNA strand of a DNA double-stranded region that neighbors a NNRRHY, NNRACT, or NNRVCT Protospacer Adjacent Motif (PAM) sequence.

18. The composition of claim 2, wherein the composition is a non-naturally occurring composition comprising a CRISPR associated system comprising:

one or more RNA molecules, or one or more nucleotide sequences encoding the one or more RNA molecules, wherein at least one of the one or more RNA molecules comprises a guide sequence portion linked to a direct repeat sequence, wherein the guide sequence portion is capable of hybridizing with a target sequence; and a CRISPR nuclease comprising an amino acid sequence having at least 90% identity to the amino acid sequence of SEQ ID NO: 1, or a nucleic acid molecule comprising a sequence encoding the CRISPR nuclease; and wherein the one or more RNA molecules hybridize to the target sequence, wherein the target sequence is adjacent to a complimentary sequence of a NNRRHY, NNRACT, or NNRVCT Protospacer Adjacent Motif (PAM), and the one or more RNA molecules form a complex with the RNA-guided nuclease, and the one or more RNA molecules form a complex with the CRISPR nuclease.

19. A method of modifying a nucleotide sequence at a target site in a cell-free system or the genome of a cell comprising introducing into the cell the composition of claim 2.

20. The method of claim 19, wherein the cell is a mammalian cell.

21. The method of claim 19, wherein the CRISPR nuclease effects a DNA break in a DNA strand adjacent to a NNRRHY, NNRACT, or NNRVCT PAM sequence and effects a DNA break in a DNA strand adjacent to a sequence that is complementary to the PAM sequence, or wherein the CRISPR nuclease is a nickase formed by an amino acid substitution at D12, E776, H988, or D991 of SEQ ID NO: 1 and effects a DNA break in a DNA strand adjacent to the PAM sequence, or wherein the CRISPR nuclease is a nickase formed by an amino acid substitution at D856, H857 or N880 of SEQ ID NO: 1 and effects a DNA break in a DNA strand adjacent to a sequence that is complementary to the PAM sequence, wherein an amino acid substitution at position D856 is a substitution other than aspartic acid (D) to glutamic acid (E).

22. The method of claim 19, wherein the CRISPR nuclease and one or more RNA molecules are introduced to the cell as a ribonucleoprotein (RNP) complex.

23. The method of claim 19, wherein the nucleic acid molecule comprising a sequence encoding the CRISPR nuclease is an mRNA molecule.

24. The composition of claim 1, wherein the CRISPR nuclease is fused to a DNA-interacting protein, a DNA-modifying protein, a deaminase, or a reverse transcriptase.

* * * * *

SEQUENCE LISTING

```
<160> NUMBER OF SEQ ID NOS: 135

<210> SEQ ID NO 1
<211> LENGTH: 1348
<212> TYPE: PRT
<213> ORGANISM: Unknown
<220> FEATURE:
<223> OTHER INFORMATION: OMNI-103
```

```
<400> SEQUENCE: 1

Met Ser Ile Lys Ser Asp Tyr Phe Leu Gly Leu Asp Ile Gly Thr Asp
1               5                   10                  15

Ser Ile Gly Trp Ala Val Thr Asp Pro Glu Tyr His Ile Leu Arg Arg
            20                  25                  30

Lys Gly Lys Ala Leu Trp Gly Ile Arg Leu Phe Asp Ala Ala Asn Thr
        35                  40                  45

Ala Ala Glu Arg Arg Thr Phe Arg Thr Ser Arg Arg Arg Ile Gln Arg
    50                  55                  60

Arg Arg Gln Arg Ile Arg Leu Leu Gln Glu Leu Phe Ala Glu Glu Met
65                  70                  75                  80

Val Lys Leu Asp Pro Gly Phe Phe Gln Arg Leu Ser Asp Ser Ala Phe
                85                  90                  95

Trp Gln Glu Asp Lys Gln Glu Gln Ile Tyr Ser Leu Phe Thr Cys
            100                 105                 110

Glu Asn Tyr Thr Asp Val Asp Tyr Tyr Arg Glu Tyr Pro Thr Ile Tyr
        115                 120                 125

His Leu Arg Ser Ala Leu Ile Gln Glu Lys Lys Glu Phe Asp Leu Arg
    130                 135                 140

Leu Leu Tyr Leu Ala Leu His His Leu Met Lys His Arg Gly His Phe
145                 150                 155                 160

Leu Phe Asn Gly Ser Ile Asn Asn Val Thr Ser Phe His Thr Thr Phe
                165                 170                 175

Gln Thr Phe Ala Asp Cys Leu Tyr Asp Glu Phe Asp Ile Glu Leu Glu
            180                 185                 190

Cys Asp Ser Glu Asp Arg Phe Ala Glu Ile Leu Lys Asp Lys His Ala
        195                 200                 205

Arg Lys Thr Gly Lys Cys Ser Glu Leu Glu Ile Ile Cys His Ile Glu
    210                 215                 220

Lys Ser Asn Lys Gln Leu Lys Glu Leu Phe Lys Leu Ile Thr Gly Met
225                 230                 235                 240

Lys Ala Ser Leu Ser Val Val Phe Gly Asp Asp Glu Leu Ala Glu Ile
                245                 250                 255

Glu His Asn Lys Ile Ser Phe Ser Glu Ser Ser Tyr Asp Glu Val Arg
            260                 265                 270

Leu Ala Leu Glu Asp Glu Ile Gln Glu Arg Thr Gly Ile Leu Asp Ile
        275                 280                 285

Phe His Ala Val Tyr Ser Trp Ala Ile Leu Ala Asp Ile Leu Glu Gly
    290                 295                 300

Gly Glu Tyr Glu Gly Asn Ser Tyr Leu Ser Val Ala Lys Val Ser Thr
305                 310                 315                 320

Tyr Lys Lys His Gly Asp Asp Leu Arg Leu Leu Arg Thr Leu Val Arg
                325                 330                 335

Glu Tyr Cys Pro Asp His Tyr Lys Ser Phe Phe Ser Val Ser Gly Lys
            340                 345                 350

Glu Asn Tyr Cys Ala Tyr Ala Gly Thr Leu Lys Lys Asn Gly Lys Lys
        355                 360                 365

Gln Pro Ile Lys Arg Cys Ser Gln Glu Asp Phe Tyr Lys Ala Leu Lys
    370                 375                 380

Lys Leu Leu Asn Gln Met Pro Thr Glu Gln Pro Glu Val Lys Asp Ile
385                 390                 395                 400

Phe Ile Glu Ile Glu Asn Gly Thr Phe Leu Pro Leu Gln Val Ser Lys
                405                 410                 415
```

-continued

```
Asp Asn Gly Val Ile Pro Tyr Gln Val Asn Lys Met Glu Leu Glu Lys
            420                 425                 430

Ile Leu Gln Asn Ala Glu Glu Tyr Leu Pro Phe Leu Lys Asn Ile Asp
        435                 440                 445

Glu Glu Cys Gly Lys Thr Val Ser Lys Lys Ile Ile Asp Leu Phe Glu
    450                 455                 460

Phe Arg Ile Pro Tyr Tyr Val Gly Pro Leu Asn Thr Ala Lys Gly Glu
465                 470                 475                 480

Asn Cys Trp Met Val Arg Lys Glu Ala Gly Arg Ile Tyr Pro Trp Asn
                485                 490                 495

Phe Asp Glu Lys Val Asp Arg Asp Gln Ser Ala Glu Lys Phe Ile Arg
            500                 505                 510

Arg Met Thr Asn Gln Cys Thr Tyr Leu Ile His Glu Asp Val Val Pro
        515                 520                 525

Lys Asn Ser Leu Leu Tyr Ser Glu Phe Met Val Leu Asn Glu Leu Asn
    530                 535                 540

Asn Val Lys Ile Arg Ser Glu Lys Leu Pro Val Glu Leu Lys Gln Ala
545                 550                 555                 560

Ile Val Leu Asp Leu Phe Lys Lys Gln Lys Gln Ile Thr Gly Lys Lys
                565                 570                 575

Leu Leu Asn Tyr Leu Asn Ala Asn Gly Tyr Asp Val Lys Lys Glu Asp
            580                 585                 590

Leu Ser Gly Phe Asp Gly Asn Phe Lys Ser Ser Leu Ser Ser Tyr Leu
        595                 600                 605

Thr Leu Lys Lys Val Phe Gly Glu Glu Leu Asp Lys Tyr Ser Val Gln
    610                 615                 620

Gln Met Ala Glu Asp Ile Ile Leu Trp Ile Thr Leu Tyr Gly Asp Asp
625                 630                 635                 640

Gln Lys Met Leu Arg Arg Val Ile Arg Lys His Tyr Glu Gln Gln Leu
                645                 650                 655

Ser Glu Glu Gln Ile Leu Ser Leu Ser Lys Leu Lys Phe Gln Gly Trp
            660                 665                 670

Gly Arg Leu Ser Arg Arg Leu Leu Ser Glu Met Glu Gly Val Asp Cys
        675                 680                 685

Glu Thr Gly Glu Cys Met Thr Val Met Gln Gly Leu Arg Asn Thr Gln
    690                 695                 700

Asn Asn Leu Met Gln Leu Leu Ser Gln Gln Phe Ser Phe Met Glu Leu
705                 710                 715                 720

Ile Glu Glu Glu Asn Gly Asn Tyr Tyr Val Asp Glu Ile Thr Tyr Asp
                725                 730                 735

Asn Leu Val Lys Asp Met Val Ile Ser Pro Ser Val Lys Arg Ala Val
            740                 745                 750

Trp Gln Thr Val Gln Ile Val Glu Glu Ile Lys Gly Val Met Gly Cys
        755                 760                 765

Gln Pro Lys Lys Ile Phe Val Glu Met Ala Arg Ser Asp Glu Glu Lys
    770                 775                 780

Lys Arg Thr Val Ser Arg Lys Asp Arg Leu Leu Glu Ala Tyr Asp Ala
785                 790                 795                 800

Ile Lys Asp Glu Ala Arg Gln Trp Gln Glu Glu Leu Gln Lys Tyr Ser
                805                 810                 815

Asp Gly Asp Phe Lys Ala Ile Lys Leu Tyr Leu Tyr Tyr Thr Gln Met
            820                 825                 830
```

```
Gly Gln Cys Met Tyr Thr Gly Arg Lys Ile Asp Leu Ser Gln Leu Asn
        835                 840                 845

Asp Ala Thr Val Trp Asp Arg Asp His Ile Tyr Pro Gln Ser Lys Thr
    850                 855                 860

Lys Asp Asp Ser Leu Asp Asn Leu Val Leu Val Asp Arg Ser Val Asn
865                 870                 875                 880

Ala Lys Lys Ser Asp Gly Met Leu Ser Pro Glu Ile Gln Gln Arg Met
                885                 890                 895

Arg Ala Thr Trp Lys Tyr Leu Lys Glu Lys Lys Leu Ile Ser Glu Lys
            900                 905                 910

Lys Tyr Glu Arg Leu Thr Arg Val Ser Pro Leu Thr Asp Glu Glu Leu
        915                 920                 925

Ala Gly Phe Ile Asn Arg Gln Leu Val Glu Thr Arg Gln Ser Ser Lys
    930                 935                 940

Ala Val Ala Thr Leu Leu Lys Arg Val Tyr Asp Glu Ala Glu Ile Val
945                 950                 955                 960

Tyr Val Lys Ala Glu Ala Val Ser Asn Phe Arg Arg Asp Asn Leu Asp
                965                 970                 975

Tyr Ile Lys Val Arg Asp Leu Asn Asp Tyr His His Ala Lys Asp Ala
            980                 985                 990

Tyr Gln Asn Ile Val Val Gly Asn  Val Phe His Glu Lys  Phe Thr Ser
        995                 1000                 1005

Asn Pro  Leu Arg Trp Leu Lys  Asn Asn Pro Asn Thr  Lys Tyr Ser
    1010                 1015                 1020

Leu Asn  Gln Met Phe Asn Phe  Asp Leu Glu Lys Asn  Gly Val Val
    1025                 1030                 1035

Ile Trp  Lys Arg Gly Lys Ala  Gly Ser Ile Lys Cys  Val Glu Glu
    1040                 1045                 1050

Thr Leu  Lys Arg Asn Asp Ile  Leu Phe Thr Arg Tyr  Ala Phe Cys
    1055                 1060                 1065

Asn Lys  Gly Gly Phe Phe Asn  Gln Met Leu Thr Ala  Ala Pro Glu
    1070                 1075                 1080

Asp Lys  Thr Lys Ala Lys Gly  Leu Val Pro Ile Lys  Lys Gly Met
    1085                 1090                 1095

Glu Thr  Trp Lys Tyr Gly Gly  Tyr Thr Ser Val Thr  Pro Ser His
    1100                 1105                 1110

Phe Met  Leu Val Ala Ser Lys  Asp Lys Lys Gly Lys  Glu Ile Arg
    1115                 1120                 1125

Thr Ile  Glu Thr Val Pro Leu  Tyr Arg Trp Lys Glu  Phe Lys Glu
    1130                 1135                 1140

Asn Pro  Asp Ala Leu Leu Gln  Tyr Cys Arg Glu Phe  Tyr Gly Leu
    1145                 1150                 1155

Lys Glu  Pro Lys Val Leu Ile  Pro Cys Ile Lys Lys  Asn Ala Arg
    1160                 1165                 1170

Leu Val  Val Asn Gly Phe Pro  Met His Leu Lys Gly  Ser Thr Gly
    1175                 1180                 1185

Lys Gln  Leu Ile Leu Gln Gly  Ala Val Gln Leu Cys  Leu Asn Asn
    1190                 1195                 1200

Glu Asn  Ile Lys Tyr Leu Lys  Lys Val Thr Lys Tyr  Leu Glu Tyr
    1205                 1210                 1215

Asn Ala  Gln Arg Arg Asp Lys  Arg Thr Leu Leu Glu  Val Arg Glu
    1220                 1225                 1230

Val Thr  Gly Ile Asn Lys Glu  Glu Asn Ile Gln Leu  Tyr Asp Val
```

```
    1235                1240                1245

Phe Val  Asp Lys Leu Ser Asn  Thr Ile Tyr Gln Tyr  Arg Pro Ala
    1250                1255                1260

Asn Pro  Lys Asp Asn Leu Ile  Lys Gly Arg Glu Lys  Phe Ile Glu
    1265                1270                1275

Leu Gly  Leu Ala Glu Gln Cys  Val Val Leu Gly Glu  Val Leu His
    1280                1285                1290

Leu Phe  Gln Cys Lys Pro Leu  Thr Ser Asp Leu Thr  Leu Ile Gly
    1295                1300                1305

Gly Ser  Pro Asn Thr Gly Thr  Ile Lys Ile Thr Lys  Thr Ile Ser
    1310                1315                1320

Asn Cys  Asn Val Val Lys Leu  Leu Ser Gln Ser Ile  Ala Gly Val
    1325                1330                1335

Lys Val  Arg Glu Ile Asn Leu  Leu Ile Ile
    1340                1345
```

<210> SEQ ID NO 2
<211> LENGTH: 4047
<212> TYPE: DNA
<213> ORGANISM: Unknown
<220> FEATURE:
<223> OTHER INFORMATION: OMNI-103

<400> SEQUENCE: 2

```
atgagcataa aaagtgatta ttttttagga cttgatattg gtacggattc tattggatgg     60

gcggtaaccg acccagaata tcacatattg agacgaaaag gtaaagcatt atggggaata    120

agattatttg atgcggccaa tacagcggca gaacggcgaa catttaggac aagccgaaga    180

aggattcaga gaagacgaca gagaattcgg ttattgcaag aattatttgc agaagaaatg    240

gtaaaattag acccaggatt ttttcagagg ttgtcagaca gcgcattttg gcaggaggat    300

aagcaagagc agcaaattta ttcacttttt acttgtgaaa attatacaga tgttgattat    360

tacagagaat atcctactat ttatcatttg agaagtgcat tgattcagga aaagaaggaa    420

tttgatcttc gtcttctata tcttgctctt caccatttga tgaagcacag ggacatttc     480

ctgtttaatg ggagtattaa taatgtgacg tcatttcata cgacgtttca gacgtttgca    540

gattgtcttt atgatgagtt tgatatagaa ctggaatgtg attccgaaga tagatttgca    600

gaaattttaa aggataaaca tgccagaaaa acaggaaaat gttctgaatt agagataatc    660

tgtcatatag aaaaatcaaa taagcagcta aaagaacttt ttaaattaat tacaggaatg    720

aaagctagtt tgagtgttgt gtttggtgat gatgagttag cggaaataga acataataag    780

attagttttt cagagagtag ttatgatgaa gtacgtcttg cattggagga tgagattcag    840

gagaggactg gtatactgga tatctttcat gcagtttata gttgggcgat tctcgcggat    900

attttagaag gcggagaata tgaggggaat tcttatctaa gcgttgcgaa ggtaagcact    960

tataaaaagc atggtgatga tttgcggttg ctaagaacac tggttcggga atattgtcct   1020

gatcattaca aatctttctt ttccgtatca gggaaggaga attattgtgc atatgcgggt   1080

actttaaaaa agaatggaaa aaaacagccg attaaacgtt gcagccagga agatttttat   1140

aaagcgttaa agaaattgct gaatcagatg ccgacagaac aaccagaagt gaaagacatc   1200

ttcatcgaaa ttgaaaatgg tacttttttg ccgttgcagg taagtaagga taatggagtg   1260

ataccttatc aggtaaataa gatggaatta gaaaaaatcc tgcagaatgc agaggaatat   1320

ttgccatttc taaaaaatat agatgaagaa tgtggaaaaa cggttagtaa gaagattata   1380
```

```
gatctctttg agtttagaat accatattat gtagggccgc ttaataccgc taaaggagaa   1440
aactgttgga tggtcagaaa agaagcgggg agaatatatc cgtggaattt tgatgaaaag   1500
gtagacagag atcaatcagc agaaaaattt atccgtagaa tgacgaatca gtgtacatat   1560
ttaatacatg aggatgttgt acctaaaaat tctttgcttt attcggagtt tatggtgctt   1620
aatgaattaa ataatgtaaa gatccggtct gagaagctgc cggtggagtt aaaacaggca   1680
atagtattgg atttgtttaa gaaacaaaag cagataacag gaaaaaaact tcttaattac   1740
ttgaatgcaa atggatatga tgtaaaaaaa gaagatttgt cagggtttga cggaaacttt   1800
aaatcatctc tgtcatcata tcttactttg aaaaaagtat ttggtgaaga attagataaa   1860
tatagtgtgc agcagatggc agaggatatt atcttgtgga tcactctgta tggagatgat   1920
cagaagatgt tgcgcagggt aattcgaaaa cattatgaac agcaattgag tgaagaacag   1980
attctttcct tatcgaaatt gaaattccaa ggctggggaa gattatccag acgacttttg   2040
agtgaaatgg aaggcgttga ttgtgagact ggtgagtgta tgacggtcat gcaaggactt   2100
cgtaatactc agaataatct gatgcagctt ctaagtcagc agttttcatt tatggaattg   2160
attgaggaag aaaatgggaa ttattatgta gatgagatta catacgataa tcttgtgaaa   2220
gatatggtta tatctccgtc agtgaagaga gcagtctggc agacagttca gattgtggag   2280
gagattaagg gggtaatggg ctgtcagcct aagaagatat ttgtcgagat ggcgcgaagc   2340
gatgaagaga aaaagcgtac tgtatctagg aaagacaggt tattagaagc atatgatgcg   2400
atcaaggatg aggctcgtca atggcaggaa gagttgcaaa agtattcaga tggtgatttt   2460
aaggctatta aactttatct gtattatacg cagatggggc aatgtatgta tactggaaga   2520
aagatagatc tgtcacaatt aaatgatgcg acggtatggg acagagatca tatatatcca   2580
cagtccaaaa caaaagatga tagtctggat aatctggtat tggtagaccg gagcgtgaac   2640
gctaagaaaa gtgatgggat gctatcacct gagattcagc agagaatgcg ggctacttgg   2700
aaatacttaa aagagaaaaa gttgatttca gagaagaaat atgagcgttt gactagggtc   2760
tcaccactta cagatgagga attggcaggt tttattaatc gacagttagt tgaaacacgt   2820
cagtcttcga aagcagtagc aacacttttg aaacgagtat atgatgaagc ggagattgtc   2880
tatgtaaaag cggaagctgt ttcaaatttt agaagagata atttggatta tattaaggtg   2940
cgtgatctga atgattatca tcatgctaaa gatgcatatc agaatattgt agtggggaat   3000
gtttttcatg agaaatttac cagcaatccg cttcgttggc tgaaaaacaa tcctaatacg   3060
aaatatagtt taaatcagat gtttaacttt gatttagaga aaaatggggt ggtaatatgg   3120
aaaaggggga aggctggaag tattaaatgt gttgaagaaa cattgaaaag aaatgatatt   3180
ctttttacac gatatgcttt ttgtaataaa ggtggttttt ttaaccagat gttaacggca   3240
gctccagaag ataaaacgaa agcaaaggga cttgtaccaa taaaaaaagg tatggaaaca   3300
tggaaatacg gggatatac atcagtaact ccgtcacatt ttatgttggt tgcttcgaaa   3360
gataagaaag gaaaggagat aagaacgatt gagacagttc cgttgtatag gtggaaagag   3420
ttcaaagaaa atccagatgc attactccaa tattgtagag agttctatgg tttgaaagag   3480
cccaaggtgt tgataccatg catcaagaag aatgccagat tagtcgttaa tggatttcca   3540
atgcatttga aagggagtac aggaaaacaa ttgattttgc agggagcggt tcaattatgt   3600
ctgaataatg aaaatataaa gtatttgaaa aaagtcacaa aatatttgga atataatgca   3660
cagagaagag ataaaagaac actgctggaa gtaagagagg ttacaggaat taacaaagag   3720
gaaaatatac agttatatga tgtgtttgtt gataaattga gtaacacaat atatcagtat   3780
```

```
cgtccggcca atccaaagga caatcttata aaaggaagag agaagtttat agaattaggg   3840

ttggcagaac aatgtgttgt gttaggtgaa gtattgcatt tgttccaatg taaaccactc   3900

acgtctgatt tgactttgat tggaggttca ccgaatacag ggacaataaa aataacaaag   3960

acaattagta attgtaatgt tgtaaagttg ttaagccaat ctattgcagg tgttaaagtg   4020

agagaaatta atttgttaat aatatga                                       4047
```

<210> SEQ ID NO 3
<211> LENGTH: 4047
<212> TYPE: DNA
<213> ORGANISM: Artificial Sequence
<220> FEATURE:
<223> OTHER INFORMATION: OMNI-103 human optimized DNA sequence

<400> SEQUENCE: 3

```
atgtctatca agagcgacta cttcctgggc ctcgacatcg gcacagattc tatcggatgg     60

gccgtgacag accccgagta ccacatcctg agaagaaagg gcaaagccct gtggggcatc    120

agactgttcg atgccgccaa tactgccgcc gagagaagaa ccttccggac cagcagaaga    180

agaatccagc ggcggagaca gcggatcaga ctgctgcaag agctgttcgc cgaggaaatg    240

gttaagctgg accccggctt cttccagaga ctgagcgata gcgccttctg gcaagaggac    300

aagcaagagc agcagatcta cagcctgttt acctgcgaga actacaccga cgtggactac    360

tacagagagt accccaccat ctaccacctg agaagcgccc tgatccaaga gaaaaaagag    420

ttcgacctgc ggctgctgta tctggccctg caccatctga tgaagcaccg gggccacttt    480

ctgttcaacg gcagcatcaa caacgtgacc agcttccaca ccaccttcca gaccttcgcc    540

gactgcctgt acgacgagtt cgacatcgag ctggaatgcg acagcgagga cagattcgcc    600

gagatcctga aggataagca cgccagaaag accggcaagt gctctgagct ggaaatcatc    660

tgccacatcg agaagtccaa caagcagctg aaagaactgt tcaagctgat caccggcatg    720

aaggccagcc tgagcgtggt gtttggagat gatgagctgg ccgagatcga gcacaacaag    780

atcagcttca gcgagagcag ctacgacgaa gtgcggctgg ccctggaaga tgagattcaa    840

gagagaaccg gcatcctgga catcttccac gccgtgtatt cttgggccat cctggccgat    900

attctggaag gcggcgagta cgagggcaac agctatctgt ctgtggccaa ggtgtccacc    960

tacaagaagc acggcgacga cctgagactg ctgagaacac tcgtgcgcga gtactgcccc   1020

gaccactaca agagcttttt cagcgtgtcc ggcaaagaga actactgcgc ctacgccggc   1080

acactgaaga agaacggcaa gaagcagccc atcaagcggt gcagccaaga ggacttctac   1140

aaggccctga agaaactgct gaaccagatg cctaccgagc agcccgaagt gaaggatatc   1200

ttcatcgaga ttgagaacgg caccttcctg cctctgcaag tgtccaagga caacggcgtg   1260

atcccctacc aagtgaacaa gatggaactc gagaagatcc tgcagaacgc cgaagagtac   1320

ctgcctttcc tgaagaacat cgacgaggaa tgcggcaaga ccgtgtccaa gaagatcatc   1380

gacctgttcg agttcagaat cccctactac gtgggccctc tgaataccgc caagggcgag   1440

aattgctgga tggttcgaaa agaggccggc agaatctacc cctggaactt cgatgagaag   1500

gtggacagag atcagagcgc cgagaagttc atcagacgga tgaccaacca gtgcacctac   1560

ctgatccacg aggacgtggt gcctaagaac agcctgctgt actccgagtt catggtgctg   1620

aacgagctga acaatgtgaa gattcggagc gagaagctgc ccgtggaact gaagcaggcc   1680

atcgtgctgg acctgtttaa gaagcagaag cagatcacag ggaagaagct gctcaactac   1740
```

-continued

```
ctgaacgcca acggctacga cgtgaagaaa gaggacctga gcggcttcga cggcaacttc   1800
aagtccagcc tgtccagcta cctgactctg aagaaggtgt tcggagagga actggacaag   1860
tacagcgtgc agcagatggc cgaggacatc atcctgtgga tcaccctgta tggcgacgat   1920
cagaaaatgc tgcggagagt gatccggaag cactacgagc agcagctgtc tgaggaacag   1980
atcctgagcc tgagcaagct gaagttccaa ggctggggca gactgtctag acggctgctc   2040
tctgaaatgg aaggcgtgga ctgtgaaacc ggcgagtgca tgacagtgat gcagggcctg   2100
agaaacaccc agaacaacct gatgcagctg ctgagccagc agttcagctt catggaactg   2160
atcgaggaag agaacgggaa ctactacgtc gacgagatca cctacgacaa cctggtcaag   2220
gacatggtca tcagccctag cgtgaaaagg gccgtgtggc agacagtgca gatcgtggaa   2280
gaaatcaagg gcgtgatggg atgccagcct aagaaaatct tcgtggaaat ggcccgcagc   2340
gacgaagaga agaaacggac cgtgtctcgg aaggatcggc tgctggaagc ctacgacgcc   2400
atcaaggatg aggcccggca atggcaagaa gaactgcaga aatactccga cggcgatttc   2460
aaggccatca agctgtacct gtactacacc cagatgggcc agtgcatgta caccggcaga   2520
aaaatcgatc tgtcccagct gaacgacgcc accgtgtggg atagagatca catctaccct   2580
cagagcaaga ccaaggacga cagcctggac aatctggtgc tggtggatag atccgtgaat   2640
gccaagaaaa gcgacggcat gctgagcccc gagatccagc agagaatgag agccacctgg   2700
aagtacctga aagaaaagaa gctcatcagc gagaagaagt acgagcggct gaccagagtg   2760
tcccctctga cagatgaaga actggccggc ttcatcaacc ggcagctggt ggaaacaaga   2820
cagagcagca aagccgtggc cacactgctg aagagggtgt acgatgaggc cgagattgtg   2880
tatgtgaagg ccgaggccgt gtctaacttc cggcgggata acctggacta catcaaagtg   2940
cgggacctga acgactacca ccacgccaag gacgcctacc agaacatcgt cgtgggcaac   3000
gtgttccacg agaagtttac cagcaatccc ctgcggtggc tgaaaaacaa ccccaacacc   3060
aagtactccc tcaaccagat gttcaacttc gacctggaaa agaacggcgt ggtcatctgg   3120
aagagaggca aggccggctc cattaagtgt gtggaagaga cactgaagcg gaacgacatc   3180
ctgttcacca gatacgcttt ctgcaacaaa ggcggcttct ttaatcagat gctgaccgcc   3240
gctccagagg ataagacaaa ggccaaaggc ctggtgccta tcaagaaagg catggaaacc   3300
tggaaatacg gcggctacac cagcgtgacc cctagccact ttatgctggt ggccagcaag   3360
gacaagaagg gaaaagagat ccggaccatc gagacagtgc ccctgtaccg gtggaaagag   3420
ttcaaagaga atcccgacgc tctgctccag tactgcagag agttctacgg cctgaaagag   3480
cccaaggttc tgatcccttg catcaagaag aatgcccggc tggtcgtgaa cggcttccct   3540
atgcacctga agggcagcac cggaaaacag ctgattctgc agggtgccgt gcagctgtgc   3600
ctgaacaacg agaacatcaa gtacctcaag aaagtgacga agtacctcga gtacaacgcc   3660
cagcggagag acaagagaac cctgctcgaa gttcgggaag tgaccggaat caacaaagag   3720
gaaaacatcc agctgtacga tgtgttcgtg gacaagctga gcaacacaat ctaccagtac   3780
agacccgcca atcctaagga caacctcatc aagggccgcg agaaattcat cgagcttggc   3840
ctggctgagc agtgcgtggt gctgggagaa gtgctgcatc tgttccagtg caagcccctg   3900
accagcgatc tgacactgat cggcggaagc cctaacaccg gcaccatcaa gatcaccaag   3960
accatcagca actgcaacgt ggtcaagctg ctgtcccagt ctatcgccgg cgtgaaagtc   4020
cgcgagatca acctgctgat catctga                                       4047
```

<210> SEQ ID NO 4
<211> LENGTH: 17
<212> TYPE: RNA
<213> ORGANISM: Artificial Sequence
<220> FEATURE:
<223> OTHER INFORMATION: sgRNA 12 crRNA repeat

<400> SEQUENCE: 4
guuugagagu aguguaa 17

<210> SEQ ID NO 5
<211> LENGTH: 15
<212> TYPE: RNA
<213> ORGANISM: Artificial Sequence
<220> FEATURE:
<223> OTHER INFORMATION: sgRNA 12 Partial crRNA 1

<400> SEQUENCE: 5
guuugagagu agugu 15

<210> SEQ ID NO 6
<211> LENGTH: 12
<212> TYPE: RNA
<213> ORGANISM: Artificial Sequence
<220> FEATURE:
<223> OTHER INFORMATION: sgRNA 12 Partial crRNA 2

<400> SEQUENCE: 6
guuugagagu ag 12

<210> SEQ ID NO 7
<211> LENGTH: 10
<212> TYPE: RNA
<213> ORGANISM: Artificial Sequence
<220> FEATURE:
<223> OTHER INFORMATION: sgRNA 12 Partial crRNA 3

<400> SEQUENCE: 7
guuugagagu 10

<210> SEQ ID NO 8
<211> LENGTH: 19
<212> TYPE: RNA
<213> ORGANISM: Artificial Sequence
<220> FEATURE:
<223> OTHER INFORMATION: sgRNA 12 tracrRNA antirepeat

<400> SEQUENCE: 8
uuacacuaca aguucaaau 19

<210> SEQ ID NO 9
<211> LENGTH: 17
<212> TYPE: RNA
<213> ORGANISM: Artificial Sequence
<220> FEATURE:
<223> OTHER INFORMATION: sgRNA 12 partial tracrRNA 1

<400> SEQUENCE: 9
acacuacaag uucaaau 17

<210> SEQ ID NO 10
<211> LENGTH: 14
<212> TYPE: RNA
<213> ORGANISM: Artificial Sequence
<220> FEATURE:
<223> OTHER INFORMATION: sgRNA 12 partial tracrRNA 2

<400> SEQUENCE: 10
cuacaaguuc aaau 14

<210> SEQ ID NO 11
<211> LENGTH: 12
<212> TYPE: RNA
<213> ORGANISM: Artificial Sequence
<220> FEATURE:
<223> OTHER INFORMATION: sgRNA 12 partial tracrRNA 3

<400> SEQUENCE: 11
acaaguucaa au 12

<210> SEQ ID NO 12
<211> LENGTH: 41
<212> TYPE: RNA
<213> ORGANISM: Artificial Sequence
<220> FEATURE:
<223> OTHER INFORMATION: sgRNA 12 tracrRNA portion 1

<400> SEQUENCE: 12
aaaaauuuau ucaaauccuu uugcuacauu guguagaauu u 41

<210> SEQ ID NO 13
<211> LENGTH: 26
<212> TYPE: RNA
<213> ORGANISM: Artificial Sequence
<220> FEATURE:
<223> OTHER INFORMATION: sgRNA 12 tracrRNA portion 2

<400> SEQUENCE: 13
aaagaucugg caacagaucu uuuuuu 26

<210> SEQ ID NO 14
<211> LENGTH: 19
<212> TYPE: RNA
<213> ORGANISM: Artificial Sequence
<220> FEATURE:
<223> OTHER INFORMATION: sgRNA 12 tracrRNA portion 2 polyT

<400> SEQUENCE: 14
aaagaucugg caacagauc 19

<210> SEQ ID NO 15
<211> LENGTH: 107
<212> TYPE: RNA
<213> ORGANISM: Artificial Sequence
<220> FEATURE:
<223> OTHER INFORMATION: sgRNA 12 V1

<400> SEQUENCE: 15
guuugagagu aguguaagaa auuacacuac aaguucaaau aaaaauuuau ucaaauccuu 60
uugcuacauu guguagaauu uaaagaucug gcaacagauc uuuuuuu 107

<210> SEQ ID NO 16
<211> LENGTH: 107
<212> TYPE: RNA
<213> ORGANISM: Artificial Sequence
<220> FEATURE:
<223> OTHER INFORMATION: sgRNA 12 V2

<400> SEQUENCE: 16
guuugagagu aguguaagaa auuacacuac aaguucaaau aaaaauuuau ucaaauccau 60
uugcuacauu guguagaauu uaaagaucug gcaacagauc uuuuuuu 107

<210> SEQ ID NO 17
<211> LENGTH: 41
<212> TYPE: RNA
<213> ORGANISM: Artificial Sequence
<220> FEATURE:
<223> OTHER INFORMATION: sgRNA 12 V2 Modified tracrRNA

<400> SEQUENCE: 17
aaaaauuuau ucaaauccau uugcuacauu guguagaauu u 41

<210> SEQ ID NO 18
<211> LENGTH: 17
<212> TYPE: RNA
<213> ORGANISM: Artificial Sequence
<220> FEATURE:
<223> OTHER INFORMATION: sgRNA 32 crRNA repeat

<400> SEQUENCE: 18
guuugagagu aguguaa 17

<210> SEQ ID NO 19
<211> LENGTH: 15
<212> TYPE: RNA
<213> ORGANISM: Artificial Sequence
<220> FEATURE:
<223> OTHER INFORMATION: sgRNA 32 Partial crRNA 1

<400> SEQUENCE: 19
guuugagagu agugu 15

<210> SEQ ID NO 20
<211> LENGTH: 12
<212> TYPE: RNA
<213> ORGANISM: Artificial Sequence
<220> FEATURE:
<223> OTHER INFORMATION: sgRNA 32 Partial crRNA 2

<400> SEQUENCE: 20
guuugagagu ag 12

<210> SEQ ID NO 21
<211> LENGTH: 10
<212> TYPE: RNA
<213> ORGANISM: Artificial Sequence
<220> FEATURE:
<223> OTHER INFORMATION: sgRNA 32 Partial crRNA 3

<400> SEQUENCE: 21
guuugagagu 10

<210> SEQ ID NO 22
<211> LENGTH: 19
<212> TYPE: RNA
<213> ORGANISM: Artificial Sequence
<220> FEATURE:
<223> OTHER INFORMATION: sgRNA 32 tracrRNA antirepeat

<400> SEQUENCE: 22
uuacacuaca aguucaaau 19

<210> SEQ ID NO 23
<211> LENGTH: 17
<212> TYPE: RNA
<213> ORGANISM: Artificial Sequence
<220> FEATURE:

<223> OTHER INFORMATION: sgRNA 32 Partial tracrRNA 1

<400> SEQUENCE: 23
acacuacaag uucaaau 17

<210> SEQ ID NO 24
<211> LENGTH: 14
<212> TYPE: RNA
<213> ORGANISM: Artificial Sequence
<220> FEATURE:
<223> OTHER INFORMATION: sgRNA 32 Partial tracrRNA 2

<400> SEQUENCE: 24
cuacaaguuc aaau 14

<210> SEQ ID NO 25
<211> LENGTH: 12
<212> TYPE: RNA
<213> ORGANISM: Artificial Sequence
<220> FEATURE:
<223> OTHER INFORMATION: sgRNA 32 Partial tracrRNA 3

<400> SEQUENCE: 25
acaaguucaa au 12

<210> SEQ ID NO 26
<211> LENGTH: 41
<212> TYPE: RNA
<213> ORGANISM: Artificial Sequence
<220> FEATURE:
<223> OTHER INFORMATION: sgRNA 32 tracrRNA portion 1

<400> SEQUENCE: 26
aaaaauuuau ucaaauccuu uugcuacauu guguagaauu u 41

<210> SEQ ID NO 27
<211> LENGTH: 32
<212> TYPE: RNA
<213> ORGANISM: Artificial Sequence
<220> FEATURE:
<223> OTHER INFORMATION: sgRNA 32 tracrRNA portion 2

<400> SEQUENCE: 27
aaagaucugg caacagaucu uuuuuauuuu uu 32

<210> SEQ ID NO 28
<211> LENGTH: 26
<212> TYPE: RNA
<213> ORGANISM: Artificial Sequence
<220> FEATURE:
<223> OTHER INFORMATION: sgRNA 32 tracrRNA portion 2 polyT

<400> SEQUENCE: 28
aaagaucugg caacagaucu uuuuua 26

<210> SEQ ID NO 29
<211> LENGTH: 113
<212> TYPE: RNA
<213> ORGANISM: Artificial Sequence
<220> FEATURE:
<223> OTHER INFORMATION: sgRNA 32 V1

<400> SEQUENCE: 29
guuugagagu aguguaagaa auuacacuac aaguucaaau aaaaauuuau ucaaauccuu 60
uugcuacauu guguagaauu uaaagaucug gcaacagauc uuuuuuauuu uuu 113

<210> SEQ ID NO 30
<211> LENGTH: 106
<212> TYPE: RNA
<213> ORGANISM: Artificial Sequence
<220> FEATURE:
<223> OTHER INFORMATION: sgRNA 32 V2

<400> SEQUENCE: 30
guuugagagu aguguaagaa auuacacuac aaguucaaau aaaaauuuau ucaaauccuu 60
uugcuacauu guguagaauu uaaagaucug gcaacagauc uuuuuu 106

<210> SEQ ID NO 31
<211> LENGTH: 106
<212> TYPE: RNA
<213> ORGANISM: Artificial Sequence
<220> FEATURE:
<223> OTHER INFORMATION: sgRNA 32 V3

<400> SEQUENCE: 31
guuugagagu aguguaagaa auuacacuac aaguucaaau aaaaauuuau ucaaauccau 60
uugcuacauu guguagaauu uaaagaucug gcaacagauc uuuuuu 106

<210> SEQ ID NO 32
<211> LENGTH: 41
<212> TYPE: RNA
<213> ORGANISM: Artificial Sequence
<220> FEATURE:
<223> OTHER INFORMATION: sgRNA 32 V3 modified tracrRNA

<400> SEQUENCE: 32
aaaaauuuau ucaaauccau uugcuacauu guguagaauu u 41

<210> SEQ ID NO 33
<211> LENGTH: 101
<212> TYPE: RNA
<213> ORGANISM: Artificial Sequence
<220> FEATURE:
<223> OTHER INFORMATION: V2.1

<400> SEQUENCE: 33
guuugagagu aguggaaaca cuacaaguuc aaauaaaaau uuauucaaau ccauuugcua 60
cauuguguag aauuuaaaga ucuggcaaca gaucuuuuuu u 101

<210> SEQ ID NO 34
<211> LENGTH: 85
<212> TYPE: RNA
<213> ORGANISM: Artificial Sequence
<220> FEATURE:
<223> OTHER INFORMATION: V2.2

<400> SEQUENCE: 34
guuugagagu aguguaagaa auuacacuac aaguucaaau aaaaauuuau ucaaauccau 60
uugcuacauu guguagaauu uuuuu 85

<210> SEQ ID NO 35
<211> LENGTH: 79
<212> TYPE: RNA
<213> ORGANISM: Artificial Sequence
<220> FEATURE:
<223> OTHER INFORMATION: V2.3

<400> SEQUENCE: 35
guuugagagu aguggaaaca cuacaaguuc aaauaaaaau uuauucaaau ccauuugcua 60
cauuguguag aauuuuuuu 79

<210> SEQ ID NO 36
<211> LENGTH: 95
<212> TYPE: RNA
<213> ORGANISM: Artificial Sequence
<220> FEATURE:
<223> OTHER INFORMATION: V2.4

<400> SEQUENCE: 36
guuugagagu aguggaaaca cuacaaguuc aaauaaaaau uuauucaaau ccauuugcua 60
cauuguguag aauuuaaaga ugcaaaucuu uuuuu 95

<210> SEQ ID NO 37
<211> LENGTH: 6373
<212> TYPE: DNA
<213> ORGANISM: Artificial Sequence
<220> FEATURE:
<223> OTHER INFORMATION: pET9a OMNI-103

<400> SEQUENCE: 37
taatacgact cactataggg agaccacaac ggtttccctc tagagagaca ataaccctga 60
taatgcttca ataatattga aaaaggaaga gtatgcctaa gaagaagaga aaggtgggta 120
cctctatcaa gagcgactac ttcctgggcc tcgacatcgg cacagattct atcggatggg 180
ccgtgacaga ccccgagtac cacatcctga gaagaaaggg caaagccctg tggggcatca 240
gactgttcga tgccgccaat actgccgccg agagaagaac cttccggacc agcagaagaa 300
gaatccagcg gcggagacag cggatcagac tgctgcaaga gctgttcgcc gaggaaatgg 360
ttaagctgga ccccggcttc ttccagagac tgagcgatag cgccttctgg caagaggaca 420
agcaagagca gcagatctac agcctgttta cctgcgagaa ctacaccgac gtggactact 480
acagagagta ccccaccatc taccacctga gaagcgccct gatccaagag aaaaaagagt 540
tcgacctgcg gctgctgtat ctggccctgc accatctgat gaagcaccgg ggccactttc 600
tgttcaacgg cagcatcaac aacgtgacca gcttccacac caccttccag accttcgccg 660
actgcctgta cgacgagttc gacatcgagc tggaatgcga cagcgaggac agattcgccg 720
agatcctgaa ggataagcac gccagaaaga ccggcaagtg ctctgagctg gaaatcatct 780
gccacatcga gaagtccaac aagcagctga aagaactgtt caagctgatc accggcatga 840
aggccagcct gagcgtggtg tttggagatg atgagctggc cgagatcgag cacaacaaga 900
tcagcttcag cgagagcagc tacgacgaag tgcggctggc cctggaagat gagattcaag 960
agagaaccgg catcctggac atcttccacg ccgtgtattc ttgggccatc ctggccgata 1020
ttctggaagg cggcgagtac gagggcaaca gctatctgtc tgtggccaag gtgtccacct 1080
acaagaagca cggcgacgac ctgagactgc tgagaacact cgtgcgcgag tactgccccg 1140
accactacaa gagctttttc agcgtgtccg gcaaagagaa ctactgcgcc tacgccggca 1200
cactgaagaa gaacggcaag aagcagccca tcaagcggtg cagccaagag gacttctaca 1260
aggccctgaa gaaactgctg aaccagatgc ctaccgagca gcccgaagtg aaggatatct 1320
tcatcgagat tgagaacggc accttcctgc ctctgcaagt gtccaaggac aacggcgtga 1380
tcccctacca agtgaacaag atggaactcg agaagatcct gcagaacgcc gaagagtacc 1440
tgcctttcct gaagaacatc gacgaggaat gcggcaagac cgtgtccaag aagatcatcg 1500
acctgttcga gttcagaatc ccctactacg tgggccctct gaataccgcc aagggcgaga 1560

```
attgctggat ggttcgaaaa gaggccggca gaatctaccc ctggaacttc gatgagaagg   1620
tggacagaga tcagagcgcc gagaagttca tcagacggat gaccaaccag tgcacctacc   1680
tgatccacga ggacgtggtg cctaagaaca gcctgctgta ctccgagttc atggtgctga   1740
acgagctgaa caatgtgaag attcggagcg agaagctgcc cgtggaactg aagcaggcca   1800
tcgtgctgga cctgtttaag aagcagaagc agatcacagg gaagaagctg ctcaactacc   1860
tgaacgccaa cggctacgac gtgaagaaag aggacctgag cggcttcgac ggcaacttca   1920
agtccagcct gtccagctac ctgactctga agaaggtgtt cggagaggaa ctggacaagt   1980
acagcgtgca gcagatggcc gaggacatca tcctgtggat caccctgtat ggcgacgatc   2040
agaaaatgct gcggagagtg atccggaagc actacgagca gcagctgtct gaggaacaga   2100
tcctgagcct gagcaagctg aagttccaag gctggggcag actgtctaga cggctgctct   2160
ctgaaatgga aggcgtggac tgtgaaaccg gcgagtgcat gacagtgatg cagggcctga   2220
gaaacaccca gaacaacctg atgcagctgc tgagccagca gttcagcttc atggaactga   2280
tcgaggaaga gaacgggaac tactacgtcg acgagatcac ctacgacaac ctggtcaagg   2340
acatggtcat cagccctagc gtgaaaaggg ccgtgtggca gacagtgcag atcgtggaag   2400
aaatcaaggg cgtgatggga tgccagccta agaaaatctt cgtggaaatg gcccgcagcg   2460
acgaagagaa gaaacggacc gtgtctcgga aggatcggct gctggaagcc tacgacgcca   2520
tcaaggatga ggcccggcaa tggcaagaag aactgcagaa atactccgac ggcgatttca   2580
aggccatcaa gctgtacctg tactacaccc agatgggcca gtgcatgtac accggcagaa   2640
aaatcgatct gtcccagctg aacgacgcca ccgtgtggga tagagatcac atctaccctc   2700
agagcaagac caaggacgac agcctggaca atctggtgct ggtggataga tccgtgaatg   2760
ccaagaaaag cgacggcatg ctgagccccg agatccagca gagaatgaga gccacctgga   2820
agtacctgaa agaaaagaag ctcatcagcg agaagaagta cgagcggctg accagagtgt   2880
cccctctgac agatgaagaa ctggccggct tcatcaaccg gcagctggtg gaaacaagac   2940
agagcagcaa agccgtggcc acactgctga agagggtgta cgatgaggcc gagattgtgt   3000
atgtgaaggc cgaggccgtg tctaacttcc ggcgggataa cctggactac atcaaagtgc   3060
gggacctgaa cgactaccac cacgccaagg acgcctacca gaacatcgtc gtgggcaacg   3120
tgttccacga gaagtttacc agcaatcccc tgcggtggct gaaaaacaac cccaacacca   3180
agtactccct caaccagatg ttcaacttcg acctggaaaa gaacggcgtg gtcatctgga   3240
agagaggcaa ggccggctcc attaagtgtg tggaagagac actgaagcgg aacgacatcc   3300
tgttcaccag atacgctttc tgcaacaaag gcggcttctt taatcagatg ctgaccgccg   3360
ctccagagga taagacaaag gccaaaggcc tggtgcctat caagaaaggc atggaaacct   3420
ggaaatacgg cggctacacc agcgtgaccc ctagccactt tatgctggtg gccagcaagg   3480
acaagaaggg aaaagagatc cggaccatcg agacagtgcc cctgtaccgg tggaaagagt   3540
tcaaagagaa tcccgacgct ctgctccagt actgcagaga gttctacggc ctgaaagagc   3600
ccaaggttct gatcccttgc atcaagaaga atgcccggct ggtcgtgaac ggcttcccta   3660
tgcacctgaa gggcagcacc ggaaaacagc tgattctgca gggtgccgtg cagctgtgcc   3720
tgaacaacga gaacatcaag tacctcaaga aagtgacgaa gtacctcgag tacaacgccc   3780
agcggagaga caagagaacc ctgctcgaag ttcgggaagt gaccggaatc aacaaagagg   3840
aaaacatcca gctgtacgat gtgttcgtgg acaagctgag caacacaatc taccagtaca   3900
```

-continued

```
gacccgccaa tcctaaggac aacctcatca agggccgcga gaaattcatc gagcttggcc   3960
tggctgagca gtgcgtggtg ctgggagaag tgctgcatct gttccagtgc aagcccctga   4020
ccagcgatct gacactgatc ggcggaagcc ctaacaccgg caccatcaag atcaccaaga   4080
ccatcagcaa ctgcaacgtg gtcaagctgc tgtcccagtc tatcgccggc gtgaaagtcc   4140
gcgagatcaa cctgctgatc atcggatcct acccatacga tgttccagat tacgcggccg   4200
ctccaaaaaa gaaaagaaaa gttgcggcta gccatcatca ccatcaccat catcattaag   4260
gctgctaaca aagcccgaaa ggaagctgag ttggctgctg ccaccgctga gcaataacta   4320
gcataacccc ttggggcctc taaacgggtc ttgaggggtt ttttgctgaa aggaggaact   4380
atatccggat atccacagga cgggtgtggt cgccatgatc gcgtagtcga tagtggctcc   4440
aagtagcgaa gcgagcagga ctgggcggcg gccaaagcgg tcggacagtg ctccgagaac   4500
gggtgcgcat agaaattgca tcaacgcata tagcgctagc agcacgccat agtgactggc   4560
gatgctgtcg gaatggacga tatcccgcaa gaggcccggc agtaccggca taaccaagcc   4620
tatgcctaca gcatccaggg tgacggtgcc gaggatgacg atgagcgcat tgttagattt   4680
catacacggt gcctgactgc gttagcaatt taactgtgat aaactaccgc attaaagctt   4740
atcgatgata agctgtcaaa catgagaatt cttagaaaaa ctcatcgagc atcaaatgaa   4800
actgcaattt attcatatca ggattatcaa taccatattt ttgaaaaagc cgtttctgta   4860
atgaaggaga aaactcaccg aggcagttcc ataggatggc aagatcctgg tatcggtctg   4920
cgattccgac tcgtccaaca tcaatacaac ctattaattt cccctcgtca aaaataaggt   4980
tatcaagtga gaaatcacca tgagtgacga ctgaatccgg tgagaatggc aaaagcttat   5040
gcatttcttt ccagacttgt tcaacaggcc agccattacg ctcgtcatca aaatcactcg   5100
catcaaccaa accgttattc attcgtgatt gcgcctgagc gagacgaaat acgcgatcgc   5160
tgttaaaagg acaattacaa acaggaatcg aatgcaaccg gcgcaggaac actgccagcg   5220
catcaacaat attttcacct gaatcaggat attcttctaa tacctggaat gctgttttcc   5280
cggggatcgc agtggtgagt aaccatgcat catcaggagt acggataaaa tgcttgatgg   5340
tcggaagagg cataaattcc gtcagccagt ttagtctgac catctcatct gtaacatcat   5400
tggcaacgct acctttgcca tgtttcagaa acaactctgg cgcatcgggc ttcccataca   5460
atcgatagat tgtcgcacct gattgcccga cattatcgcg agcccattta tacccatata   5520
aatcagcatc catgttggaa tttaatcgcg gcctcgagca agacgtttcc cgttgaatat   5580
ggctcataac accccttgta ttactgttta tgtaagcaga cagttttatt gttcatgacc   5640
aaaatccctt aacgtgagtt ttcgttccac tgagcgtcag accccgtaga aaagatcaaa   5700
ggatcttctt gagatccttt ttttctgcgc gtaatctgct gcttgcaaac aaaaaaacca   5760
ccgctaccag cggtggtttg tttgccggat caagagctac caactctttt tccgaaggta   5820
actggcttca gcagagcgca gataccaaat actgtccttc tagtgtagcc gtagttaggc   5880
caccacttca agaactctgt agcaccgcct acatacctcg ctctgctaat cctgttacca   5940
gtggctgctg ccagtggcga taagtcgtgt cttaccgggt tggactcaag acgatagtta   6000
ccggataagg cgcagcggtc gggctgaacg gggggttcgt gcacacagcc cagcttggag   6060
cgaacgacct acaccgaact gagataccta cagcgtgagc tatgagaaag cgccacgctt   6120
cccgaaggga gaaaggcgga caggtatccg gtaagcggca gggtcggaac aggagagcgc   6180
acgagggagc ttccaggggg aaacgcctgg tatctttata gtcctgtcgg gtttcgccac   6240
ctctgacttg agcgtcgatt tttgtgatgc tcgtcagggg ggcggagcct atggaaaaac   6300
```

gccagcaacg cggccttttt acggttcctg gccttttgct ggccttttgc tcacatgttc 6360
gatcccgcga aat 6373

<210> SEQ ID NO 38
<211> LENGTH: 2783
<212> TYPE: DNA
<213> ORGANISM: Artificial Sequence
<220> FEATURE:
<223> OTHER INFORMATION: pShuttle Guide OMNI-103 V2

<400> SEQUENCE: 38
tacacggtgc ctgactgcgt tagcaattta actgtgataa actaccgcat taaagcttat 60
cgatgataag ctgtcaacac atttccccga aaagtgccac ctgacgtcct cgagtcccgc 120
ataatcgaaa tgagggccta tttcccatga ttccttcata tttgcatata cgatacaagg 180
ctgttagaga gataattaga attaatttga ctgtaaacac aaagatatta gtacaaaata 240
cgtgacgtag aaagtaataa tttcttgggt agtttgcagt tttaaaatta tgttttaaaa 300
tggactatca tatgcttacc gtaacttgaa agtatttcga tttcttggct ttatatatct 360
tgctaatacg actcactata ggaagagcag agccttggtc tcgtttgaga gtagtgtaag 420
aaattacact acaagttcaa ataaaaattt attcaaatcc atttgctaca ttgtgtagaa 480
tttaaagatc tggcaacaga tctttttttg aattctctag cataacccct tggggcctct 540
aaacgggtct tgaggggttt tttgacctag gctaggggat atattccggg taccccgctt 600
cctcgctcac tgactcgcta cgctcggtcg ttcgactgcg gcgagcggaa atggcttacg 660
aacggggcgg agatttcctg gaagatgcca ggaagatact taacagggaa gtgagagggc 720
cgcggcaaag ccgtttttcc ataggctccg cccccctgac aagcatcacg aaatctgacg 780
ctcaaatcag tggtggcgaa acccgacagg actataaaga taccaggcgt ttccccctgg 840
cggctccctc gtgcgctctc ctgttcctgc ctttcggttt accggtgtca ttccgctgtt 900
atggccgcgt ttgtctcatt ccacgcctga cactcagttc cgggtaggca gttcgctcca 960
agctggactg tatgcacgaa ccccccgttc agtccgaccg ctgcgcctta tccggtaact 1020
atcgtcttga gtccaacccg gaaagacatg caaaagcacc actggcagca gccactggta 1080
attgatttag aggagttagt cttgaagtca tgcgccggtt aaggctaaac tgaaaggaca 1140
agttttggtg actgcgctcc tccaagccag ttacctcggt tcaaagagtt ggtagctcag 1200
agaaccttcg aaaaaccgcc ctgcaaggcg gttttttcgt tttcagagca agagattacg 1260
cgcagaccaa aacgatctca agaagatcat cttattaatc agataaaata tttctagatt 1320
tcagtgcaat ttatctcttc aaatgtagca cctgaagtca gccccatacg atataagttg 1380
ttactagtgc ttggattctc accaataaaa aacgcccggc ggcaaccgag cgttctgaac 1440
aaatccagat ggagttctga ggtcattact ggatctatca acaggagtcc aagcgagaag 1500
ggttggtttg cgcattcaca gttctccgca agaattgatt ggctccaatt cttggagtgg 1560
tgaatccgtt agcgaggtgc cgccggcttc cattcaggtc gaggtggccc ggctccatgc 1620
accgcgacgc aacgcgggga ggcagacaag gtatagggcg gcgcctacaa tccatgccaa 1680
cccgttccat gtgctcgccg aggcggcata aatcgccgtg acgatcagcg gtccaatgat 1740
cgaagttagg ctggtaagag ccgcgagcga tccttgaagc tgtccctgat ggtcgtcatc 1800
tacctgcctg gacagcatgg cctgcaacgc gggcatcccg atgccgccgg aagcgagaag 1860
aatcataatg gggaaggcca tccagcctcg cgtcgcgaac gccagcaaga cgtagcccag 1920

```
cgcgtcggcc gccatgccgg cgataatggc ctgcttctcg ccgaaacgtt tggtggcggg   1980

accagtgacg aaggcttgag cgagggcgtg caagattccg aataccgcaa gcgacaggcc   2040

gatcatcgtc gcgctccagc gaaagcggtc ctcgccgaaa atgacccaga gcgctgccgg   2100

cacctgtcct acgagttgca tgataaagaa gacagtcata agtgcggcga cgatagtcat   2160

gccccgcgcc caccggaagg agctgactgg gttgaaggct ctcaagggca tcggtcgacg   2220

ctctccctta tgcgactcct gcattaggaa gcagcccagt agtaggttga ggccgttgag   2280

caccgccgcc gcaaggaatg gtgcatgcaa ggagatggcg cccaacagtc ccccggccac   2340

ggggcctgcc accataccca cgccgaaaca agcgctcatg agcccgaagt ggcgagcccg   2400

atcttcccca tcggtgatgt cggcgatata ggcgccagca accgcacctg tggcgccggt   2460

gatgccggcc acgatgcgtc cggcgtagag gatccacagg acgggtgtgg tcgccatgat   2520

cgcgtagtcg atagtggctc caagtagcga agcgagcagg actgggcggc ggccaaagcg   2580

gtcggacagt gctccgagaa cgggtgcgca tagaaattgc atcaacgcat atagcgctag   2640

cagcacgcca tagtgactgg cgatgctgtc ggaatggacg atatcccgca agaggcccgg   2700

cagtaccggc ataaccaagc ctatgcctac agcatccagg gtgacggtgc cgaggatgac   2760

gatgagcgca ttgttagatt tca                                           2783
```

<210> SEQ ID NO 39
<211> LENGTH: 5009
<212> TYPE: DNA
<213> ORGANISM: Artificial Sequence
<220> FEATURE:
<223> OTHER INFORMATION: pbPOS T2 library
<220> FEATURE:
<221> NAME/KEY: misc_feature
<222> LOCATION: (3040)..(3047)
<223> OTHER INFORMATION: n is a, c, g, or t

<400> SEQUENCE: 39

```
tcgagtcttt acactttatg cttccggctc gtatgttgtg tggaattgtg agcggataac     60

aatttcacac atgattacgg attcaacgtc gtgactggta aaacccgggc gttacccaac    120

ttaatcgcct tgcagcacat ccccctttcg ccagcaggcg taataaggaa aggattcatg    180

tactatttga aaaacacaaa cttttggatg ttcggtttat tctttttctt ttactttttt    240

atcatgggag cctacttccc gtttttcccg atttggctac atgatatcaa ccatatcagc    300

aaaagtgata cgggtattat ttttgccgct atttctctgt tctcgctatt attccaaccg    360

ctgtttggtc tgctttctga caaactcggt ctacgcaaat acctgctgtg gattattacc    420

ggcatgttag tgatgtttgc gccgttcttt atttttatct tcgggccact gctgcagtac    480

aacattttag tagggtcgat tgttggtggt atttatctag gctttagttt taacgccggt    540

gcgccagcag tagaggcatt tattgagaaa gtcagccggc gcagtaattt cgaatttggt    600

cgcgcgcgga tgtttggcag tgttggctgg gcgctggttg cctcgattgt cgggatcatg    660

ttcaccatta ataatcagtt tgttttctgg ctgggctctg gcagttgtct catcctcgcc    720

gttttactct tttcgccaa aacggacgcg ccctcaagtg ccacggttgc caatgcggta    780

ggtgccaacc attcggcatt tagccttaag ctggcactgg aactgttcag acagccaaaa    840

ctgtggtttt tgtcactgta tgttattggc gtttcctcca cctacgatgt ttttgaccaa    900

cagtttgcta atttctttac ttcgttcttt gctaccggtg aacagggtac ccgcgtattt    960

ggctacgtaa cgacaatggg cgaattactt aacgcctcga ttatgttctt tgcgccactg   1020

atcattaatc gcatcggtgg gaagaatgcc ctgctgctgg ctggcactat tatgtctgta   1080
```

```
cgtattattg gctcatcgtt cgccacctca gcgctggaag tggttattct gaaaacgctg   1140
catatgtttg aagtaccgtt cctgctggtg ggctccttta aatatattac tagtcagttt   1200
gaagtgcgtt tttcagcgac gatttatctg gtcagtttca gcttctttaa gcaactggcg   1260
atgattttta tgtctgtact ggcgggcaat atgtatgaaa gcataggttt ccaaggcgct   1320
tatctggtgc tgggtctggt ggcgctgggc ttcaccttaa tttccgtgtt cacgcttagc   1380
ggcccgggcc cgctttccct gctgcgtcgt caggtgaatg aagtcgctta aaggcctcga   1440
tgcagctagc atgctaatct gattcgttac caattatgac aacttgacgg ctacatcatt   1500
cactttttct tcacaaccgg cacggaactc gctcgggctg gccccggtgc atttttaaa    1560
tacccgcgag aaatagagtt gatcgtcaaa accaacattg cgaccgacgg tggcgatagg   1620
catccgggtg gtgctcaaaa gcagcttcgc ctggctgata cgttggtcct cgcgccagct   1680
taagacgcta atccctaact gctggcggaa aagatgtgac agacgcgacg gcgacaagca   1740
aacatgctgt gcgacgctgg cgatatcaaa attgctgtct gccaggtgat cgctgatgta   1800
ctgacaagcc tcgcgtaccc gattatccat cggtggatgg agcgactcgt taatcgcttc   1860
catgcgccgc agtaacaatt gctcaagcag atttatcgcc agcagctccg aatagcgccc   1920
ttccccttgc ccggcgttaa tgatttgccc aaacaggtcg ctgaaatgcg gctggtgcgc   1980
ttcatccggg cgaaagaacc ccgtattggc aaatattgac ggccagttaa gccattcatg   2040
ccagtaggcg cgcggacgaa agtaaaccca ctggtgatac cattcgcgag cctccggatg   2100
acgaccgtag tgatgaatct ctcctggcgg gaacagcaaa atatcacccg gtcggcaaac   2160
aaattctcgt ccctgatttt tcaccacccc ctgaccgcga atggtgagat tgagaatata   2220
acctttcatt cccagcggtc ggtcgataaa aaaatcgaga taaccgttgg cctcaatcgg   2280
cgttaaaccc gccaccagat gggcattaaa cgagtatccc ggcagcaggg gatcattttg   2340
cgcttcagcc atacttttca tactcccgcc attcagagaa gaaaccaatt gtccatattg   2400
catcagacat tgccgtcact gcgtctttta ctggctcttc tcgctaacca aaccggtaac   2460
cccgcttatt aaaagcattc tgtaacaaag cgggaccaaa gccatgacaa aaacgcgtaa   2520
caaaagtgtc tataatcacg gcagaaaagt ccacattgat tatttgcacg gcgtcacact   2580
ttgctatgcc atagcatttt tatccataag attagcggat cctacctgac gctttttatc   2640
gcaactctct actgtttctc catacccgtt tttttggggt agcgattgaa aacgatgcag   2700
tttaaggttt acacctataa aagagagagc cgttatcgtc tgtttgtgga tgtacagagt   2760
gatattattg acacgcccgg gcgacggatg gtgatccccc tggccagtgc acgtctgctg   2820
tcagataaag tctcccgtga actttacccg gtggtgcata tcggggatga aagctggcgc   2880
atgatgacca ccgatatggc cagtgtgccg gtctccgtta tcggggaaga agtggctgat   2940
ctcagccacc gcgaaaatga catcaaaaac gccattaacc tgatgttttg gggaatataa   3000
tcttctagac atacaatgga agagcagagc cttggtctcn nnnnnnnaag cttgatatcg   3060
aattcctgca gcccggggga tcccatggta cgcgtgctag aggcatcaaa taaaacgaaa   3120
ggctcagtcg aaagactggg cctttcgttt tatctgttgt ttgtcggtga acgctctcct   3180
gagtaggaca aatccgccgc cctagaccta ggcgttcggc tgcggcgagc ggtatcagct   3240
cactcaaagg cggtaatacg gttatccaca gaatcagggg ataacgcagg aaagaacatg   3300
tgagcaaaag gccagcaaaa ggccaggaac cgtaaaaagg ccgcgttgct ggcgtttttc   3360
cataggctcc gcccccctga cgagcatcac aaaaatcgac gctcaagtca gaggtggcga   3420
```

```
aacccgacag gactataaag ataccaggcg tttccccctg gaagctccct cgtgcgctct   3480
cctgttccga ccctgccgct taccggatac ctgtccgcct ttctcccttc gggaagcgtg   3540
gcgctttctc aatgctcacg ctgtaggtat ctcagttcgg tgtaggtcgt tcgctccaag   3600
ctgggctgtg tgcacgaacc ccccgttcag cccgaccgct gcgccttatc cggtaactat   3660
cgtcttgagt ccaacccggt aagacacgac ttatcgccac tggcagcagc cactggtaac   3720
aggattagca gagcgaggta tgtaggcggt gctacagagt tcttgaagtg gtggcctaac   3780
tacggctaca ctagaaggac agtatttggt atctgcgctc tgctgaagcc agttaccttc   3840
ggaaaaagag ttggtagctc ttgatccggc aaacaaacca ccgctggtag cggtggtttt   3900
tttgtttgca agcagcagat tacgcgcaga aaaaaaggat ctcaagaaga tcctttgatc   3960
ttttctacgg ggtctgacgc tcagtggaac gaaaactcac gttaagggat tttggtcatg   4020
actagtgctt ggattctcac caataaaaaa cgcccggcgg caaccgagcg ttctgaacaa   4080
atccagatgg agttctgagg tcattactgg atctatcaac aggagtccaa gcgagctcga   4140
tatcaaatta cgccccgccc tgccactcat cgcagtactg ttgtaattca ttaagcattc   4200
tgccgacatg gaagccatca cagacggcat gatgaacctg aatcgccagc ggcatcagca   4260
ccttgtcgcc ttgcgtataa tatttgccca tggtgaaaac gggggcgaag aagttgtcca   4320
tattggccac gtttaaatca aaactggtga aactcaccca gggattggct gagacgaaaa   4380
acatattctc aataaaccct ttagggaaat aggccaggtt ttcaccgtaa cacgccacat   4440
cttgcgaata tatgtgtaga aactgccgga aatcgtcgtg gtattcactc cagagcgatg   4500
aaaacgtttc agtttgctca tggaaaacgg tgtaacaagg gtgaacacta tcccatatca   4560
ccagctcacc gtctttcatt gccatacgga attccggatg agcattcatc aggcgggcaa   4620
gaatgtgaat aaaggccgga taaaacttgt gcttattttt ctttacggtc tttaaaaagg   4680
ccgtaatatc cagctgaacg gtctggttat aggtacattg agcaactgac tgaaatgcct   4740
caaaatgttc tttacgatgc cattgggata tatcaacggt ggtatatcca gtgatttttt   4800
tctccatttt agcttcctta gctcctgaaa atctcgataa ctcaaaaaat acgcccggta   4860
gtgatcttat ttcattatgg tgaaagttgg aacctcttac gtgccgatca acgtctcatt   4920
ttcgccagat atcgacgtct aagaaaccat tattatcatg acattaacct ataaaaatag   4980
gcgtatcacg aggccctttc gtcttcacc                                     5009
```

<210> SEQ ID NO 40
<211> LENGTH: 10286
<212> TYPE: DNA
<213> ORGANISM: Artificial Sequence
<220> FEATURE:
<223> OTHER INFORMATION: pmOMNI OMNI-103

<400> SEQUENCE: 40

```
gacggatcgg gagatctccc gatcccctat ggtgcactct cagtacaatc tgctctgatg     60
ccgcatagtt aagccagtat ctgctccctg cttgtgtgtt ggaggtcgct gagtagtgcg    120
cgagcaaaat ttaagctaca acaaggcaag gcttgaccga caattgcatg aagaatctgc    180
ttagggttag gcgttttgcg ctgcttcgcg atgtacgggc cagatatacg cgttgacatt    240
gattattgac tagttattaa tagtaatcaa ttacggggtc attagttcat agcccatata    300
tggagttccg cgttacataa cttacggtaa atggcccgcc tggctgaccg cccaacgacc    360
cccgcccatt gacgtcaata atgacgtatg ttcccatagt aacgccaata gggactttcc    420
attgacgtca atgggtggag tatttacggt aaactgccca cttggcagta catcaagtgt    480
```

```
atcatatgcc aagtacgccc cctattgacg tcaatgacgg taaatggccc gcctggcatt    540
atgcccagta catgacctta tgggactttc ctacttggca gtacatctac gtattagtca    600
tcgctattac catggtgatg cggttttggc agtacatcaa tgggcgtgga tagcggtttg    660
actcacgggg atttccaagt ctccacccca ttgacgtcaa tgggagtttg ttttggcacc    720
aaaatcaacg ggactttcca aaatgtcgta acaactccgc cccattgacg caaatgggcg    780
gtaggcgtgt acggtgggag gtctatataa gcagagctct ctggctaact agagaaccca    840
ctgcttactg gcttatcgaa attaatacga ctcactatag ggagacccaa gctggctagc    900
gtttaaactt aagcttgcca ccatgcctaa gaagaagaga aaggtgggta cctctatcaa    960
gagcgactac ttcctgggcc tcgacatcgg cacagattct atcggatggg ccgtgacaga   1020
ccccgagtac cacatcctga gaagaaaggg caaagccctg tggggcatca gactgttcga   1080
tgccgccaat actgccgccg agagaagaac cttccggacc agcagaagaa gaatccagcg   1140
gcggagacag cggatcagac tgctgcaaga gctgttcgcc gaggaaatgg ttaagctgga   1200
ccccggcttc ttccagagac tgagcgatag cgccttctgg caagaggaca agcaagagca   1260
gcagatctac agcctgttta cctgcgagaa ctacaccgac gtggactact acagagagta   1320
ccccaccatc taccacctga gaagcgccct gatccaagag aaaaaagagt tcgacctgcg   1380
gctgctgtat ctggccctgc accatctgat gaagcaccgg ggccactttc tgttcaacgg   1440
cagcatcaac aacgtgacca gcttccacac caccttccag accttcgccg actgcctgta   1500
cgacgagttc gacatcgagc tggaatgcga cagcgaggac agattcgccg agatcctgaa   1560
ggataagcac gccagaaaga ccggcaagtg ctctgagctg gaaatcatct gccacatcga   1620
gaagtccaac aagcagctga aagaactgtt caagctgatc accggcatga aggccagcct   1680
gagcgtggtg tttggagatg atgagctggc cgagatcgag cacaacaaga tcagcttcag   1740
cgagagcagc tacgacgaag tgcggctggc cctggaagat gagattcaag agagaaccgg   1800
catcctggac atcttccacg ccgtgtattc ttgggccatc ctggccgata ttctggaagg   1860
cggcgagtac gagggcaaca gctatctgtc tgtggccaag gtgtccacct acaagaagca   1920
cggcgacgac ctgagactgc tgagaacact cgtgcgcgag tactgccccg accactacaa   1980
gagctttttc agcgtgtccg gcaaagagaa ctactgcgcc tacgccggca cactgaagaa   2040
gaacggcaag aagcagccca tcaagcggtg cagccaagag gacttctaca aggccctgaa   2100
gaaactgctg aaccagatgc ctaccgagca gcccgaagtg aaggatatct tcatcgagat   2160
tgagaacggc accttcctgc ctctgcaagt gtccaaggac aacggcgtga tcccctacca   2220
agtgaacaag atggaactcg agaagatcct gcagaacgcc gaagagtacc tgcctttcct   2280
gaagaacatc gacgaggaat gcggcaagac cgtgtccaag aagatcatcg acctgttcga   2340
gttcagaatc ccctactacg tgggccctct gaataccgcc aagggcgaga attgctggat   2400
ggttcgaaaa gaggccggca gaatctaccc ctggaacttc gatgagaagg tggacagaga   2460
tcagagcgcc gagaagttca tcagacggat gaccaaccag tgcacctacc tgatccacga   2520
ggacgtggtg cctaagaaca gcctgctgta ctccgagttc atggtgctga acgagctgaa   2580
caatgtgaag attcggagcg agaagctgcc cgtggaactg aagcaggcca tcgtgctgga   2640
cctgtttaag aagcagaagc agatcacagg gaagaagctg ctcaactacc tgaacgccaa   2700
cggctacgac gtgaagaaag aggacctgag cggcttcgac ggcaacttca agtccagcct   2760
gtccagctac ctgactctga agaaggtgtt cggagaggaa ctggacaagt acagcgtgca   2820
```

-continued

```
gcagatggcc gaggacatca tcctgtggat caccctgtat ggcgacgatc agaaaatgct   2880
gcggagagtg atccggaagc actacgagca gcagctgtct gaggaacaga tcctgagcct   2940
gagcaagctg aagttccaag gctggggcag actgtctaga cggctgctct ctgaaatgga   3000
aggcgtggac tgtgaaaccg gcgagtgcat gacagtgatg cagggcctga gaaacaccca   3060
gaacaacctg atgcagctgc tgagccagca gttcagcttc atggaactga tcgaggaaga   3120
gaacgggaac tactacgtcg acgagatcac ctacgacaac ctggtcaagg acatggtcat   3180
cagccctagc gtgaaaaggg ccgtgtggca gacagtgcag atcgtggaag aaatcaaggg   3240
cgtgatggga tgccagccta agaaaatctt cgtggaaatg gcccgcagcg acgaagagaa   3300
gaaacggacc gtgtctcgga aggatcggct gctggaagcc tacgacgcca tcaaggatga   3360
ggcccggcaa tggcaagaag aactgcagaa atactccgac ggcgatttca aggccatcaa   3420
gctgtacctg tactacaccc agatgggcca gtgcatgtac accggcagaa aaatcgatct   3480
gtcccagctg aacgacgcca ccgtgtggga tagagatcac atctaccctc agagcaagac   3540
caaggacgac agcctggaca atctggtgct ggtggataga tccgtgaatg ccaagaaaag   3600
cgacggcatg ctgagccccg agatccagca gagaatgaga gccacctgga agtacctgaa   3660
agaaaagaag ctcatcagcg agaagaagta cgagcggctg accagagtgt cccctctgac   3720
agatgaagaa ctggccggct tcatcaaccg gcagctggtg gaaacaagac agagcagcaa   3780
agccgtggcc acactgctga agagggtgta cgatgaggcc gagattgtgt atgtgaaggc   3840
cgaggccgtg tctaacttcc ggcgggataa cctggactac atcaaagtgc gggacctgaa   3900
cgactaccac cacgccaagg acgcctacca gaacatcgtc gtgggcaacg tgttccacga   3960
gaagtttacc agcaatcccc tgcggtggct gaaaaacaac cccaacacca agtactccct   4020
caaccagatg ttcaacttcg acctggaaaa gaacggcgtg gtcatctgga agagaggcaa   4080
ggccggctcc attaagtgtg tggaagagac actgaagcgg aacgacatcc tgttcaccag   4140
atacgctttc tgcaacaaag gcggcttctt taatcagatg ctgaccgccg ctccagagga   4200
taagacaaag gccaaaggcc tggtgcctat caagaaaggc atggaaacct ggaaatacgg   4260
cggctacacc agcgtgaccc ctagccactt tatgctggtg gccagcaagg acaagaaggg   4320
aaaagagatc cggaccatcg agacagtgcc cctgtaccgg tggaaagagt tcaaagagaa   4380
tcccgacgct ctgctccagt actgcagaga gttctacggc ctgaaagagc ccaaggttct   4440
gatcccttgc atcaagaaga atgcccggct ggtcgtgaac ggcttcccta tgcacctgaa   4500
gggcagcacc ggaaaacagc tgattctgca gggtgccgtg cagctgtgcc tgaacaacga   4560
gaacatcaag tacctcaaga aagtgacgaa gtacctcgag tacaacgccc agcggagaga   4620
caagagaacc ctgctcgaag ttcgggaagt gaccggaatc aacaaagagg aaaacatcca   4680
gctgtacgat gtgttcgtgg acaagctgag caacacaatc taccagtaca gacccgccaa   4740
tcctaaggac aacctcatca agggccgcga gaaattcatc gagcttggcc tggctgagca   4800
gtgcgtggtg ctgggagaag tgctgcatct gttccagtgc aagcccctga ccagcgatct   4860
gacactgatc ggcggaagcc ctaacaccgg caccatcaag atcaccaaga ccatcagcaa   4920
ctgcaacgtg gtcaagctgc tgtcccagtc tatcgccggc gtgaaagtcc gcgagatcaa   4980
cctgctgatc atcggatcct acccatacga tgttccagat tacgcggccg ctccaaaaaa   5040
gaaaagaaaa gttgaattcg gcggcagcgg cgccaccaac ttcagcctgc tgaagcaggc   5100
cggcgacgtg gaggagaacc ccggccccat ggtgagcaag ggcgaggagg ataacatggc   5160
catcatcaag gagttcatgc gcttcaaggt gcacatggag ggctccgtga acggccacga   5220
```

```
gttcgagatc gagggcgagg gcgagggccg cccctacgag ggcacccaga ccgccaagct   5280
gaaggtgacc aagggtggcc ccctgccctt cgcctgggac atcctgtccc ctcagttcat   5340
gtacggctcc aaggcctacg tgaagcaccc cgccgacatc cccgactact tgaagctgtc   5400
cttccccgag ggcttcaagt gggagcgcgt gatgaacttc gaggacggcg gcgtggtgac   5460
cgtgacccag gactcctccc tgcaggacgg cgagttcatc tacaaggtga agctgcgcgg   5520
caccaacttc ccctccgacg gccccgtaat gcagaagaag accatgggct gggaggcctc   5580
ctccgagcgg atgtaccccg aggacggcgc cctgaagggc gagatcaagc agaggctgaa   5640
gctgaaggac ggcggccact acgacgctga ggtcaagacc acctacaagg ccaagaagcc   5700
cgtgcagctg cccggcgcct acaacgtcaa catcaagttg gacatcacct cccacaacga   5760
ggactacacc atcgtggaac agtacgaacg cgccgagggc cgccactcca ccggcggcat   5820
ggacgagctg tacaagtagc tcgagtctag agggcccgtt taaacccgct gatcagcctc   5880
gactgtgcct tctagttgcc agccatctgt tgtttgcccc tcccccgtgc cttccttgac   5940
cctggaaggt gccactccca ctgtcctttc ctaataaaat gaggaaattg catcgcattg   6000
tctgagtagg tgtcattcta ttctgggggg tggggtgggg caggacagca agggggagga   6060
ttgggaagac aatagcaggc atgctgggga tgcggtgggc tctatggctt ctgaggcgga   6120
aagaaccagc tggggctcta gggggtatcc ccacgcgccc tgtagcggcg cattaagcgc   6180
ggcgggtgtg gtggttacgc gcagcgtgac cgctacactt gccagcgccc tagcgcccgc   6240
tcctttcgct ttcttccctt cctttctcgc cacgttcgcc ggctttcccc gtcaagctct   6300
aaatcggggg ctccctttag ggttccgatt tagtgcttta cggcacctcg accccaaaaa   6360
acttgattag ggtgatggtt cacgtagtgg gccatcgccc tgatagacgg tttttcgccc   6420
tttgacgttg gagtccacgt tctttaatag tggactcttg ttccaaactg gaacaacact   6480
caaccctatc tcggtctatt cttttgattt ataagggatt ttgccgattt cggcctattg   6540
gttaaaaaat gagctgattt aacaaaaatt taacgcgaat taattctgtg gaatgtgtgt   6600
cagttagggt gtggaaagtc cccaggctcc ccagcaggca gaagtatgca aagcatgcat   6660
ctcaattagt cagcaaccag gtgtggaaag tccccaggct ccccagcagg cagaagtatg   6720
caaagcatgc atctcaatta gtcagcaacc atagtcccgc ccctaactcc gcccatcccg   6780
cccctaactc cgcccagttc cgcccattct ccgccccatg gctgactaat tttttttatt   6840
tatgcagagg ccgaggccgc ctctgcctct gagctattcc agaagtagtg aggaggcttt   6900
tttggaggcc taggcttttg caaaaagctc ccgggagctt gtatatccat tttcggatct   6960
gatcaagaga caggatgagg atcgtttcgc atgattgaac aagatggatt gcacgcaggt   7020
tctccggccg cttgggtgga gaggctattc ggctatgact gggcacaaca gacaatcggc   7080
tgctctgatg ccgccgtgtt ccggctgtca gcgcaggggc gcccggttct ttttgtcaag   7140
accgacctgt ccggtgccct gaatgaactg caggacgagg cagcgcggct atcgtggctg   7200
gccacgacgg gcgttccttg cgcagctgtg ctcgacgttg tcactgaagc gggaagggac   7260
tggctgctat tgggcgaagt gccggggcag gatctcctgt catctcacct tgctcctgcc   7320
gagaaagtat ccatcatggc tgatgcaatg cggcggctgc atacgcttga tccggctacc   7380
tgcccattcg accaccaagc gaaacatcgc atcgagcgag cacgtactcg gatggaagcc   7440
ggtcttgtcg atcaggatga tctggacgaa gagcatcagg ggctcgcgcc agccgaactg   7500
ttcgccaggc tcaaggcgcg catgcccgac ggcgaggatc tcgtcgtgac ccatggcgat   7560
```

```
gcctgcttgc cgaatatcat ggtggaaaat ggccgctttt ctggattcat cgactgtggc   7620
cggctgggtg tggcggaccg ctatcaggac atagcgttgg ctacccgtga tattgctgaa   7680
gagcttggcg gcgaatgggc tgaccgcttc ctcgtgcttt acggtatcgc cgctcccgat   7740
tcgcagcgca tcgccttcta tcgccttctt gacgagttct tctgagcggg actctggggt   7800
tcgaaatgac cgaccaagcg acgcccaacc tgccatcacg agatttcgat tccaccgccg   7860
ccttctatga aaggttgggc ttcggaatcg ttttccggga cgccggctgg atgatcctcc   7920
agcgcgggga tctcatgctg gagttcttcg cccaccccaa cttgtttatt gcagcttata   7980
atggttacaa ataaagcaat agcatcacaa atttcacaaa taaagcattt ttttcactgc   8040
attctagttg tggtttgtcc aaactcatca atgtatctta tcatgtctgt ataccgtcga   8100
cctctagcta gagcttggcg taatcatggt catagctgtt tcctgtgtga aattgttatc   8160
cgctcacaat tccacacaac atacgagccg gaagcataaa gtgtaaagcc tggggtgcct   8220
aatgagtgag ctaactcaca ttaattgcgt tgcgctcact gcccgctttc cagtcgggaa   8280
acctgtcgtg ccagctgcat taatgaatcg gccaacgcgc ggggagaggc ggtttgcgta   8340
ttgggcgctc ttccgcttcc tcgctcactg actcgctgcg ctcggtcgtt cggctgcggc   8400
gagcggtatc agctcactca aaggcggtaa tacggttatc cacagaatca ggggataacg   8460
caggaaagaa catgtgagca aaaggccagc aaaaggccag gaaccgtaaa aaggccgcgt   8520
tgctggcgtt tttccatagg ctccgccccc ctgacgagca tcacaaaaat cgacgctcaa   8580
gtcagaggtg gcgaaacccg acaggactat aaagatacca ggcgtttccc cctggaagct   8640
ccctcgtgcg ctctcctgtt ccgaccctgc cgcttaccgg atacctgtcc gcctttctcc   8700
cttcgggaag cgtggcgctt tctcatagct cacgctgtag gtatctcagt tcggtgtagg   8760
tcgttcgctc caagctgggc tgtgtgcacg aaccccccgt tcagcccgac cgctgcgcct   8820
tatccggtaa ctatcgtctt gagtccaacc cggtaagaca cgacttatcg ccactggcag   8880
cagccactgg taacaggatt agcagagcga ggtatgtagg cggtgctaca gagttcttga   8940
agtggtggcc taactacggc tacactagaa gaacagtatt tggtatctgc gctctgctga   9000
agccagttac cttcggaaaa agagttggta gctcttgatc cggcaaacaa accaccgctg   9060
gtagcggtgg tttttttgtt tgcaagcagc agattacgcg cagaaaaaaa ggatctcaag   9120
aagatccttt gatcttttct acggggtctg acgctcagtg gaacgaaaac tcacgttaag   9180
ggattttggt catgagatta tcaaaaagga tcttcaccta gatcctttta aattaaaaat   9240
gaagttttaa atcaatctaa agtatatatg agtaaacttg gtctgacagt taccaatgct   9300
taatcagtga ggcacctatc tcagcgatct gtctatttcg ttcatccata gttgcctgac   9360
tccccgtcgt gtagataact acgatacggg agggcttacc atctggcccc agtgctgcaa   9420
tgataccgcg agacccacgc tcaccggctc cagatttatc agcaataaac cagccagccg   9480
gaagggccga gcgcagaagt ggtcctgcaa ctttatccgc ctccatccag tctattaatt   9540
gttgccggga agctagagta agtagttcgc cagttaatag tttgcgcaac gttgttgcca   9600
ttgctacagg catcgtggtg tcacgctcgt cgtttggtat ggcttcattc agctccggtt   9660
cccaacgatc aaggcgagtt acatgatccc ccatgttgtg caaaaaagcg gttagctcct   9720
tcggtcctcc gatcgttgtc agaagtaagt tggccgcagt gttatcactc atggttatgg   9780
cagcactgca taattctctt actgtcatgc catccgtaag atgcttttct gtgactggtg   9840
agtactcaac caagtcattc tgagaatagt gtatgcggcg accgagttgc tcttgcccgg   9900
cgtcaatacg ggataatacc gcgccacata gcagaacttt aaaagtgctc atcattggaa   9960
```

```
aacgttcttc ggggcgaaaa ctctcaagga tcttaccgct gttgagatcc agttcgatgt  10020

aacccactcg tgcacccaac tgatcttcag catcttttac tttcaccagc gtttctgggt  10080

gagcaaaaac aggaaggcaa aatgccgcaa aaaagggaat aagggcgaca cggaaatgtt  10140

gaatactcat actcttcctt tttcaatatt attgaagcat ttatcagggt tattgtctca  10200

tgagcggata catatttgaa tgtatttaga aaaataaaca aataggggtt ccgcgcacat  10260

ttccccgaaa agtgccacct gacgtc                                       10286
```

```
<210> SEQ ID NO 41
<211> LENGTH: 9
<212> TYPE: PRT
<213> ORGANISM: Artificial Sequence
<220> FEATURE:
<223> OTHER INFORMATION: HA Tag amino acid sequence

<400> SEQUENCE: 41

Tyr Pro Tyr Asp Val Pro Asp Tyr Ala
1               5


<210> SEQ ID NO 42
<211> LENGTH: 7
<212> TYPE: PRT
<213> ORGANISM: Artificial Sequence
<220> FEATURE:
<223> OTHER INFORMATION: SV40 NLS amino acid sequence

<400> SEQUENCE: 42

Pro Lys Lys Lys Arg Lys Val
1               5


<210> SEQ ID NO 43
<211> LENGTH: 19
<212> TYPE: PRT
<213> ORGANISM: Artificial Sequence
<220> FEATURE:
<223> OTHER INFORMATION: P2A amino acid sequence

<400> SEQUENCE: 43

Ala Thr Asn Phe Ser Leu Leu Lys Gln Ala Gly Asp Val Glu Glu Asn
1               5                   10                  15

Pro Gly Pro


<210> SEQ ID NO 44
<211> LENGTH: 236
<212> TYPE: PRT
<213> ORGANISM: Artificial Sequence
<220> FEATURE:
<223> OTHER INFORMATION: mCherry amino acid sequence

<400> SEQUENCE: 44

Met Val Ser Lys Gly Glu Glu Asp Asn Met Ala Ile Ile Lys Glu Phe
1               5                   10                  15

Met Arg Phe Lys Val His Met Glu Gly Ser Val Asn Gly His Glu Phe
            20                  25                  30

Glu Ile Glu Gly Glu Gly Glu Gly Arg Pro Tyr Glu Gly Thr Gln Thr
        35                  40                  45

Ala Lys Leu Lys Val Thr Lys Gly Gly Pro Leu Pro Phe Ala Trp Asp
    50                  55                  60

Ile Leu Ser Pro Gln Phe Met Tyr Gly Ser Lys Ala Tyr Val Lys His
65                  70                  75                  80
```

```
Pro Ala Asp Ile Pro Asp Tyr Leu Lys Leu Ser Phe Pro Glu Gly Phe
                85                  90                  95

Lys Trp Glu Arg Val Met Asn Phe Glu Asp Gly Gly Val Val Thr Val
            100                 105                 110

Thr Gln Asp Ser Ser Leu Gln Asp Gly Glu Phe Ile Tyr Lys Val Lys
        115                 120                 125

Leu Arg Gly Thr Asn Phe Pro Ser Asp Gly Pro Val Met Gln Lys Lys
    130                 135                 140

Thr Met Gly Trp Glu Ala Ser Ser Glu Arg Met Tyr Pro Glu Asp Gly
145                 150                 155                 160

Ala Leu Lys Gly Glu Ile Lys Gln Arg Leu Lys Leu Lys Asp Gly Gly
                165                 170                 175

His Tyr Asp Ala Glu Val Lys Thr Thr Tyr Lys Ala Lys Lys Pro Val
            180                 185                 190

Gln Leu Pro Gly Ala Tyr Asn Val Asn Ile Lys Leu Asp Ile Thr Ser
        195                 200                 205

His Asn Glu Asp Tyr Thr Ile Val Glu Gln Tyr Glu Arg Ala Glu Gly
    210                 215                 220

Arg His Ser Thr Gly Gly Met Asp Glu Leu Tyr Lys
225                 230                 235
```

<210> SEQ ID NO 45
<211> LENGTH: 27
<212> TYPE: DNA
<213> ORGANISM: Artificial Sequence
<220> FEATURE:
<223> OTHER INFORMATION: HA Tag DNA sequence

<400> SEQUENCE: 45

```
tacccatacg atgttccaga ttacgct                                          27
```

<210> SEQ ID NO 46
<211> LENGTH: 21
<212> TYPE: DNA
<213> ORGANISM: Artificial Sequence
<220> FEATURE:
<223> OTHER INFORMATION: SV40 NLS DNA sequence

<400> SEQUENCE: 46

```
ccaaaaaaga aaagaaaagt t                                                21
```

<210> SEQ ID NO 47
<211> LENGTH: 57
<212> TYPE: DNA
<213> ORGANISM: Artificial Sequence
<220> FEATURE:
<223> OTHER INFORMATION: P2A DNA sequence

<400> SEQUENCE: 47

```
gccaccaact tcagcctgct gaagcaggcc ggcgacgtgg aggagaaccc cggcccc         57
```

<210> SEQ ID NO 48
<211> LENGTH: 711
<212> TYPE: DNA
<213> ORGANISM: Artificial Sequence
<220> FEATURE:
<223> OTHER INFORMATION: mCherry DNA sequence

<400> SEQUENCE: 48

```
atggtgagca agggcgagga ggataacatg gccatcatca aggagttcat gcgcttcaag      60

gtgcacatgg agggctccgt gaacggccac gagttcgaga tcgagggcga gggcgagggc     120
```

```
cgcccctacg agggcaccca gaccgccaag ctgaaggtga ccaagggtgg cccccctgccc    180

ttcgcctggg acatcctgtc ccctcagttc atgtacggct ccaaggccta cgtgaagcac    240

cccgccgaca tccccgacta cttgaagctg tccttccccg agggcttcaa gtgggagcgc    300

gtgatgaact tcgaggacgg cggcgtggtg accgtgaccc aggactcctc cctgcaggac    360

ggcgagttca tctacaaggt gaagctgcgc ggcaccaact tcccctccga cggccccgta    420

atgcagaaga agaccatggg ctgggaggcc tcctccgagc ggatgtaccc cgaggacggc    480

gccctgaagg gcgagatcaa gcagaggctg aagctgaagg acggcggcca ctacgacgct    540

gaggtcaaga ccacctacaa ggccaagaag cccgtgcagc tgcccggcgc ctacaacgtc    600

aacatcaagt tggacatcac ctcccacaac gaggactaca ccatcgtgga acagtacgaa    660

cgcgccgagg gccgccactc caccggcggc atggacgagc tgtacaagta g             711


<210> SEQ ID NO 49
<211> LENGTH: 22
<212> TYPE: RNA
<213> ORGANISM: Artificial Sequence
<220> FEATURE:
<223> OTHER INFORMATION: OMNI-103_B2M_s11-ref

<400> SEQUENCE: 49

ggaccagagc gggaggguag ga                                              22


<210> SEQ ID NO 50
<211> LENGTH: 22
<212> TYPE: RNA
<213> ORGANISM: Artificial Sequence
<220> FEATURE:
<223> OTHER INFORMATION: OMNI-103_B2M_s12-ref

<400> SEQUENCE: 50

guaugccugc cgugugaacc au                                              22


<210> SEQ ID NO 51
<211> LENGTH: 22
<212> TYPE: RNA
<213> ORGANISM: Artificial Sequence
<220> FEATURE:
<223> OTHER INFORMATION: OMNI-103_B2M_S26 -ref

<400> SEQUENCE: 51

ucucucucca uucuucagua ag                                              22


<210> SEQ ID NO 52
<211> LENGTH: 22
<212> TYPE: RNA
<213> ORGANISM: Artificial Sequence
<220> FEATURE:
<223> OTHER INFORMATION: OMNI-103_B2M_S27 -ref

<400> SEQUENCE: 52

agaauugaaa aaguggagca uu                                              22


<210> SEQ ID NO 53
<211> LENGTH: 22
<212> TYPE: RNA
<213> ORGANISM: Artificial Sequence
<220> FEATURE:
<223> OTHER INFORMATION: OMNI-103_B2M_S40 -ref

<400> SEQUENCE: 53
```

```
aagaauguaa gacuuacccc ac                                            22


<210> SEQ ID NO 54
<211> LENGTH: 22
<212> TYPE: RNA
<213> ORGANISM: Artificial Sequence
<220> FEATURE:
<223> OTHER INFORMATION: OMNI-103_B2M_S41 -ref

<400> SEQUENCE: 54

ucagcagcuu acaaaagaau gu                                            22


<210> SEQ ID NO 55
<211> LENGTH: 22
<212> TYPE: RNA
<213> ORGANISM: Artificial Sequence
<220> FEATURE:
<223> OTHER INFORMATION: OMNI-103_B2M_S48 -ref

<400> SEQUENCE: 55

cgucgcgcug gcgggcauuc cu                                            22


<210> SEQ ID NO 56
<211> LENGTH: 22
<212> TYPE: RNA
<213> ORGANISM: Artificial Sequence
<220> FEATURE:
<223> OTHER INFORMATION: OMNI-103_B2M_S49 -ref

<400> SEQUENCE: 56

agacaucucg gcccgaaugc ug                                            22


<210> SEQ ID NO 57
<211> LENGTH: 22
<212> TYPE: RNA
<213> ORGANISM: Artificial Sequence
<220> FEATURE:
<223> OTHER INFORMATION: OMNI-103_CXCR4_S35-ref

<400> SEQUENCE: 57

cuggagugaa aacuugaaga cu                                            22


<210> SEQ ID NO 58
<211> LENGTH: 22
<212> TYPE: RNA
<213> ORGANISM: Artificial Sequence
<220> FEATURE:
<223> OTHER INFORMATION: OMNI-103_CXCR4_s93-ref

<400> SEQUENCE: 58

gggguucaga caacagugga ag                                            22


<210> SEQ ID NO 59
<211> LENGTH: 22
<212> TYPE: RNA
<213> ORGANISM: Artificial Sequence
<220> FEATURE:
<223> OTHER INFORMATION: OMNI-103_ELANE_g114-ref

<400> SEQUENCE: 59

gguguuaugg ucacagcggg ug                                            22


<210> SEQ ID NO 60
<211> LENGTH: 22
<212> TYPE: RNA
<213> ORGANISM: Artificial Sequence
```

<220> FEATURE:
<223> OTHER INFORMATION: OMNI-103_ELANE_g115-alt

<400> SEQUENCE: 60
ugggaauccc auucccgcag cu 22

<210> SEQ ID NO 61
<211> LENGTH: 22
<212> TYPE: RNA
<213> ORGANISM: Artificial Sequence
<220> FEATURE:
<223> OTHER INFORMATION: OMNI-103_ELANE_g128-ref

<400> SEQUENCE: 61
ugcuccccac ccgcucccag cc 22

<210> SEQ ID NO 62
<211> LENGTH: 22
<212> TYPE: RNA
<213> ORGANISM: Artificial Sequence
<220> FEATURE:
<223> OTHER INFORMATION: OMNI-103_PDCD1_S40-ref

<400> SEQUENCE: 62
aacacaucgg agagcuucgu gc 22

<210> SEQ ID NO 63
<211> LENGTH: 22
<212> TYPE: RNA
<213> ORGANISM: Artificial Sequence
<220> FEATURE:
<223> OTHER INFORMATION: OMNI-103_PDCD1_S92-ref

<400> SEQUENCE: 63
gaggaccgca gccagcccgg cc 22

<210> SEQ ID NO 64
<211> LENGTH: 22
<212> TYPE: RNA
<213> ORGANISM: Artificial Sequence
<220> FEATURE:
<223> OTHER INFORMATION: OMNI-103_SAMD9_g34-ref

<400> SEQUENCE: 64
gccaagaccc uuuaaacaga cc 22

<210> SEQ ID NO 65
<211> LENGTH: 22
<212> TYPE: RNA
<213> ORGANISM: Artificial Sequence
<220> FEATURE:
<223> OTHER INFORMATION: OMNI-103_SAMD9_g36-ref

<400> SEQUENCE: 65
guaauaccag agugaagauu au 22

<210> SEQ ID NO 66
<211> LENGTH: 22
<212> TYPE: RNA
<213> ORGANISM: Artificial Sequence
<220> FEATURE:
<223> OTHER INFORMATION: OMNI-103_SAMD9L_g133-alt

<400> SEQUENCE: 66
aggaacaaag agccuuuggu gc 22

<210> SEQ ID NO 67
<211> LENGTH: 22
<212> TYPE: RNA
<213> ORGANISM: Artificial Sequence
<220> FEATURE:
<223> OTHER INFORMATION: OMNI-103_SAMD9L_g79-alt

<400> SEQUENCE: 67
ugacuucugu cuacgcuaca ga 22

<210> SEQ ID NO 68
<211> LENGTH: 22
<212> TYPE: RNA
<213> ORGANISM: Artificial Sequence
<220> FEATURE:
<223> OTHER INFORMATION: OMNI-103_SAMD9L_g80-alt

<400> SEQUENCE: 68
gcauucuaga gccuggaauu ua 22

<210> SEQ ID NO 69
<211> LENGTH: 22
<212> TYPE: RNA
<213> ORGANISM: Artificial Sequence
<220> FEATURE:
<223> OTHER INFORMATION: OMNI-103_SARM1_g42-ref

<400> SEQUENCE: 69
cgcgcggccu gcacacgcgu cu 22

<210> SEQ ID NO 70
<211> LENGTH: 22
<212> TYPE: RNA
<213> ORGANISM: Artificial Sequence
<220> FEATURE:
<223> OTHER INFORMATION: OMNI-103_SARM1_g43-ref

<400> SEQUENCE: 70
cgccacugcg cgcuggcgcu gg 22

<210> SEQ ID NO 71
<211> LENGTH: 22
<212> TYPE: RNA
<213> ORGANISM: Artificial Sequence
<220> FEATURE:
<223> OTHER INFORMATION: OMNI-103_SARM1_g44-ref

<400> SEQUENCE: 71
gugucugagc agcagcugcu gg 22

<210> SEQ ID NO 72
<211> LENGTH: 22
<212> TYPE: RNA
<213> ORGANISM: Artificial Sequence
<220> FEATURE:
<223> OTHER INFORMATION: OMNI-103_SARM1_g45-ref

<400> SEQUENCE: 72
gaugucuuca ucagcuaccg cc 22

<210> SEQ ID NO 73
<211> LENGTH: 22
<212> TYPE: RNA
<213> ORGANISM: Artificial Sequence
<220> FEATURE:
<223> OTHER INFORMATION: OMNI-103_TRAC_S124 -ref

<400> SEQUENCE: 73
ucucgaccag cuugacauca ca 22

<210> SEQ ID NO 74
<211> LENGTH: 22
<212> TYPE: RNA
<213> ORGANISM: Artificial Sequence
<220> FEATURE:
<223> OTHER INFORMATION: OMNI-103_TRAC_S141 -ref

<400> SEQUENCE: 74
cuugguuuua cagauacgaa cc 22

<210> SEQ ID NO 75
<211> LENGTH: 22
<212> TYPE: RNA
<213> ORGANISM: Artificial Sequence
<220> FEATURE:
<223> OTHER INFORMATION: OMNI-103_TRAC_S142 -ref

<400> SEQUENCE: 75
cgucaugagc agauuaaacc cg 22

<210> SEQ ID NO 76
<211> LENGTH: 22
<212> TYPE: RNA
<213> ORGANISM: Artificial Sequence
<220> FEATURE:
<223> OTHER INFORMATION: OMNI-103_TRAC_S24-ref

<400> SEQUENCE: 76
acugugcuag acaugagguc ua 22

<210> SEQ ID NO 77
<211> LENGTH: 22
<212> TYPE: RNA
<213> ORGANISM: Artificial Sequence
<220> FEATURE:
<223> OTHER INFORMATION: OMNI-103_TRAC_S35-ref

<400> SEQUENCE: 77
gacccugccg uguaccagcu ga 22

<210> SEQ ID NO 78
<211> LENGTH: 22
<212> TYPE: RNA
<213> ORGANISM: Artificial Sequence
<220> FEATURE:
<223> OTHER INFORMATION: OMNI-103_TRAC_S36-ref

<400> SEQUENCE: 78
ucaaaaucgg ugaauaggca ga 22

<210> SEQ ID NO 79
<211> LENGTH: 22
<212> TYPE: RNA
<213> ORGANISM: Artificial Sequence
<220> FEATURE:
<223> OTHER INFORMATION: OMNI-103_TRAC_S58-ref

<400> SEQUENCE: 79
agaacccuga cccugccgug ua 22

<210> SEQ ID NO 80

<211> LENGTH: 22
<212> TYPE: RNA
<213> ORGANISM: Artificial Sequence
<220> FEATURE:
<223> OTHER INFORMATION: OMNI-103_TRAC_s90-ref

<400> SEQUENCE: 80
uucugaugug uauaucacag ac 22

<210> SEQ ID NO 81
<211> LENGTH: 22
<212> TYPE: RNA
<213> ORGANISM: Artificial Sequence
<220> FEATURE:
<223> OTHER INFORMATION: OMNI-103_TRAC_S91-ref

<400> SEQUENCE: 81
gcuguggccu ggagcaacaa au 22

<210> SEQ ID NO 82
<211> LENGTH: 22
<212> TYPE: RNA
<213> ORGANISM: Artificial Sequence
<220> FEATURE:
<223> OTHER INFORMATION: OMNI-103_B2M_S12 spacer

<400> SEQUENCE: 82
guaugccugc cgugugaacc au 22

<210> SEQ ID NO 83
<211> LENGTH: 22
<212> TYPE: RNA
<213> ORGANISM: Artificial Sequence
<220> FEATURE:
<223> OTHER INFORMATION: OMNI-103_TRAC_S36 spacer

<400> SEQUENCE: 83
ucaaaaucgg ugaauaggca ga 22

<210> SEQ ID NO 84
<211> LENGTH: 22
<212> TYPE: RNA
<213> ORGANISM: Artificial Sequence
<220> FEATURE:
<223> OTHER INFORMATION: OMNI-103_TRAC_S35 spacer

<400> SEQUENCE: 84
gacccugccg uguaccagcu ga 22

<210> SEQ ID NO 85
<211> LENGTH: 25
<212> TYPE: RNA
<213> ORGANISM: Artificial Sequence
<220> FEATURE:
<223> OTHER INFORMATION: OMNI-103_PDCD1_S40 25nt spacer

<400> SEQUENCE: 85
uccaacacau cggagagcuu cgugc 25

<210> SEQ ID NO 86
<211> LENGTH: 24
<212> TYPE: RNA
<213> ORGANISM: Artificial Sequence
<220> FEATURE:
<223> OTHER INFORMATION: OMNI-103_PDCD1_S40 24nt spacer

<400> SEQUENCE: 86

```
ccaacacauc ggagagcuuc gugc                                          24


<210> SEQ ID NO 87
<211> LENGTH: 23
<212> TYPE: RNA
<213> ORGANISM: Artificial Sequence
<220> FEATURE:
<223> OTHER INFORMATION: OMNI-103_PDCD1_S40 23nt spacer

<400> SEQUENCE: 87

caacacaucg gagagcuucg ugc                                           23


<210> SEQ ID NO 88
<211> LENGTH: 22
<212> TYPE: RNA
<213> ORGANISM: Artificial Sequence
<220> FEATURE:
<223> OTHER INFORMATION: OMNI-103_PDCD1_S40 22nt spacer

<400> SEQUENCE: 88

aacacaucgg agagcuucgu gc                                            22


<210> SEQ ID NO 89
<211> LENGTH: 21
<212> TYPE: RNA
<213> ORGANISM: Artificial Sequence
<220> FEATURE:
<223> OTHER INFORMATION: OMNI-103_PDCD1_S40 21nt spacer

<400> SEQUENCE: 89

acacaucgga gagcuucgug c                                             21


<210> SEQ ID NO 90
<211> LENGTH: 20
<212> TYPE: RNA
<213> ORGANISM: Artificial Sequence
<220> FEATURE:
<223> OTHER INFORMATION: OMNI-103_PDCD1_S40 20nt spacer

<400> SEQUENCE: 90

cacaucggag agcuucgugc                                               20


<210> SEQ ID NO 91
<211> LENGTH: 107
<212> TYPE: RNA
<213> ORGANISM: Artificial Sequence
<220> FEATURE:
<223> OTHER INFORMATION: OMNI-103_B2M_S12 with sgRNA 12 V2 scaffold

<400> SEQUENCE: 91

guuugagagu aguguaagaa auuacacuac aaguucaaau aaaaauuuau ucaaauccau     60

uugcuacauu guguagaauu uaaagaucug gcaacagauc uuuuuuu                 107


<210> SEQ ID NO 92
<211> LENGTH: 107
<212> TYPE: RNA
<213> ORGANISM: Artificial Sequence
<220> FEATURE:
<223> OTHER INFORMATION: OMNI-103_TRAC_S36 with sgRNA 12 V2 scaffold

<400> SEQUENCE: 92

guuugagagu aguguaagaa auuacacuac aaguucaaau aaaaauuuau ucaaauccau     60

uugcuacauu guguagaauu uaaagaucug gcaacagauc uuuuuuu                 107
```

<210> SEQ ID NO 93
<211> LENGTH: 107
<212> TYPE: RNA
<213> ORGANISM: Artificial Sequence
<220> FEATURE:
<223> OTHER INFORMATION: OMNI-103_TRAC_S35 with sgRNA 12 V2 scaffold

<400> SEQUENCE: 93
guuugagagu aguguaagaa auuacacuac aaguucaaau aaaaauuuau ucaaauccau 60
uugcuacauu guguagaauu uaaagaucug gcaacagauc uuuuuuu 107

<210> SEQ ID NO 94
<211> LENGTH: 107
<212> TYPE: RNA
<213> ORGANISM: Artificial Sequence
<220> FEATURE:
<223> OTHER INFORMATION: OMNI-103_PDCD1_S40 25nt with sgRNA 12 V2 scaffold

<400> SEQUENCE: 94
guuugagagu aguguaagaa auuacacuac aaguucaaau aaaaauuuau ucaaauccau 60
uugcuacauu guguagaauu uaaagaucug gcaacagauc uuuuuuu 107

<210> SEQ ID NO 95
<211> LENGTH: 107
<212> TYPE: RNA
<213> ORGANISM: Artificial Sequence
<220> FEATURE:
<223> OTHER INFORMATION: OMNI-103_PDCD1_S40 24nt with sgRNA 12 V2 scaffold

<400> SEQUENCE: 95
guuugagagu aguguaagaa auuacacuac aaguucaaau aaaaauuuau ucaaauccau 60
uugcuacauu guguagaauu uaaagaucug gcaacagauc uuuuuuu 107

<210> SEQ ID NO 96
<211> LENGTH: 107
<212> TYPE: RNA
<213> ORGANISM: Artificial Sequence
<220> FEATURE:
<223> OTHER INFORMATION: OMNI-103_PDCD1_S40 23nt with sgRNA 12 V2 scaffold

<400> SEQUENCE: 96
guuugagagu aguguaagaa auuacacuac aaguucaaau aaaaauuuau ucaaauccau 60
uugcuacauu guguagaauu uaaagaucug gcaacagauc uuuuuuu 107

<210> SEQ ID NO 97
<211> LENGTH: 107
<212> TYPE: RNA
<213> ORGANISM: Artificial Sequence
<220> FEATURE:
<223> OTHER INFORMATION: OMNI-103_PDCD1_S40 22nt with sgRNA 12 V2 scaffold

<400> SEQUENCE: 97
guuugagagu aguguaagaa auuacacuac aaguucaaau aaaaauuuau ucaaauccau 60
uugcuacauu guguagaauu uaaagaucug gcaacagauc uuuuuuu 107

<210> SEQ ID NO 98
<211> LENGTH: 107
<212> TYPE: RNA
<213> ORGANISM: Artificial Sequence
<220> FEATURE:
<223> OTHER INFORMATION: OMNI-103_PDCD1_S40 21nt with sgRNA 12 V2 scaffold

<400> SEQUENCE: 98
guuugagagu aguguaagaa auuacacuac aaguucaaau aaaaauuuau ucaaauccau 60
uugcuacauu guguagaauu uaaagaucug gcaacagauc uuuuuuu 107

<210> SEQ ID NO 99
<211> LENGTH: 107
<212> TYPE: RNA
<213> ORGANISM: Artificial Sequence
<220> FEATURE:
<223> OTHER INFORMATION: OMNI-103_PDCD1_S40 20nt with sgRNA 12 V2 scaffold

<400> SEQUENCE: 99
guuugagagu aguguaagaa auuacacuac aaguucaaau aaaaauuuau ucaaauccau 60
uugcuacauu guguagaauu uaaagaucug gcaacagauc uuuuuuu 107

<210> SEQ ID NO 100
<211> LENGTH: 129
<212> TYPE: RNA
<213> ORGANISM: Artificial Sequence
<220> FEATURE:
<223> OTHER INFORMATION: OMNI-103_B2M_S12 full sgRNA

<400> SEQUENCE: 100
guaugccugc cgugugaacc auguuugaga guaguguaag aaauuacacu acaaguucaa 60
auaaaaauuu auucaaaucc auuugcuaca uuguguagaa uuuaaagauc uggcaacaga 120
ucuuuuuuu 129

<210> SEQ ID NO 101
<211> LENGTH: 129
<212> TYPE: RNA
<213> ORGANISM: Artificial Sequence
<220> FEATURE:
<223> OTHER INFORMATION: OMNI-103_TRAC_S36 full sgRNA

<400> SEQUENCE: 101
ucaaaaucgg ugaauaggca gaguuugaga guaguguaag aaauuacacu acaaguucaa 60
auaaaaauuu auucaaaucc auuugcuaca uuguguagaa uuuaaagauc uggcaacaga 120
ucuuuuuuu 129

<210> SEQ ID NO 102
<211> LENGTH: 129
<212> TYPE: RNA
<213> ORGANISM: Artificial Sequence
<220> FEATURE:
<223> OTHER INFORMATION: OMNI-103_TRAC_S35 full sgRNA

<400> SEQUENCE: 102
gacccugccg uguaccagcu gaguuugaga guaguguaag aaauuacacu acaaguucaa 60
auaaaaauuu auucaaaucc auuugcuaca uuguguagaa uuuaaagauc uggcaacaga 120
ucuuuuuuu 129

<210> SEQ ID NO 103
<211> LENGTH: 132
<212> TYPE: RNA
<213> ORGANISM: Artificial Sequence
<220> FEATURE:

<223> OTHER INFORMATION: OMNI-103_PDCD1_S40 25nt full sgRNA

<400> SEQUENCE: 103

```
uccaacacau cggagagcuu cgugcguuug agaguagugu aagaaauuac acuacaaguu     60

caaauaaaaa uuuauucaaa uccauuugcu acauugugua gaauuuaaag aucuggcaac    120

agaucuuuuu uu                                                        132
```

<210> SEQ ID NO 104
<211> LENGTH: 131
<212> TYPE: RNA
<213> ORGANISM: Artificial Sequence
<220> FEATURE:
<223> OTHER INFORMATION: OMNI-103_PDCD1_S40 24nt full sgRNA

<400> SEQUENCE: 104

```
ccaacacauc ggagagcuuc gugcguuuga gaguagugua agaaauuaca cuacaaguuc     60

aaauaaaaau uuauucaaau ccauuugcua cauuguguag aauuuaaaga ucuggcaaca    120

gaucuuuuuu u                                                         131
```

<210> SEQ ID NO 105
<211> LENGTH: 130
<212> TYPE: RNA
<213> ORGANISM: Artificial Sequence
<220> FEATURE:
<223> OTHER INFORMATION: OMNI-103_PDCD1_S40 23nt full sgRNA

<400> SEQUENCE: 105

```
caacacaucg gagagcuucg ugcguuugag aguaguguaa gaaauuacac uacaaguuca     60

aauaaaaauu uauucaaauc cauuugcuac auuguguaga auuuaaagau cuggcaacag    120

aucuuuuuuu                                                           130
```

<210> SEQ ID NO 106
<211> LENGTH: 129
<212> TYPE: RNA
<213> ORGANISM: Artificial Sequence
<220> FEATURE:
<223> OTHER INFORMATION: OMNI-103_PDCD1_S40 22nt full sgRNA

<400> SEQUENCE: 106

```
aacacaucgg agagcuucgu gcguuugaga guaguguaag aaauuacacu acaaguucaa     60

auaaaaauuu auucaaaucc auuugcuaca uuguguagaa uuuaaagauc uggcaacaga    120

ucuuuuuuu                                                            129
```

<210> SEQ ID NO 107
<211> LENGTH: 128
<212> TYPE: RNA
<213> ORGANISM: Artificial Sequence
<220> FEATURE:
<223> OTHER INFORMATION: OMNI-103_PDCD1_S40 21nt full sgRNA

<400> SEQUENCE: 107

```
acacaucgga gagcuucgug cguuugagag uaguguaaga aauuacacua caaguucaaa     60

uaaaaauuua uucaaaucca uuugcuacau uguguagaau uuaaagaucu ggcaacagau    120

cuuuuuuu                                                             128
```

<210> SEQ ID NO 108
<211> LENGTH: 127
<212> TYPE: RNA
<213> ORGANISM: Artificial Sequence
<220> FEATURE:
<223> OTHER INFORMATION: OMNI-103_PDCD1_S40 20nt full sgRNA

<400> SEQUENCE: 108
cacaucggag agcuucgugc guuugagagu aguguaagaa auuacacuac aaguucaaau 60
aaaaauuuau ucaaauccau uugcuacauu guguagaauu uaaagaucug gcaacagauc 120
uuuuuuu 127

<210> SEQ ID NO 109
<211> LENGTH: 101
<212> TYPE: RNA
<213> ORGANISM: Artificial Sequence
<220> FEATURE:
<223> OTHER INFORMATION: V2.1 scaffold

<400> SEQUENCE: 109
guuugagagu aguggaaaca cuacaaguuc aaauaaaaau uuauucaaau ccauuugcua 60
cauuguguag aauuuaaaga ucuggcaaca gaucuuuuuu u 101

<210> SEQ ID NO 110
<211> LENGTH: 85
<212> TYPE: RNA
<213> ORGANISM: Artificial Sequence
<220> FEATURE:
<223> OTHER INFORMATION: V2.2 scaffold

<400> SEQUENCE: 110
guuugagagu aguguaagaa auuacacuac aaguucaaau aaaaauuuau ucaaauccau 60
uugcuacauu guguagaauu uuuuu 85

<210> SEQ ID NO 111
<211> LENGTH: 79
<212> TYPE: RNA
<213> ORGANISM: Artificial Sequence
<220> FEATURE:
<223> OTHER INFORMATION: V2.3 scaffold

<400> SEQUENCE: 111
guuugagagu aguggaaaca cuacaaguuc aaauaaaaau uuauucaaau ccauuugcua 60
cauuguguag aauuuuuuu 79

<210> SEQ ID NO 112
<211> LENGTH: 95
<212> TYPE: RNA
<213> ORGANISM: Artificial Sequence
<220> FEATURE:
<223> OTHER INFORMATION: V2.4 scaffold

<400> SEQUENCE: 112
guuugagagu aguggaaaca cuacaaguuc aaauaaaaau uuauucaaau ccauuugcua 60
cauuguguag aauuuaaaga ugcaaaucuu uuuuu 95

<210> SEQ ID NO 113
<211> LENGTH: 101
<212> TYPE: RNA
<213> ORGANISM: Artificial Sequence
<220> FEATURE:
<223> OTHER INFORMATION: V2.5 scaffold

<400> SEQUENCE: 113
guuugagagu aguguaagaa auuacacuac aaguucaaau aaaaauuuau ucaaauccau 60
uugcuacauu guguagaauu uaaagaugca aaucuuuuuu u 101

<210> SEQ ID NO 114
<211> LENGTH: 14
<212> TYPE: RNA
<213> ORGANISM: Artificial Sequence
<220> FEATURE:
<223> OTHER INFORMATION: crRNA Repeat sequence A

<400> SEQUENCE: 114
guuugagagu agug 14

<210> SEQ ID NO 115
<211> LENGTH: 17
<212> TYPE: RNA
<213> ORGANISM: Artificial Sequence
<220> FEATURE:
<223> OTHER INFORMATION: crRNA Repeat sequence B

<400> SEQUENCE: 115
guuugagagu aguguaa 17

<210> SEQ ID NO 116
<211> LENGTH: 16
<212> TYPE: RNA
<213> ORGANISM: Artificial Sequence
<220> FEATURE:
<223> OTHER INFORMATION: tracrRNA antiepeat sequence A

<400> SEQUENCE: 116
cacuacaagu ucaaau 16

<210> SEQ ID NO 117
<211> LENGTH: 19
<212> TYPE: RNA
<213> ORGANISM: Artificial Sequence
<220> FEATURE:
<223> OTHER INFORMATION: tracrRNA antiepeat sequence B

<400> SEQUENCE: 117
uuacacuaca aguucaaau 19

<210> SEQ ID NO 118
<211> LENGTH: 41
<212> TYPE: RNA
<213> ORGANISM: Artificial Sequence
<220> FEATURE:
<223> OTHER INFORMATION: tracrRNA Portion 1 sequence A

<400> SEQUENCE: 118
aaaaauuuau ucaaauccau uugcuacauu guguagaauu u 41

<210> SEQ ID NO 119
<211> LENGTH: 45
<212> TYPE: RNA
<213> ORGANISM: Artificial Sequence
<220> FEATURE:
<223> OTHER INFORMATION: tracrRNA Portion 1 sequence B

<400> SEQUENCE: 119
aaaaauuuau ucaaauccau uugcuacauu guguagaauu uuuuu 45

<210> SEQ ID NO 120
<211> LENGTH: 38
<212> TYPE: RNA
<213> ORGANISM: Artificial Sequence
<220> FEATURE:
<223> OTHER INFORMATION: tracrRNA Portion 1 partial sequence

<400> SEQUENCE: 120
aaaaauuuau ucaaauccau uugcuacauu guguagaa 38

<210> SEQ ID NO 121
<211> LENGTH: 26
<212> TYPE: RNA
<213> ORGANISM: Artificial Sequence
<220> FEATURE:
<223> OTHER INFORMATION: tracrRNA Portion 2 sequence A

<400> SEQUENCE: 121
aaagaucugg caacagaucu uuuuuu 26

<210> SEQ ID NO 122
<211> LENGTH: 20
<212> TYPE: RNA
<213> ORGANISM: Artificial Sequence
<220> FEATURE:
<223> OTHER INFORMATION: tracrRNA Portion 2 sequence B

<400> SEQUENCE: 122
aaagaugcaa aucuuuuuuu 20

<210> SEQ ID NO 123
<211> LENGTH: 17
<212> TYPE: RNA
<213> ORGANISM: Artificial Sequence
<220> FEATURE:
<223> OTHER INFORMATION: tracrRNA Portion 2 - partial sequence A

<400> SEQUENCE: 123
aaagaucugg caacaga 17

<210> SEQ ID NO 124
<211> LENGTH: 13
<212> TYPE: RNA
<213> ORGANISM: Artificial Sequence
<220> FEATURE:
<223> OTHER INFORMATION: tracrRNA Portion 2 - partial sequence B

<400> SEQUENCE: 124
aaagaugcaa auc 13

<210> SEQ ID NO 125
<211> LENGTH: 22
<212> TYPE: RNA
<213> ORGANISM: Artificial Sequence
<220> FEATURE:
<223> OTHER INFORMATION: TRAC s91 spacer

<400> SEQUENCE: 125
gcuguggccu ggagcaacaa au 22

<210> SEQ ID NO 126
<211> LENGTH: 22
<212> TYPE: RNA
<213> ORGANISM: Artificial Sequence
<220> FEATURE:
<223> OTHER INFORMATION: PDCD1 s40 spacer

<400> SEQUENCE: 126
aacacaucgg agagcuucgu gc 22

<210> SEQ ID NO 127
<211> LENGTH: 22
<212> TYPE: RNA
<213> ORGANISM: Artificial Sequence
<220> FEATURE:
<223> OTHER INFORMATION: B2M s12 spacer

<400> SEQUENCE: 127
guaugccugc cgugugaacc au 22

<210> SEQ ID NO 128
<211> LENGTH: 22
<212> TYPE: RNA
<213> ORGANISM: Artificial Sequence
<220> FEATURE:
<223> OTHER INFORMATION: TRAC s35 spacer

<400> SEQUENCE: 128
gacccugccg uguaccagcu ga 22

<210> SEQ ID NO 129
<211> LENGTH: 107
<212> TYPE: RNA
<213> ORGANISM: Artificial Sequence
<220> FEATURE:
<223> OTHER INFORMATION: OMNI-103 v2.2 TRAC S35 sgRNA

<400> SEQUENCE: 129
gacccugccg uguaccagcu gaguuugaga guaguguaag aaauuacacu acaaguucaa 60
auaaaaauuu auucaaaucc auuugcuaca uuguguagaa uuuuuuu 107

<210> SEQ ID NO 130
<211> LENGTH: 101
<212> TYPE: RNA
<213> ORGANISM: Artificial Sequence
<220> FEATURE:
<223> OTHER INFORMATION: OMNI-103 v2.3 TRAC S35 sgRNA

<400> SEQUENCE: 130
gacccugccg uguaccagcu gaguuugaga guaguggaaa cacuacaagu ucaaauaaaa 60
auuuauucaa auccauuugc uacauugugu agaauuuuuu u 101

<210> SEQ ID NO 131
<211> LENGTH: 107
<212> TYPE: RNA
<213> ORGANISM: Artificial Sequence
<220> FEATURE:
<223> OTHER INFORMATION: OMNI-103 v2.2 B2M S12 sgRNA

<400> SEQUENCE: 131
guaugccugc cgugugaacc auguuugaga guaguguaag aaauuacacu acaaguucaa 60
auaaaaauuu auucaaaucc auuugcuaca uuguguagaa uuuuuuu 107

<210> SEQ ID NO 132
<211> LENGTH: 101
<212> TYPE: RNA
<213> ORGANISM: Artificial Sequence
<220> FEATURE:
<223> OTHER INFORMATION: OMNI-103 v2.3 B2M S12 sgRNA

<400> SEQUENCE: 132
guaugccugc cgugugaacc auguuugaga guaguggaaa cacuacaagu ucaaauaaaa 60
auuuauucaa auccauuugc uacauugugu agaauuuuuu u 101

<210> SEQ ID NO 133
<211> LENGTH: 28
<212> TYPE: DNA
<213> ORGANISM: Artificial Sequence
<220> FEATURE:
<223> OTHER INFORMATION: PDCD1 S40 site
<220> FEATURE:
<221> NAME/KEY: misc_feature
<222> LOCATION: (23)..(24)
<223> OTHER INFORMATION: n is a, c, g, or t

<400> SEQUENCE: 133
gaccctgccg tgtaccagct gannract 28

<210> SEQ ID NO 134
<211> LENGTH: 28
<212> TYPE: DNA
<213> ORGANISM: Artificial Sequence
<220> FEATURE:
<223> OTHER INFORMATION: TRAC S35 site
<220> FEATURE:
<221> NAME/KEY: misc_feature
<222> LOCATION: (23)..(24)
<223> OTHER INFORMATION: n is a, c, g, or t

<400> SEQUENCE: 134
aacacatcgg agagcttcgt gcnnract 28

<210> SEQ ID NO 135
<211> LENGTH: 22
<212> TYPE: DNA
<213> ORGANISM: Artificial Sequence
<220> FEATURE:
<223> OTHER INFORMATION: T2 sequence

<400> SEQUENCE: 135
ggaagagcag agccttggtc tc 22